(12) United States Patent
Mine et al.

(10) Patent No.: US 11,653,897 B2
(45) Date of Patent: May 23, 2023

(54) ULTRASONIC DIAGNOSTIC APPARATUS, SCAN SUPPORT METHOD, AND MEDICAL IMAGE PROCESSING APPARATUS

(71) Applicant: Toshiba Medical Systems Corporation, Otawara (JP)

(72) Inventors: Yoshitaka Mine, Nasushiobara (JP); Yutaka Kobayashi, Nasushiobara (JP); Jiro Higuchi, Otawara (JP); Atsushi Nakai, Nasushiobara (JP); Satoru Tezuka, Nasushiobara (JP); Kazuo Tezuka, Nasushiobara (JP); Cong Yao, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 383 days.

(21) Appl. No.: 15/644,260

(22) Filed: Jul. 7, 2017

(65) Prior Publication Data
US 2018/0008232 A1  Jan. 11, 2018

(30) Foreign Application Priority Data

Jul. 7, 2016 (JP) .............................. JP2016-135062
Nov. 16, 2016 (JP) .............................. JP2016-223312

(51) Int. Cl.
| A61B 8/00 | (2006.01) |
| A61B 8/08 | (2006.01) |
| A61B 8/14 | (2006.01) |
| G06T 15/08 | (2011.01) |
| G01S 15/89 | (2006.01) |
| G01S 7/52 | (2006.01) |
| A61B 5/055 | (2006.01) |

(52) U.S. Cl.
CPC .............. *A61B 8/4254* (2013.01); *A61B 8/08* (2013.01); *A61B 8/0875* (2013.01); 
(Continued)

(58) Field of Classification Search
CPC ..... A61B 8/4254; A61B 8/5261; A61B 8/483; A61B 8/466; A61B 8/145; A61B 8/4218;
(Continued)

(56) References Cited

U.S. PATENT DOCUMENTS 10,354,049 B2 *  7/2019 Mabotuwana ............ G06T 7/00
2003/0204139 A1  10/2003 Hashimoto
(Continued)

FOREIGN PATENT DOCUMENTS

| JP | 2002-263101 A | 9/2002 |
| JP | 2003-319939 | 11/2003 |

(Continued)

OTHER PUBLICATIONS

Office Action dated Aug. 18, 2020 in corresponding Japanese Patent Application No. 2016-223312.
(Continued)

*Primary Examiner* — Joel Lamprecht
*Assistant Examiner* — Amy J Shafqat
(74) *Attorney, Agent, or Firm* — Oblon, McClelland, Maier & Neustadt, L.L.P.

(57) ABSTRACT

An ultrasonic diagnosis apparatus includes a position detector, and control circuitry. The position detector detects a position in a three-dimensional space of one of an ultrasonic image and an ultrasonic probe. The control circuitry uses a vivisection view defined in a three-dimensional space. The control circuitry associates a structure related to a subject included in the ultrasonic image with a structure included in the vivisection view using a position and orientation in a first three-dimensional coordinate system of the structure related to the subject included in the ultrasonic image and a position and orientation in a second three-dimensional coordinate system of the structure included in the vivisection view.

23 Claims, 29 Drawing Sheets

(52) U.S. Cl.
CPC .............. *A61B 8/0891* (2013.01); *A61B 8/14* (2013.01); *A61B 8/145* (2013.01); *A61B 8/4218* (2013.01); *A61B 8/463* (2013.01); *A61B 8/466* (2013.01); *A61B 8/483* (2013.01); *A61B 8/5207* (2013.01); *A61B 8/5261* (2013.01); *G01S 7/52074* (2013.01); *G01S 15/8936* (2013.01); *G06T 15/08* (2013.01); *A61B 5/055* (2013.01); *A61B 8/486* (2013.01); *A61B 8/488* (2013.01); *G01S 15/8979* (2013.01); *G01S 15/8993* (2013.01)

(58) Field of Classification Search
CPC ......... A61B 8/14; A61B 8/463; A61B 8/0875; A61B 8/08; A61B 8/0891; A61B 8/5207; A61B 5/055; A61B 8/488; A61B 8/486; G01S 7/52074; G01S 15/8936; G01S 15/8993; G01S 15/8979; G06T 15/08
See application file for complete search history.

(56) References Cited

U.S. PATENT DOCUMENTS

| | | | | |
|---|---|---|---|---|
| 2004/0081340 | A1* | 4/2004 | Hashimoto | G01S 7/52036 382/128 |
| 2005/0089205 | A1* | 4/2005 | Kapur | A61B 8/5238 382/128 |
| 2009/0010519 | A1* | 1/2009 | Wakai | G06F 19/321 382/131 |
| 2013/0102903 | A1 | 4/2013 | Tanaka et al. | |
| 2014/0235998 | A1* | 8/2014 | Kim | G06T 7/33 600/424 |
| 2015/0131882 | A1 | 5/2015 | Mohr et al. | |
| 2015/0265254 | A1 | 9/2015 | Ishikawa et al. | |

FOREIGN PATENT DOCUMENTS

| | | |
|---|---|---|
| JP | 2009-56125 | 3/2009 |
| JP | 2013-17870 | 1/2013 |
| JP | 2013-59610 | 4/2013 |
| JP | 2015-16390 | 1/2015 |
| JP | 2015-093192 A | 5/2015 |
| WO | WO 2009/136461 A1 | 11/2009 |

OTHER PUBLICATIONS

Office Action dated Nov. 10, 2020 for corresponding Japanese Patent Application No. 2016-223312 (without translation).
Office Action dated Apr. 6, 2021 for corresponding Japanese Patent Application No. 2016-223312.

* cited by examiner

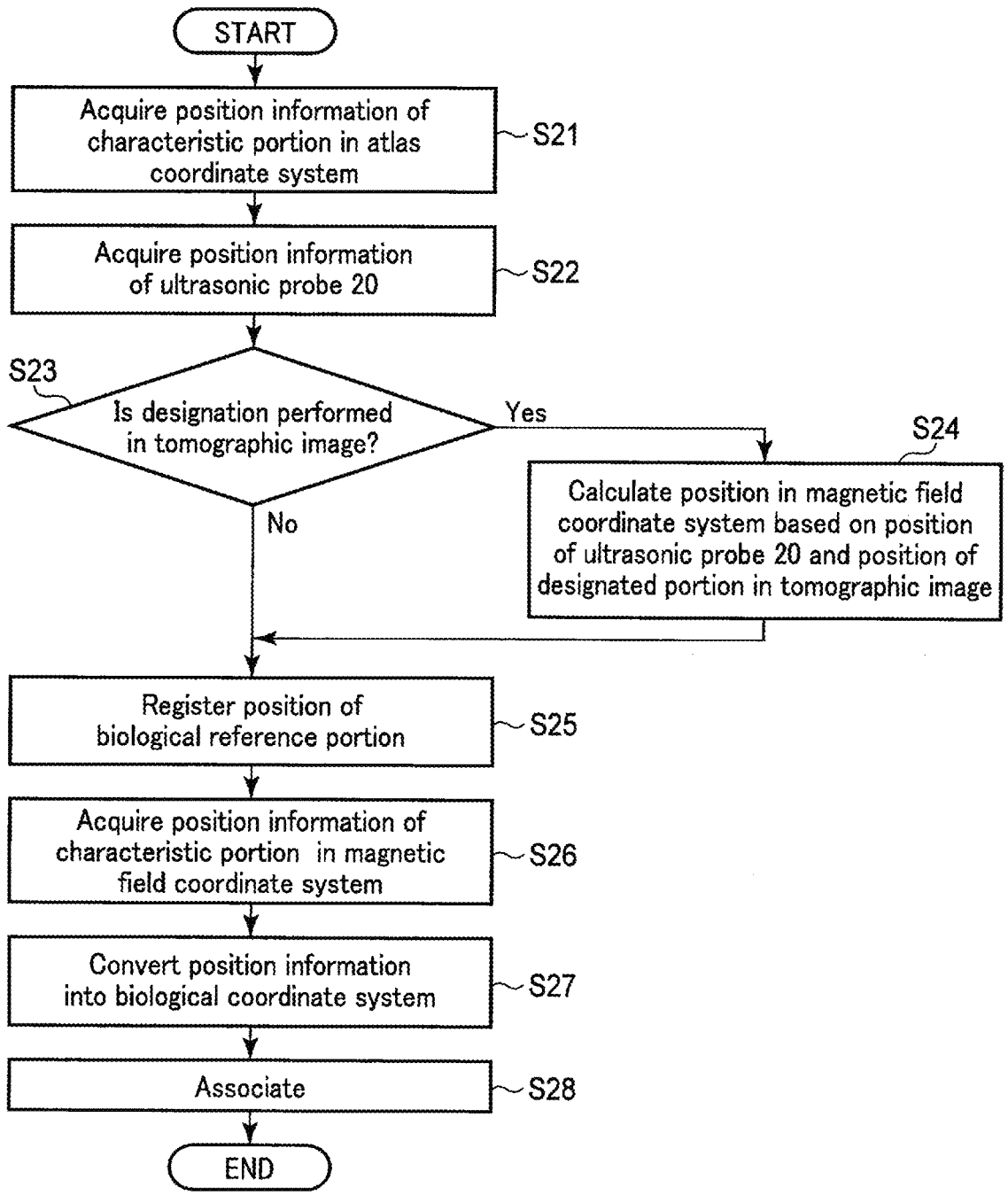
F I G. 2

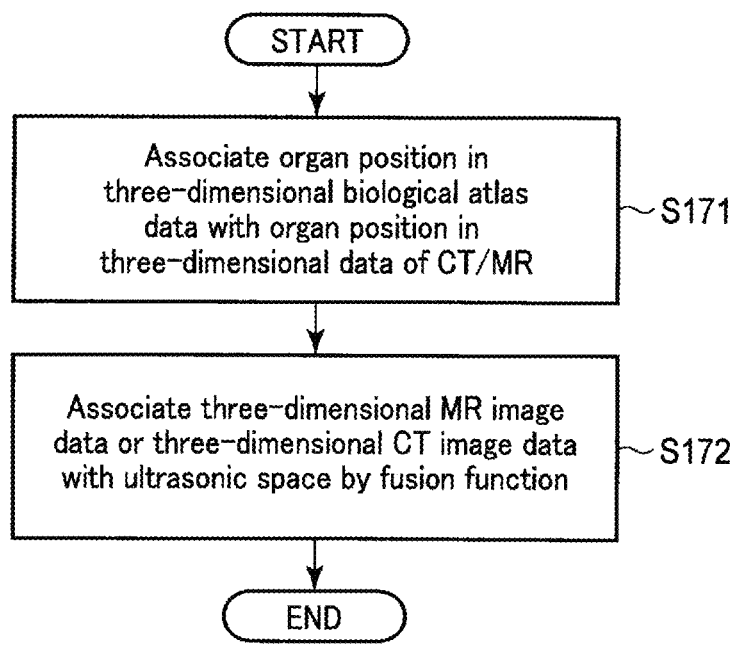
F I G. 17

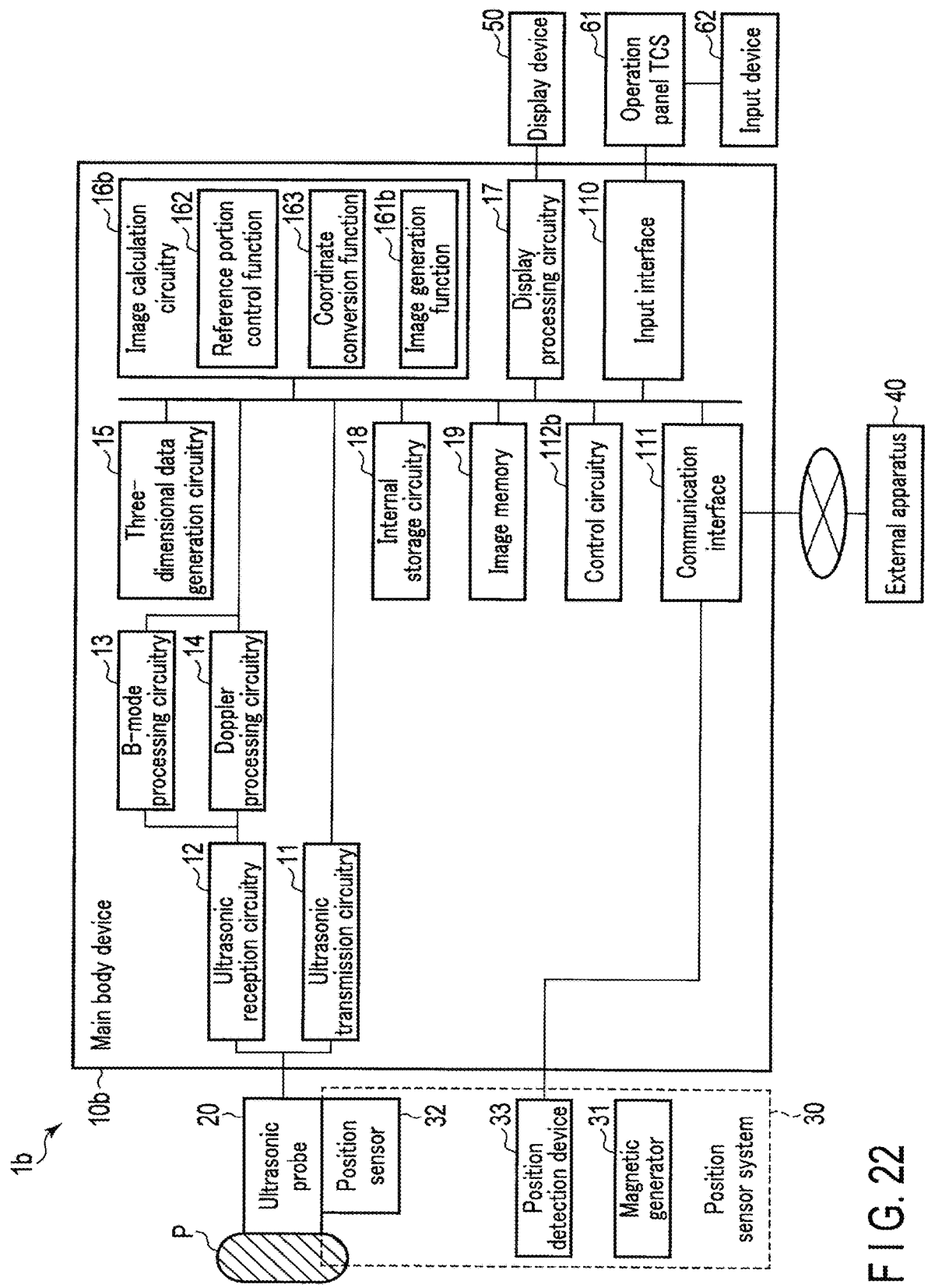
F I G. 22

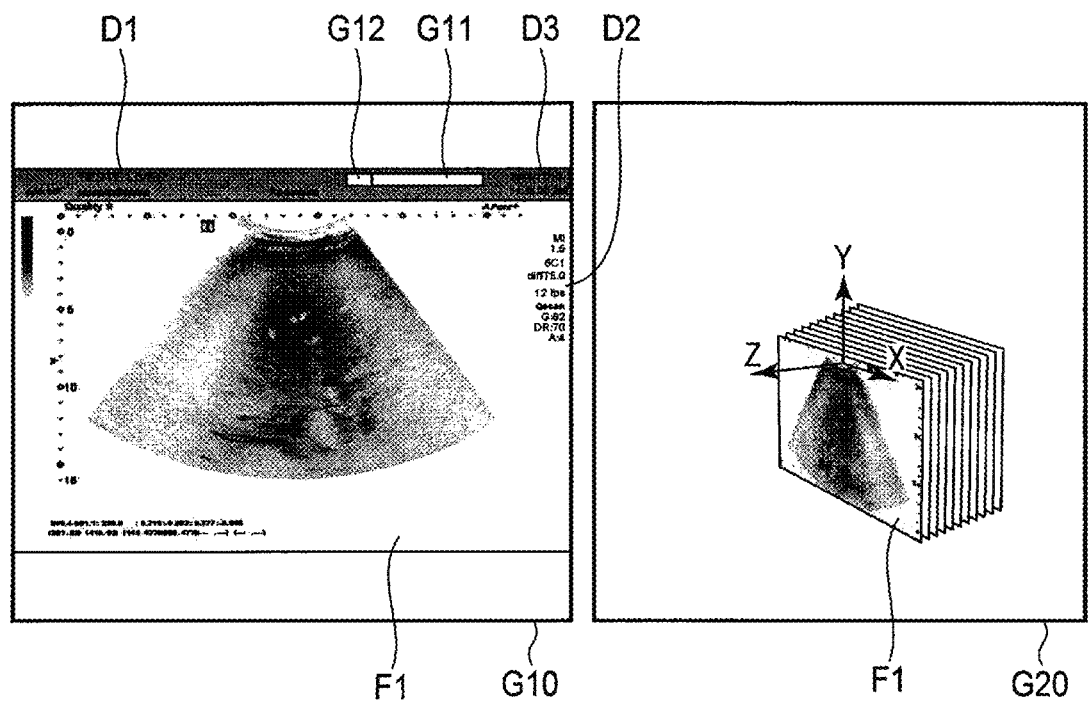
F I G. 29
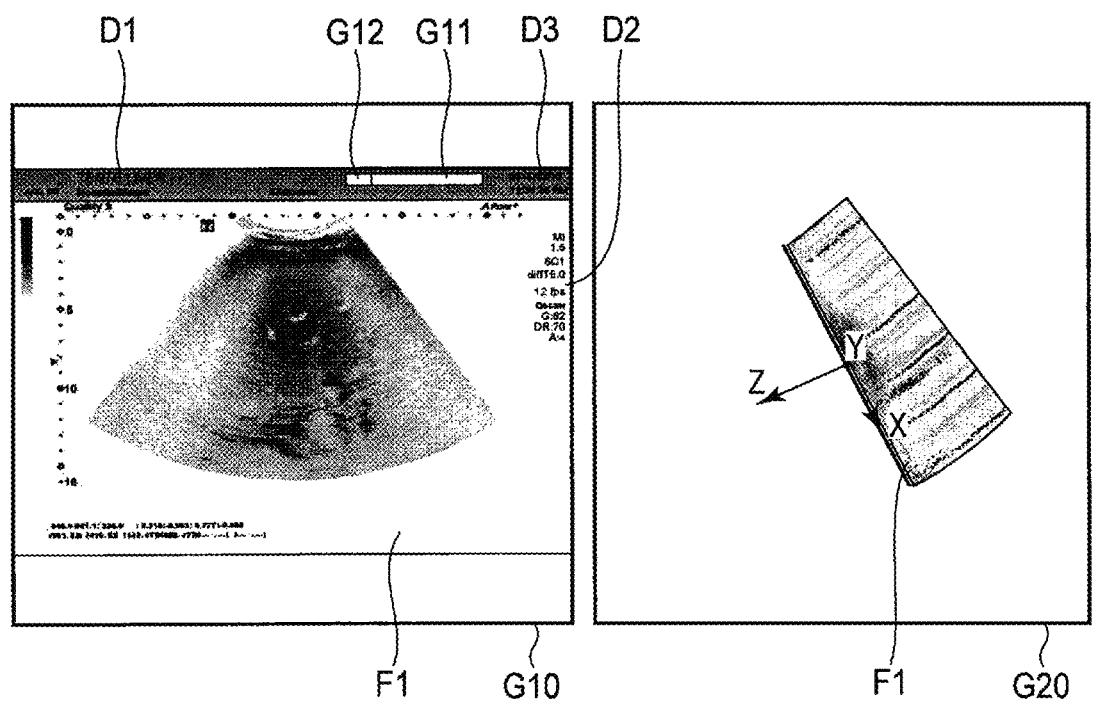
F I G. 30

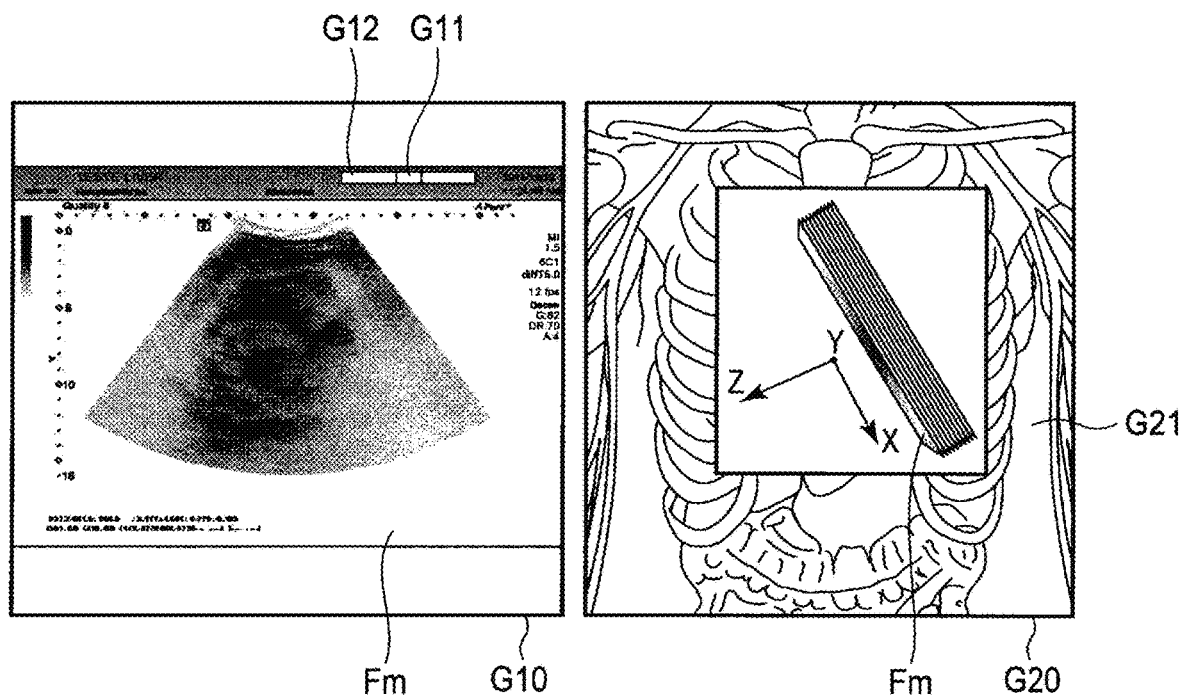
F I G. 35
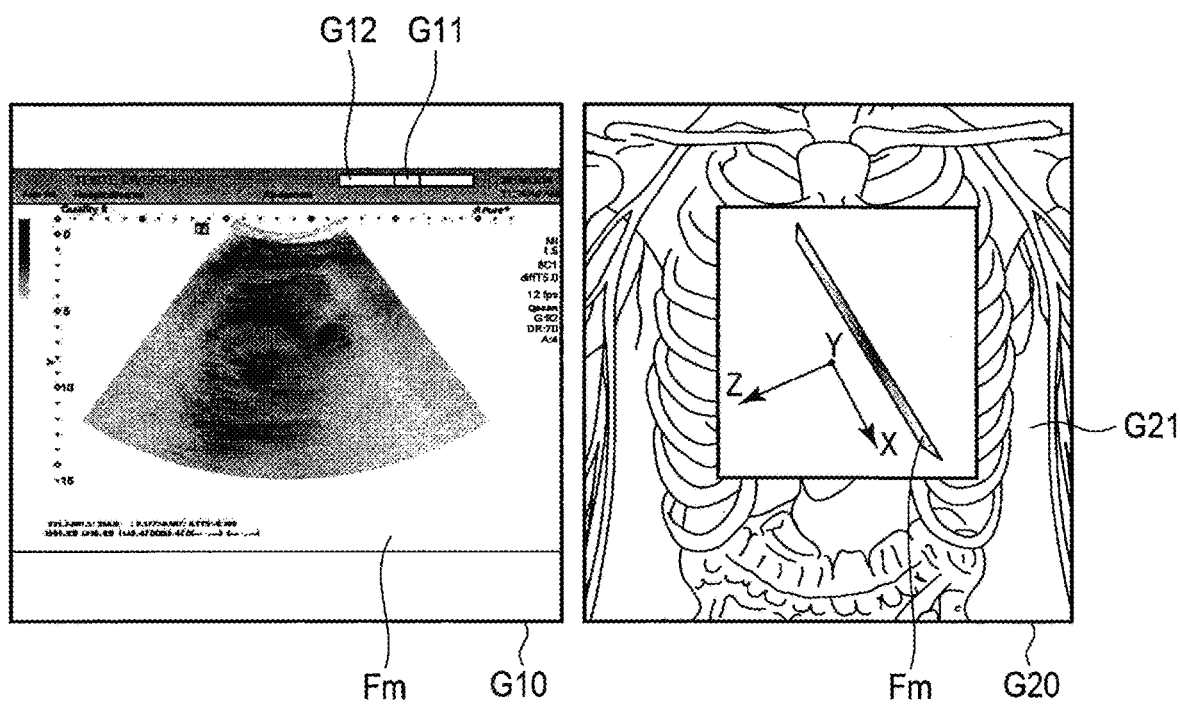
F I G. 36

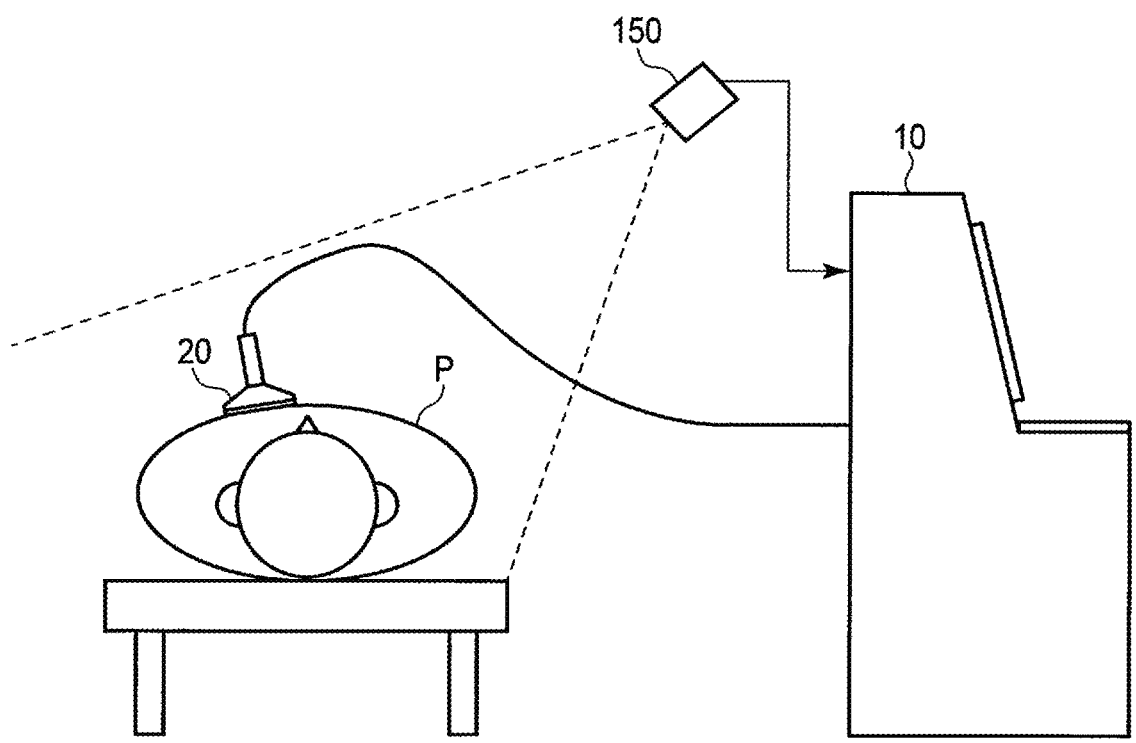
F I G. 41

ULTRASONIC DIAGNOSTIC APPARATUS, SCAN SUPPORT METHOD, AND MEDICAL IMAGE PROCESSING APPARATUS

CROSS-REFERENCE TO RELATED APPLICATIONS

This application is based upon and claims the benefit of priority from the prior Japanese Patent Application No. 2016-223312, filed Nov. 16, 2016 and No. 2016-135062, filed Jul. 7, 2016, the entire contents of both which are incorporated herein by reference.

FIELD

Embodiments described herein relate generally to an ultrasonic diagnostic apparatus, a scan support method, and a medical image processing apparatus.

BACKGROUND

As a conventional technique, there is provided an ultrasonic diagnostic apparatus which includes a mechanical four-dimensional probe for swinging a plurality of transducers arrayed in line or a two-dimensional array probe with a plurality of transducers arranged in a grid, and acquires a three-dimensional ultrasonic image in real time. There is also provided an ultrasonic diagnostic apparatus which obtains, using an ultrasonic probe attached with a position sensor, a three-dimensional ultrasonic image based on the position of the ultrasonic probe detected by the position sensor and reflection data received by the ultrasonic probe. In these ultrasonic diagnostic apparatuses, a Multi-Planar Reconstruction/Reformation (MPR) image and/or a Volume Rendering (VR) image is displayed in a three-dimensional space.

A scan operator who performs a scan acquires an ultrasonic image by bringing an ultrasonic probe into contact with the body of a patient and appropriately moving the ultrasonic probe on the surface of the body. On the other hand, since there are many organs in the body, the scan operator cannot decide, in some cases, a specific position on the living body surface with which the ultrasonic probe is brought into contact and a specific direction in the body in which the ultrasonic probe is moved in order to appropriately acquire an image of an organ to be diagnosed.

An ultrasonic scan is performed in various directions in accordance with a situation. Thus, it is difficult for a person other than the scan operator to understand, from a displayed image, a specific position on the living body surface with which the ultrasonic probe is brought into contact and a specific direction in the body in which the ultrasonic probe is moved when the displayed image is acquired.

BRIEF DESCRIPTION OF THE DRAWINGS

FIG. 2 is a flowchart illustrating the procedure of processing in which the ultrasonic diagnostic apparatus shown in FIG. 1 associates the position of an organ or the like included in an ultrasonic image with the position of an organ or the like included in a three-dimensional atlas image;

FIG. 17 is a flowchart illustrating the procedure of processing in which the ultrasonic diagnostic apparatus shown in FIG. 16 associates the position of an organ or the like included in an ultrasonic image with the position of an organ or the like included in a three-dimensional atlas image;

FIG. 22 is a block diagram showing the arrangement of an ultrasonic diagnostic apparatus according to the second embodiment;

FIG. 29 is a view showing a screen on which the map display image and one of two-dimensional images arranged in the map display image are displayed;

FIG. 30 is a view showing another example of the screen shown in FIG. 29;

FIG. 35 is a view showing a screen on which the map display image superimposed on the atlas image and one of the two-dimensional images arranged in the map display image are displayed;

FIG. 36 is a view showing a screen on which the map display image superimposed on the atlas image and the two-dimensional image arranged in the map display image are displayed;

FIG. 41 is a view showing still another configuration of the position sensor system shown in FIG. 1, 16, or 22.

DETAILED DESCRIPTION

In general, according to one embodiment, an ultrasonic diagnosis apparatus includes a position detector, and control circuitry. The position detector detects a position in a three-dimensional space of one of an ultrasonic image and an ultrasonic probe. The control circuitry uses a vivisection view defined in a three-dimensional space. The control circuitry associates a structure related to a subject included in the ultrasonic image with a structure included in the vivisection view using a position and orientation in a first three-dimensional coordinate system of the structure related to the subject included in the ultrasonic image and a position and orientation in a second three-dimensional coordinate system of the structure included in the vivisection view.

Embodiments will be described below with reference to the accompanying drawings.

First Embodiment

Figure 1:
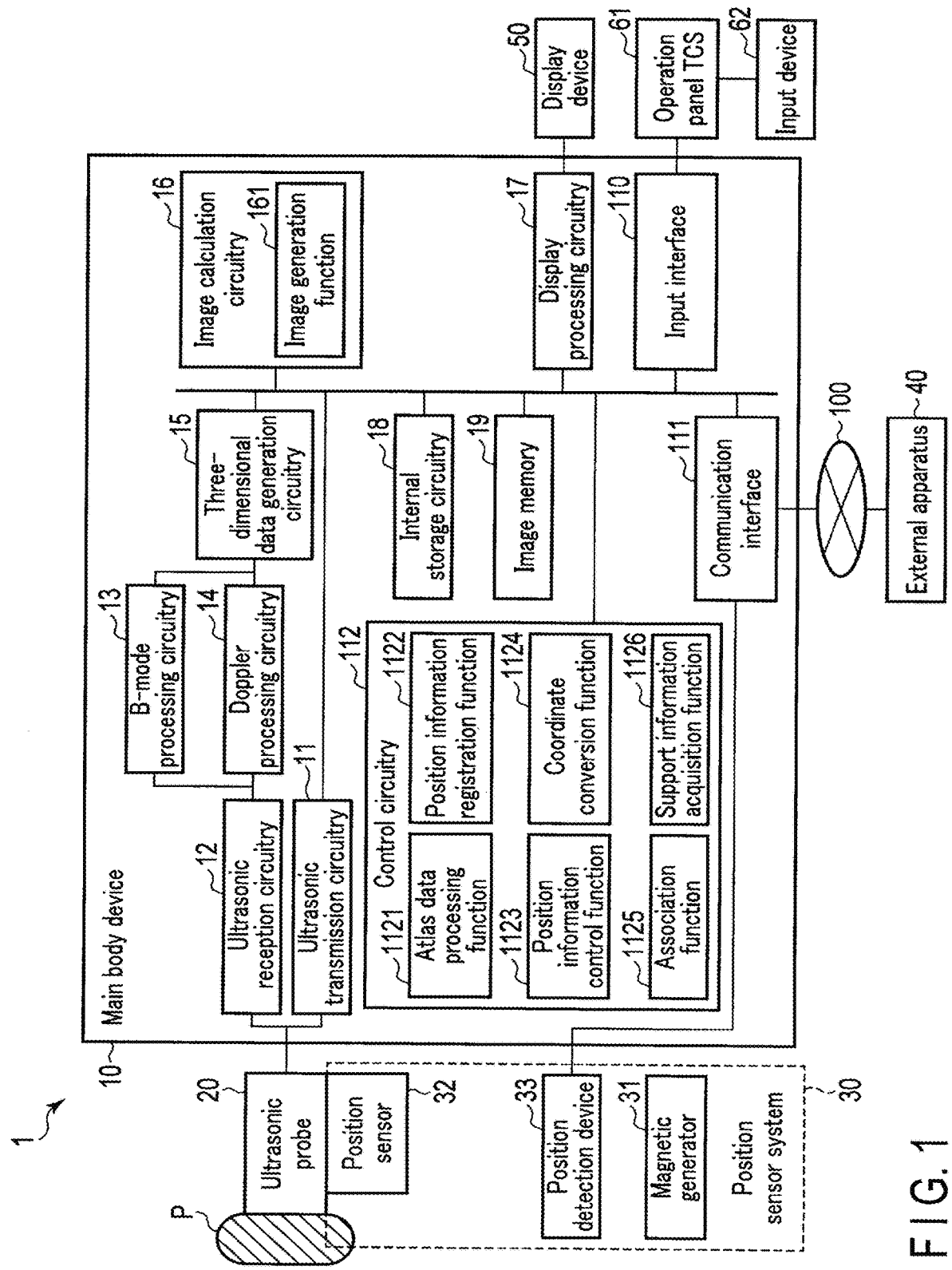
FIG. 1 is a block diagram showing the arrangement of an ultrasonic diagnostic apparatus according to the first embodiment.

FIG. 1 is a block diagram showing an example of the arrangement of an ultrasonic diagnostic apparatus 1 according to the first embodiment. As shown in FIG. 1, the ultrasonic diagnostic apparatus 1 includes a main body device 10, an ultrasonic probe 20, and a position sensor system 30. The main body device 10 is connected to an external apparatus 40 via a network 100. The main body device 10 is also connected to a display device 50.

The ultrasonic probe 20 includes a plurality of piezoelectric transducers, a matching layer provided for the piezoelectric transducers, and a backing material for preventing the ultrasonic waves from propagating backward from the piezoelectric transducers. The ultrasonic probe 20 is detachably connected to the main body device 10. Each of the plurality of piezoelectric transducers generates an ultrasonic wave based on a driving signal supplied from ultrasonic transmission circuitry 11 included in the main body device 10.

When the ultrasonic probe 20 transmits ultrasonic waves to a subject P, the transmitted ultrasonic waves are sequentially reflected by a discontinuity surface of acoustic impedance of the living tissue of the subject P, and received by the plurality of piezoelectric transducers of the ultrasonic probe 20 as a reflected wave signal. The amplitude of the received reflected wave signal depends on an acoustic impedance difference on the discontinuity surface by which the ultrasonic waves are reflected. Note that the frequency of the reflected wave signal generated when the transmitted ultrasonic pulses are reflected by moving blood or the surface of a cardiac wall or the like shifts depending on the velocity component of the moving body in the ultrasonic transmission direction due to the Doppler effect. The ultrasonic probe 20 receives the reflected wave signal from the subject P, and converts it into an electrical signal.

An operation panel 61 of the main body device 10 includes, for example, an input means formed from a button or the like for accepting, from an operator, an instruction to designate a biological reference portion (to be described later). When the operator presses the button, the operation panel 61 outputs, to the main body device 10, a designation instruction to designate the current position of the ultrasonic probe 20 as the position of the biological reference portion. Note that the input means may be provided in the ultrasonic probe 20 or a position sensor 32 provided in the position sensor system 30.

The ultrasonic probe 20 according to this embodiment scans the subject P two-dimensionally with ultrasonic waves. As shown in FIG. 1, the position sensor 32 is attached to the ultrasonic probe 20. The ultrasonic probe 20 can detect the position of the probe when the subject P is scanned three-dimensionally. More specifically, the ultrasonic probe 20 according to this embodiment is a one-dimensional probe including a plurality of ultrasonic transducers for scanning the subject P two-dimensionally.

Note that the ultrasonic probe 20 attached with the position sensor 32 may be a mechanical four-dimensional probe (a three-dimensional probe with a mechanical swinging mechanism) for scanning the subject P three-dimensionally by causing the ultrasonic transducers to swing at a predetermined angle (swinging angle), a two-dimensional array probe in which a plurality of ultrasonic transducers are arrayed in a matrix, or a 1.5-dimensional array probe in which a plurality of transducers arrayed one-dimensionally are divided into a plurality of groups.

The position sensor system 30 shown in FIG. 1 is a system for acquiring the three-dimensional position information of the ultrasonic probe 20. The position sensor system 30 acquires the three-dimensional position information of the ultrasonic probe 20 by attaching, for example, a magnetic sensor or a target for an infrared camera to the ultrasonic probe 20. Note that a gyro sensor (angular velocity sensor)

may be incorporated in the ultrasonic probe 20 and the three-dimensional position information of the ultrasonic probe 20 may be acquired by the gyro sensor. The position sensor system 30 may be a system which shoots the ultrasonic probe 20 by a camera and detects the position of the ultrasonic probe 20 in a three-dimensional space by image recognition. The position sensor system 30 may be a system which holds the ultrasonic probe 20 by a robot arm, and detects the position of the robot arm in the three-dimensional space as the position of the ultrasonic probe 20. This embodiment will exemplify a case in which the position sensor system 30 uses a magnetic sensor as the position sensor 32 to acquire the position information of the ultrasonic probe 20.

The position sensor system 30 includes a magnetic generator 31, the position sensor 32, and a position detection device 33.

The magnetic generator 31 includes, for example, a magnetic generation coil. The magnetic generator 31 is arranged at an arbitrary position, and forms a magnetic field outward with respect to the self device as the center. The position sensor 32 is attached to the ultrasonic probe 20. The position sensor 32 detects the intensity and inclination of the three-dimensional magnetic field formed by the magnetic generator 31. The position sensor 32 outputs the detected intensity and inclination of the magnetic field to the position detection device 33.

The position detection device 33 may be one example of a position detector. Based on the intensity and inclination of the magnetic field detected by the position sensor 32, the position detection device 33 calculates the position (the position coordinates (x, y, z) and rotation angles (θx, θy, θz) of a scan surface) of the ultrasonic probe 20 in the three-dimensional space having a predetermined position as an origin. At this time, the predetermined position is, for example, the position at which the magnetic generator 31 is arranged. The position detection device 33 transmits, to the main body device 10, position information about the calculated position (x, y, z, θx, θy, θz). Note that a three-dimensional coordinate system defined by the position sensor system 30 will be referred to as a magnetic field coordinate system hereinafter.

The main body device 10 shown in FIG. 1 is an apparatus which generates an ultrasonic image based on the reflected wave signal received by the ultrasonic probe 20. As shown in FIG. 1, the main body device 10 includes the ultrasonic transmission circuitry 11, ultrasonic reception circuitry 12, B-mode processing circuitry 13, Doppler processing circuitry 14, the operation panel 61, an input device 62, three-dimensional data generation circuitry 15, image calculation circuitry 16, display processing circuitry 17, internal storage circuitry 18, an image memory 19 (cine memory), an input interface 110, a communication interface 111, and control circuitry 112.

The ultrasonic transmission circuitry 11 is a processor which supplies a driving signal to the ultrasonic probe 20. The ultrasonic transmission circuitry 11 may be implemented by, for example, trigger generation circuitry, delay circuitry, and pulser circuitry. The trigger generation circuitry repetitively generates rate pulses for the formation of transmission ultrasonic waves at a predetermined rate frequency. The delay circuitry gives, to each rate pulse generated by the trigger generation circuitry, a delay time necessary to focus an ultrasonic wave generated from the ultrasonic probe 20 into a beam and determine transmission directivity for each piezoelectric transducer. The pulser circuitry applies a driving signal (driving pulse) to the ultrasonic probe 20 at the timing based on the rate pulse. When the delay circuitry changes the delay time to be given to each rate pulse, a transmission direction from the surface of the piezoelectric transducer can be arbitrarily adjusted.

The ultrasonic reception circuitry 12 is a processor which performs various processes for the reflected wave signal received by the ultrasonic probe 20, and generates a reception signal. The ultrasonic reception circuitry 12 may be implemented by, for example, amplification circuitry, an A/D converter, reception delay circuitry, and an adder. The amplification circuitry amplifies, for each channel, the reflected wave signal received by the ultrasonic probe 20, and performs gain correction processing. The A/D converter converts the reflected wave signals having undergone gain correction into digital signals. The reception delay circuitry gives the digital signals delay times necessary to determine reception directivities. The adder adds the plurality of digital signals which have been given the delay times. The addition processing by the adder generates a reception signal in which reflected components in directions according to the reception directivities are enhanced.

The B-mode processing circuitry 13 is a processor which generates B-mode data based on the reception signal received from the ultrasonic reception circuitry 12. The B-mode processing circuitry 13 performs envelope detection processing, logarithmic amplification, and the like for the reception signal received from the ultrasonic reception circuitry 12, and generates data (B-mode data) in which the signal intensity is expressed by the brightness of luminance. The generated B-mode data is stored in a RAW data memory (not shown) as B-mode RAW data on a two-dimensional ultrasonic scanning line.

The Doppler processing circuitry 14 is a processor which generates a Doppler waveform and Doppler data based on the reception signal received from the ultrasonic reception circuitry 12. The Doppler processing circuitry 14 extracts a blood flow signal from the reception signal, and generates a Doppler waveform based on the extracted blood flow signal. Furthermore, the Doppler processing circuitry 14 generates data (Doppler data) by extracting, from the extracted blood flow signal, information such as mean velocities, variances, and powers at multiple points.

The three-dimensional data generation circuitry 15 is a processor which generates three-dimensional image data with position information based on the data generated by the B-mode processing circuitry 13 and the Doppler processing circuitry 14. If the ultrasonic probe 20 attached with the position sensor 32 is a one-dimensional array probe or a 1.5-dimensional array probe, the three-dimensional data generation circuitry 15 adds the position information of the ultrasonic probe 20 calculated by the position detection device 33 to the B-mode RAW data stored in the RAW data memory. The three-dimensional data generation circuitry 15 generates two-dimensional image data formed from pixels by executing RAW-pixel conversion. The generated two-dimensional image data is added with the position information of the ultrasonic probe 20 calculated by the position detection device 33.

The three-dimensional data generation circuitry 15 generates three-dimensional image data (to be referred to as volume data hereinafter) formed from voxels within a desired range by executing, for the B-mode RAW data stored in the RAW data memory, RAW-voxel conversion including interpolation processing which takes spatial position information into consideration. The volume data is added with the position information of the ultrasonic probe 20 calculated by the position detection device 33. Similarly, if the ultrasonic probe 20 attached with the position sensor 32 is a mechanical four-dimensional probe (a three-dimensional probe with a mechanical swinging mechanism) or a two-dimensional array probe, the position information is added to two-dimensional RAW data, two-dimensional image data, and three-dimensional image data.

The three-dimensional data generation circuitry 15 performs rendering processing for the generated volume data, and generates rendering image data. Examples of the rendering processing are VR (Volume Rendering) processing, MPR (Multi Planar Reconstruction) processing, and MIP (Maximum Intensity Projection).

The three-dimensional data generation circuitry 15 adds the position information of the ultrasonic probe 20 calculated by the position detection device 33 to an M-mode image and a spectrum Doppler image collected at a desired scan position. The three-dimensional data generation circuitry 15 also adds the position information of the ultrasonic probe 20 calculated by the position detection device 33 to image quality conditions (angle of view, visual field depth, field angle, preset, frequency, image processing conditions, and the like) and scan mode information at the time of a scan, a measurement image and measurement result, and application information and an image.

The image calculation circuitry 16 is a processor which generates display image data based on the various image data generated by the three-dimensional data generation circuitry 15. The image calculation circuitry 16 implements an image generation function 161 by executing an image processing program stored in the internal storage circuitry 18.

The image generation function 161 is a function of generating display image data based on the various image data generated by the three-dimensional data generation circuitry 15 and support data stored in the internal storage circuitry 18. More specifically, upon acquiring support data, the image calculation circuitry 16 executes the image generation function 161. By executing the image generation function 161, the image calculation circuitry 16 generates display image data for displaying, side by side, the various image data generated by the three-dimensional data generation circuitry 15 and the acquired support data. The image calculation circuitry 16 generates display image data for superimposing and displaying the acquired support data on the various image data generated by the three-dimensional data generation circuitry 15.

The display processing circuitry 17 is a processor which converts the various image data generated by the three-dimensional data generation circuitry 15 and the image calculation circuitry 16 into signals displayable on the display device 50. More specifically, the display processing circuitry 17 converts the image data into video signals by executing various processes associated with a dynamic range, luminance (brightness), contrast, y curve correction, RGB conversion, and the like for the various image data. The display processing circuitry 17 displays the video signals on the display device 50. The display processing circuitry 17 may display, on the display device 50, a GUI (Graphical User Interface) used by the operator to input various instructions via the input interface 110. Note that the display processing circuitry 17 includes peripheral circuitry such as a connector and a cable for connection to the display device 50.

As the display device 50, for example, a CRT display, a liquid crystal display, an organic EL display, an LED display, a plasma display, or another arbitrary display known in the technical field can appropriately be used.

The image memory 19 includes, for example, a magnetic or optical recording medium or a processor-readable recording medium such as a semiconductor memory. The image memory 19 saves image data corresponding to a plurality of frames immediately before a freeze operation input via the input interface 110. The image data stored in the image memory 19 undergoes, for example, continuous display (cine display).

The internal storage circuitry 18 includes, for example, a magnetic or optical recording medium or a processor-readable recording medium such as a semiconductor memory. Note that the internal storage circuitry 18 need not always be implemented by a single storage device. For example, the internal storage circuitry 18 may be implemented by a plurality of storage devices.

The internal storage circuitry 18 stores a control program for implementing ultrasonic transmission/reception, a control program for performing image processing, a control program for performing display processing, and the like. The internal storage circuitry 18 also stores diagnosis information (for example, a patient ID, findings by doctors, and the like), a diagnosis protocol, a body mark generation program, and a data group such as a conversion table for presetting, for each portion to be diagnosed, a range of color data to be used for visualization.

The internal storage circuitry 18 stores support data for supporting a scan of the ultrasonic probe 20 by the scan operator. The support data includes data about a vivisection view, for example, atlas data. The atlas data includes data about an image and various data about a structure in a living body.

Examples of data about an image are atlas image data for displaying blood vessels, atlas image data for displaying muscles, atlas image data for displaying a skeletal structure, atlas image data for displaying nerves, and atlas image data for displaying organs. Each atlas image data is represented by a two- or three-dimensional atlas image. Each atlas image data may be represented by an image obtained by faithfully rendering the interior of a living body, or an image obtained by schematically rendering the interior of a living body.

Various data about the structure in the living body include data about the names of portions in the living body, data about physiological functions, diagnosis/treatment information of a disease, and data about examination findings complying with an examination guideline when examining a predetermined organ in ultrasonic diagnosis.

The support data includes data about a scan method for the ultrasonic probe 20 complying with the examination guideline.

In accordance with a storage operation input via the input interface 110, the internal storage circuitry 18 stores the two-dimensional image data, volume data, rendering image data, M-mode image data with position information, spectrum Doppler image data with position information, which have been generated by the three-dimensional data generation circuitry 15. Note that in accordance with a storage operation input via the input interface 110, the internal storage circuitry 18 may store the two-dimensional image data with position information, volume data with position information, rendering image data with position information, a Doppler waveform with position information, spectrum Doppler data with position information, which have been generated by the three-dimensional data generation circuitry 15, by including an operation order and an operation time.

Furthermore, in accordance with a storage operation input via the input interface 110, the internal storage circuitry 18 stores the display image data generated by the image calculation circuitry 16. The internal storage circuitry 18 stores the operation information of the ultrasonic diagnostic apparatus 1, image condition information, ultrasonic data about ultrasonic examination, and the like in association with the above data.

The operation information includes change of a mode, change of an image quality preset, change of a display layout, saving of an image, activation of measurement, activation of an application, and change of a probe. The image quality condition information includes ultrasonic transmission conditions such as a frequency, visual field depth, field angle, beam density, frame rate, and MI (Mechanical Index) value, image processing settings, and three-dimensional image quality parameters. The ultrasonic data includes, for example, measurement information, annotation information, biological reference information such as an ECG (Electro Cardiogram) waveform, and acquisition time information.

The internal storage circuitry 18 stores the position information of the biological reference portion.

Note that the internal storage circuitry 18 can transfer the stored data to an external peripheral apparatus via the communication interface 111.

Furthermore, the internal storage circuitry 18 stores image data transferred from the external apparatus 40. For example, the internal storage circuitry 18 acquires, from the external apparatus 40, past image data about the same patient, which has been acquired in past consultation, and stores the acquired image data. The past image data include ultrasonic image data, CT (Computed Tomography) image data, MR image data, PET (Positron Emission Tomography) image data, and X-ray image data.

The input interface 110 accepts various instructions by the operator from the input device 62 such as a mouse, keyboard, panel switch, slider switch, trackball, and rotary encoder via the operation panel and touch command screen (TCS) 61. The input interface 110 is connected to the control circuitry 112 via, for example, a bus, converts an operation instruction input from the operator into an electrical signal, and outputs the electrical signal to the control circuitry 112. Note that in this specification, the input interface 110 is not limited to an interface connected to a physical operation part such as a mouse and keyboard. For example, examples of the input interface 110 include electrical signal processing circuitry which receives an electrical signal corresponding to an operation instruction input from an external input device provided separately from the ultrasonic diagnostic apparatus 1 and outputs the electrical signal to the control circuitry 112.

The communication interface 111 is connected to the position sensor system 30, and receives the position information transmitted from the position detection device 33. The communication interface 111 is also connected to the external apparatus 40 via the network 100 or the like, and performs data communication with the external apparatus 40. The external apparatus 40 is, for example, a database for a PACS (Picture Archiving and Communication System) as a system which manages various medical image data or a database for an electronic health record system which manages electronic health records attached with medical images. The external apparatus 40 may be, for example, an X-ray CT apparatus, and various medical image diagnostic apparatuses such as an MRI (Magnetic Resonance Imaging) apparatus, a nuclear medicine diagnostic apparatus, and an X-ray diagnostic apparatus. Note that the standard of communication with the external apparatus 40 may be arbitrary. For example, DICOM (Digital Imaging and COmmunication in Medicine) is adopted.

The control circuitry 112 is a processor which serves as a center function of the ultrasonic diagnostic apparatus 1. The control circuitry 112 executes the control program stored in the internal storage circuitry 18, thereby implementing a function corresponding to the program.

More specifically, the control circuitry 112 implements processing of associating the position of an organ or the like of the subject with the position of an organ or the like included in the three-dimensional atlas image by executing the control program according to this embodiment. That is, by executing the control program, the control circuitry 112 has an atlas data processing function 1121, a position information registration function 1122, a position information control function 1123, a coordinate conversion function 1124, and an association function 1125.

The atlas data processing function 1121 is a function of acquiring the coordinate information of characteristic portions in the coordinate system of the three-dimensional atlas image. In other words, the atlas data processing function 1121 uses a vivisection view defined in the three-dimensional space. In this embodiment, the characteristic portions are characteristic structures existing in the living body, and are used to associate the position of an organ or the like of the subject with the position of an organ or the like included in the three-dimensional atlas image. The characteristic portions include a characteristic organ, a characteristic organ portion, an organ boundary, the axis of an organ, a characteristic blood vessel, and a characteristic vascular portion. Examples of the characteristic organ portion are hepatic areas S1 to S8. An example of the characteristic vascular portion is a vascular bifurcation.

More specifically, if characteristic portions are designated on the atlas image via the input interface 110, the control circuitry 112 executes the atlas data processing function 1121. By executing the atlas data processing function 1121, the control circuitry 112 acquires the coordinate information of the designated characteristic portions on the three-dimensional atlas image.

The position information registration function 1122 is a function of storing, in the internal storage circuitry 18, the position information about the structure in the subject, that is, a function of registering the position information of the biological reference portion and the position information of the characteristic portions. In this embodiment, the biological reference portion is a portion serving as the origin of the biological coordinate system.

More specifically, for example, upon receiving a designation instruction of a biological reference portion or characteristic portion, the control circuitry 112 executes the position information registration function 1122. By executing the position information registration function 1122, the control circuitry 112 stores, in the internal storage circuitry 18, the position information of the ultrasonic probe 20 in the magnetic field coordinate system of the position sensor system 30, which is acquired upon receiving the designation instruction. In the example of the position sensor 32 shown in FIG. 1, the control circuitry 112 stores, in the internal storage circuitry 18, the position information of the position sensor 32 installed in the ultrasonic probe 20. Alternatively, the control circuitry 112 may store, in the internal storage circuitry 18, as position information, a desired position such as the center of the ultrasonic transmission/reception surface of the ultrasonic probe 20 using the shape information of the ultrasonic probe 20.

The position information control function 1123 is a function of calculating the position of a portion designated via an ultrasonic tomographic image. More specifically, for example, upon receiving, from the operator, designation of a biological reference portion or characteristic portion on an ultrasonic tomographic image displayed on the display device 50, the control circuitry 112 executes the position information control function 1123. By executing the position information control function 1123, the control circuitry 112 calculates a position in the magnetic field coordinate system of the position sensor system 30 based on the position of the ultrasonic probe 20 at the time of acquiring the ultrasonic tomographic image and the position designated in the ultrasonic tomographic image.

The coordinate conversion function 1124 is a function of converting the coordinates of the designated characteristic portion into the biological coordinate system. More specifically, for example, upon acquiring the position information of the characteristic portion in the magnetic field coordinate system of the position sensor system 30, the control circuitry 112 executes the coordinate conversion function 1124. By executing the coordinate conversion function 1124, the control circuitry 112 converts the coordinates of the characteristic portion from the magnetic field coordinate system into the biological coordinate system defined based on the position of the biological reference portion. The control circuitry 112 defines the biological coordinate system based on the position (x, y, z, θx, θy, θz) of the biological reference portion in the magnetic field coordinate system. For example, the biological coordinate system is defined so that the position coordinate point (x, y, z) is set as an origin and, based on the rotation angles (θx, θy, θz), the x-axis is set in the azimuth direction as a scan direction, the y-axis is set in the depth direction, and the z-axis is set in the elevation direction as a swing direction.

The association function 1125 is a function of associating the position of an organ or the like of the subject with the position of an organ or the like included in the three-dimensional atlas image. More specifically, for example, upon acquiring the position coordinates of the characteristic portion in the atlas coordinate system and those in the biological coordinate system, the control circuitry 112 executes the association function 1125. By executing the association function 1125, the control circuitry 112 associates the characteristic portion handled in the biological coordinate system with the characteristic portion which is the same as that characteristic portion and is handled in the atlas coordinate system. This associates the magnetic field space of the position sensor system 30 with the coordinate space in the three-dimensional atlas image.

In this embodiment, after converting the position of the characteristic portion of the living body from the magnetic field coordinate system into the biological coordinate system with reference to the biological reference portion, the characteristic portion handled in the biological coordinate system is associated with the characteristic portion which is the same as that characteristic portion and is handled in the atlas coordinate system. Since the installation position of the magnetic generator 31 is different for each examination operation, the position of the living body in the magnetic field coordinate system is different for each examination operation. By introducing the biological coordinate system, for example, association with the atlas coordinate system can be performed without influence of the difference in magnetic field coordinate system in a plurality of examination operations of the same patient.

This embodiment, however, is not limited to a case in which the characteristic portion handled in the atlas coordinate system is associated with the characteristic portion of the living body via the biological coordinate system. The atlas coordinate system may be directly associated with the coordinate system of the position sensor system. That is, if the position of the characteristic portion in the magnetic field coordinate system is detected, and the position coordinates in the atlas coordinate system of the characteristic portion which is the same as that characteristic portion are acquired, the control circuitry 112 associates the characteristic portion handled in the magnetic field coordinate system with that handled in the atlas coordinate system.

The control circuitry 112 implements processing of acquiring support data desired by the operator from the internal storage circuitry 18 by executing the control program according to this embodiment. More specifically, the control circuitry 112 has a support information acquisition function 1126 by executing the control program.

The support information acquisition function 1126 is a function of acquiring support data desired by the operator from the internal storage circuitry 18. More specifically, for example, if support data is requested via the input interface 110, the control circuitry 112 executes the support information acquisition function 1126. By executing the support information acquisition function 1126, the control circuitry 112 reads out the requested support data from the internal storage circuitry 18.

Note that the image generation function 161, the atlas data processing function 1121, the position information registration function 1122, the position information control function 1123, the coordinate conversion function 1124, the association function 1125, and the support information acquisition function 1126 have been explained as modules forming the processing program according to this embodiment. The present invention, however, is not limited to this. For example, the image calculation circuitry 16 may include dedicated hardware circuitry for implementing the image generation function 161. Furthermore, the image calculation circuitry 16 may be implemented by an ASIC (Application Specific Integrated Circuit), FPGA (Field Programmable Gate Array), CPLD (Complex Programmable Logic Device), or SPLD (Simple Programmable Logic Device), which incorporates the dedicated hardware circuitry. In addition, for example, the control circuitry 112 may include dedicated hardware circuitry for implementing the atlas data processing function 1121, that for implementing the position information registration function 1122, that for implementing the position information control function 1123, that for implementing the coordinate conversion function 1124, that for implementing the association function 1125, and that for implementing the support information acquisition function 1126. The control circuitry 112 may be implemented by an ASIC (Application Specific Integrated Circuit), FPGA (Field Programmable Gate Array), CPLD (Complex Programmable Logic Device), or SPLD (Simple Programmable Logic Device), which incorporates the dedicated hardware circuitry.

FIG. 2 is a flowchart illustrating an example of the procedure of processing in which the ultrasonic diagnostic apparatus 1 according to the first embodiment associates the position of an organ or the like included in various image data generated by the three-dimensional data generation circuitry 15 with the position of an organ or the like included in the three-dimensional atlas image data. A case in which a xiphoid process is set as a biological reference portion will be exemplified below.

Note that setting a xiphoid process as a biological reference portion corresponds to setting a biological reference portion on a body surface.

Prior to ultrasonic examination of the subject P, diagnosis information is input, transmission/reception conditions are set, and conditions for collecting various ultrasonic data are set in response to an operator instruction via the input interface 110. These pieces of information are stored in the internal storage circuitry 18.

The operator defines characteristic portions commonly recognizable in the three-dimensional atlas image and the ultrasonic image. The characteristic portions indicate, for example, a characteristic organ, a characteristic organ portion, an organ boundary, the axis of an organ, a characteristic vascular portion, and a characteristic structure. More specifically, for example, the three-dimensional atlas image is displayed on the display device 50. The operator designates a plurality of characteristic portions associated with this examination operation among a plurality of characteristic portions in the three-dimensional atlas image displayed on the display device 50. The operator designates each characteristic portion by, for example, directly touching the characteristic portion displayed on the display device 50 via the touch command screen provided on the surface of the display device 50. Alternatively, the operator may designate each characteristic portion by, for example, operating the trackball or the like to set, on the characteristic portion, a cursor displayed on the display device 50, and pressing an OK button provided in the input interface 110.

If the characteristic portion is designated, the control circuitry 112 executes the atlas data processing function 1121. By executing the atlas data processing function 1121, the control circuitry 112 acquires position coordinates (xa, ya, za) of the designated characteristic portion on the three-dimensional atlas image (step S21). The control circuitry 112 stores the acquired position coordinates of the characteristic portion in the internal storage circuitry 18 as coordinate information.

Figure 3:
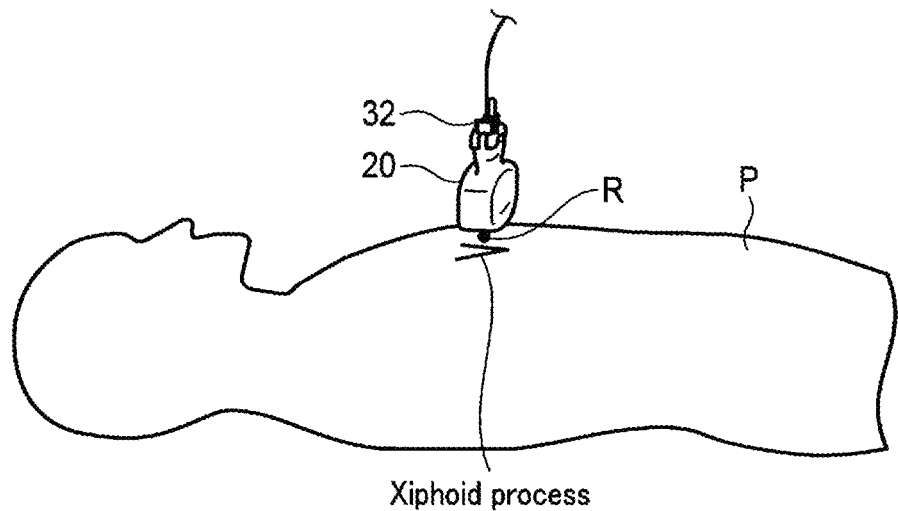
FIG. 3 is a view when an ultrasonic probe shown in FIG. 1 is brought into contact with the body surface of a subject in a vertical direction.

Subsequently, the operator registers the position information of a biological reference portion R. More specifically, for example, the operator brings the ultrasonic probe 20 into contact with the body surface of the subject P in the vertical direction so as to scan an axial surface including the xiphoid process set as the biological reference portion R. FIG. 3 is a schematic view when the ultrasonic probe 20 is brought into contact with the body surface of the subject P in the vertical direction. After bringing the ultrasonic probe 20 into contact with the subject P, the operator presses a button provided in the ultrasonic probe 20 or the operation panel 61. This inputs a designation instruction to the control circuitry 112.

Upon receiving the designation instruction, the control circuitry 112 executes the position information registration function 1122. By executing the position information registration function 1122, the control circuitry 112 acquires the position (x, y, z, θx, θy, θz) of the ultrasonic probe 20 calculated by the position detection device 33 when the designation instruction is input (step S22). The position of the ultrasonic probe 20 is, for example, the position of the position sensor 32 installed in the ultrasonic probe 20. Note that the position of the ultrasonic probe 20 may be a desired position such as the center of the ultrasonic transmission/reception surface of the ultrasonic probe 20, which is obtained by using the shape information of the ultrasonic probe 20.

If the xiphoid process is set as the biological reference portion R, an arbitrary portion in the ultrasonic tomographic image displayed on the display device 50 is not designated after the pressing of the button (NO in step S23). The control circuitry 112 registers, as the position information of the biological reference portion R, the position (x, y, z, θx, θy, θz) of the ultrasonic probe 20 acquired in step S22 (step S25).

On the other hand, the biological reference portion does not always exist on the body surface. The biological reference portion may exist, for example, in the body such as a mitral valve, portal vein bifurcation, abdominal aortic bifurcation, or the interior of an organ. In this case, after the pressing of the button, an arbitrary portion in the ultrasonic tomographic image displayed on the display device 50 is designated.

Figure 4:
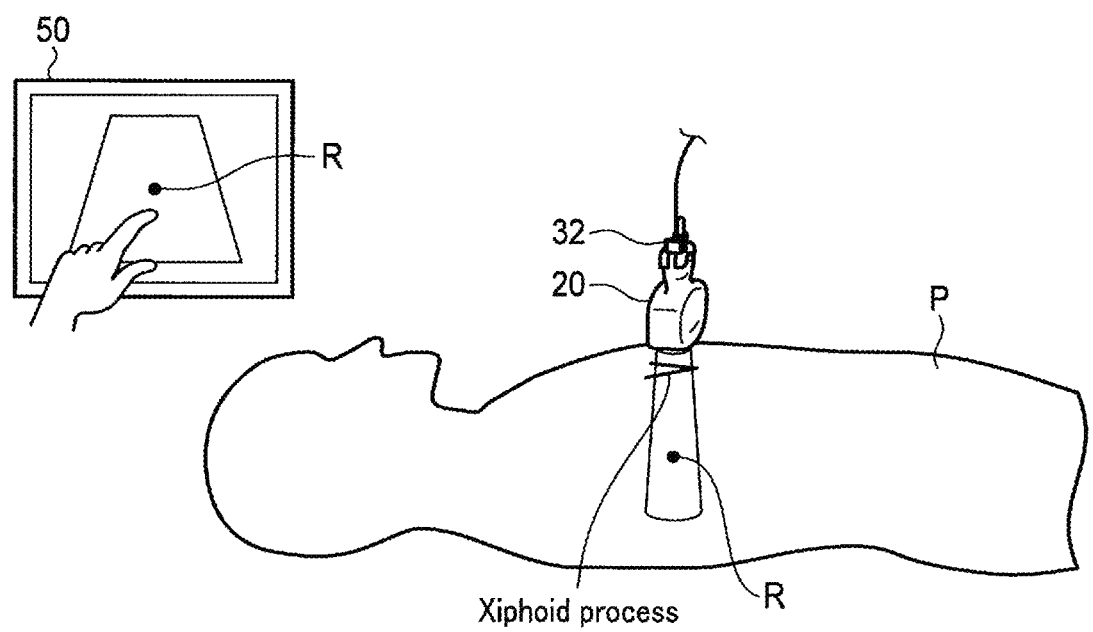
FIG. 4 is a view when a biological reference portion is designated in an ultrasonic tomographic image displayed on a display device shown in FIG. 1.

If an arbitrary portion in the ultrasonic tomographic image displayed on the display device 50 is designated after the pressing of the button (YES in step S23), the control circuitry 112 executes the position information control function 1123. By executing the position information control function 1123, the control circuitry 112 acquires the position (x, y, z, θx, θy, θz) of the ultrasonic probe 20 calculated by the position detection device 33 when the designation instruction is input, and a position (x', y'), in the ultrasonic tomographic image, of the portion designated in the ultrasonic tomographic image. FIG. 4 is a schematic view when the biological reference portion R is designated in the ultrasonic tomographic image displayed on the display device 50.

Note that FIG. 2 exemplifies a designation operation of two stages of pressing the button after the ultrasonic probe 20 is brought into contact with the subject P and then designating the reference portion R on the image. However, the reference portion R may be designated by only an operation of designating the reference portion on the image. In this case, the control circuitry 112 acquires the position information of the ultrasonic probe 20 simultaneously with designation of the reference portion on the image.

The control circuitry 112 calculates the position, in the magnetic field coordinate system of the position sensor system 30, of the portion designated in the ultrasonic tomographic image based on the position (x, y, z, θx, θy, θz) of the ultrasonic probe 20 and the position (x', y') in the ultrasonic tomographic image (step S24). The control circuitry 112 registers the calculated position as the position information of the biological reference portion R in the body (step S25).

After the position information of the biological reference portion R is registered, the operator designates characteristic portions in the subject P corresponding to the characteristic portions designated in step S21 on the three-dimensional atlas image. More specifically, for example, the operator brings the ultrasonic probe 20 into contact with the subject P so that the characteristic portions designated in step S21 are included in the ultrasonic tomographic image. If characteristic portions are included in the ultrasonic tomographic image displayed on the display device 50, the operator designates the characteristic portions included in the ultrasonic tomographic image. For example, the operator designates each characteristic portion by directly touching the characteristic portion displayed on the display device 50 via the touch command screen provided on the surface of the display device 50. Alternatively, for example, the operator may designate each characteristic portion by operating the trackball or the like to set, on the characteristic portion, the cursor displayed on the display device 50, and pressing the OK button provided in the input interface 110.

After the characteristic portions included in the ultrasonic tomographic image are designated, the control circuitry 112 executes the position information registration function 1122 and the position information control function 1123. By executing the position information control function 1123, the control circuitry 112 acquires the position (x, y, z, θx, θy, θz) of the ultrasonic probe 20 calculated by the position detection device 33 when the designation instruction is input, and the position (x', y'), in the ultrasonic tomographic image, of the portion designated in the ultrasonic tomographic image. The control circuitry 112 calculates the position, in the magnetic field coordinate system of the position sensor system 30, of the characteristic portion designated in the ultrasonic tomographic image based on the position (x, y, z, θx, θy, θz) of the ultrasonic probe 20 and the position (x', y') in the ultrasonic tomographic image. The control circuitry 112 executes the position information registration function 1122 to register the calculated position as the position information of the characteristic portion in the body (step S26).

Figure 5:
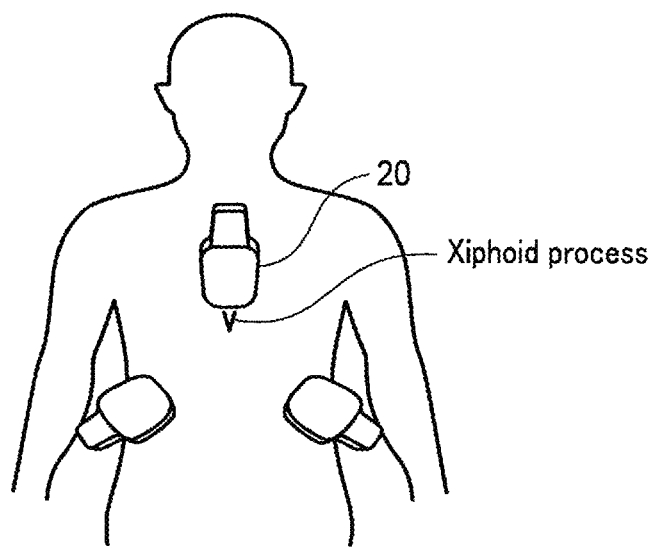
FIG. 5 is a view showing a scan of the ultrasonic probe shown in FIG. 1 on a living body surface.

The operator designates, on the ultrasonic tomographic image, characteristic portions corresponding to all the characteristic portions designated in step S21 by scanning the ultrasonic probe 20 on the living body surface of the subject P, as shown in FIG. 5. The control circuitry 112 calculates the positions of all the characteristic portions designated on the ultrasonic tomographic image, and registers the calculated positions as position information.

Figure 6:
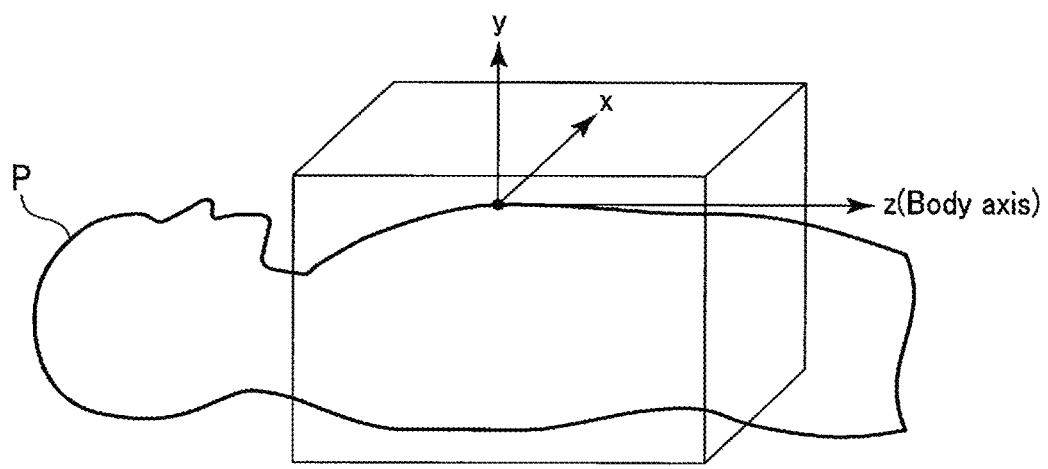
FIG. 6 is a view showing a biological coordinate system when a xiphoid process is set as a biological reference portion.
Figure 7:
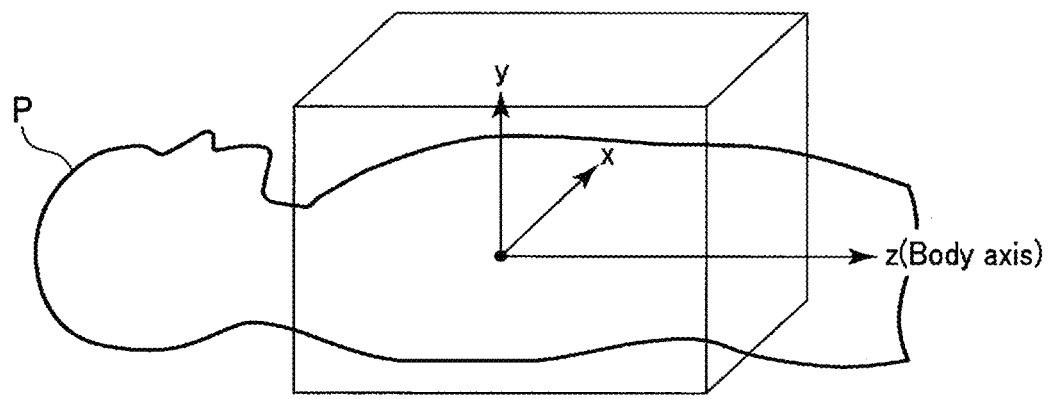
FIG. 7 is a view showing a biological coordinate system when a biological reference portion exists in a body.

After the position information of the characteristic portions in the magnetic field coordinate system of the position sensor system 30 is registered, the control circuitry 112 executes the coordinate conversion function 1124. By executing the coordinate conversion function 1124, the control circuitry 112 converts the coordinates of each characteristic portion from the magnetic field coordinate system into the biological coordinate system defined based on the position of the biological reference portion R (step S27). FIG. 6 is a view showing an example of the biological coordinate system when the xiphoid process is set as the biological reference portion R and the position information of the biological reference portion R is acquired, as shown in FIG. 3. FIG. 7 is a view showing an example of the biological coordinate system when the biological reference portion R exists in the body and the position information of the biological reference portion R is acquired, as shown in FIG. 4.

Figure 8:
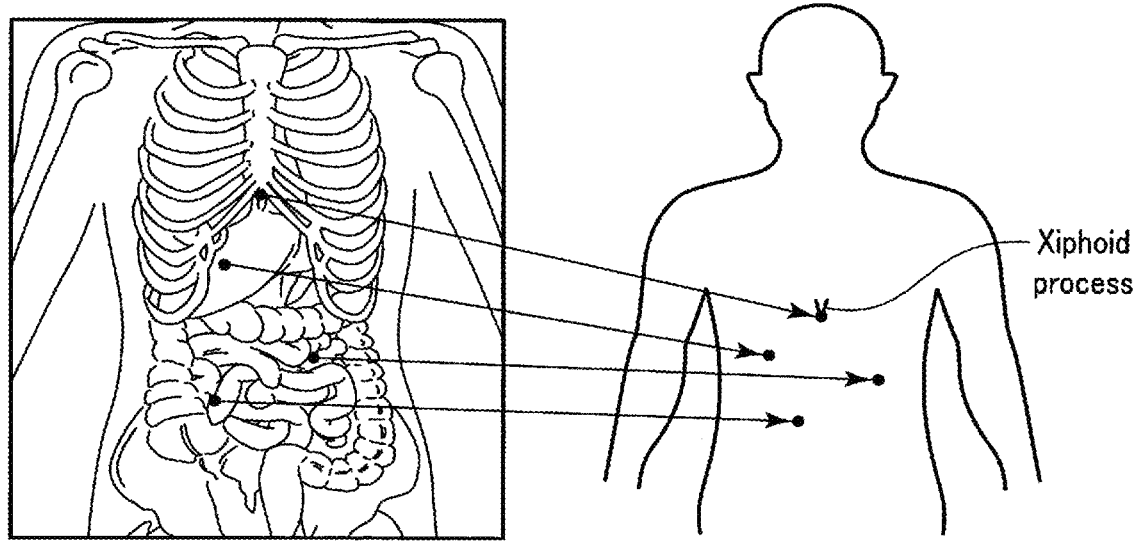
FIG. 8 is a view showing association between characteristic portions in the biological coordinate system and characteristic portions in an atlas coordinate system.

After the position coordinates of the characteristic portions in the biological coordinate system are acquired, the control circuitry 112 executes the association function 1125. By executing the association function 1125, the control circuitry 112 associates the characteristic portions in the biological coordinate system with those in the atlas coordinate system based on the position coordinates in the biological coordinate system and those in the atlas coordinate system, as shown in FIG. 8 (step S28). This associates the magnetic field space of the position sensor system 30 with the coordinate space of the three-dimensional atlas image.

The distances between the characteristic portions in the atlas image are set based on a standard body build. On the other hand, the body builds of subjects are different. Thus, the registered characteristic portions of the subject may be different from characteristic portions in the atlas image. In the processing shown in FIG. 2, the characteristic portions in the biological coordinate system are associated with those in the atlas coordinate system. Therefore, if there is a difference between the body build of the subject and the body build represented by the atlas image, the distances between the characteristic portions in the atlas image are increased or decreased based on the characteristic portions in the biological coordinate system. Alternatively, the relationship between the characteristic portions in the atlas image may be changed based on the characteristic portions in the biological coordinate system. Consequently, even if there is a difference between the body build of the subject and the body build represented by the atlas image, the ultrasonic diagnostic apparatus 1 can associate the position of an organ or the like included in the various image data generated by the three-dimensional data generation circuitry 15 with the position of an organ or the like included in the three-dimensional atlas image data. That is, with reference to atlas data, the ultrasonic diagnostic apparatus 1 can recognize a position in the subject P at which the ultrasonic probe 20 scans.

Note that the distances between the characteristic portions in the atlas image may be adjusted for the whole body or for each organ. FIG. 5 shows an example in which body build information is input based on the position information of the ultrasonic probe 20.

Furthermore, when associating the characteristic portions in the magnetic field coordinate system with those in the atlas coordinate system, if there is a difference between the body build of the subject and the body build represented by the atlas image, the distances between the characteristic portions in the atlas image are increased, decreased, or changed based on the characteristic portions in the magnetic field coordinate system. The relationship between the characteristic portions in the atlas image is changed based on the characteristic portions in the magnetic field coordinate system.

Figure 9:
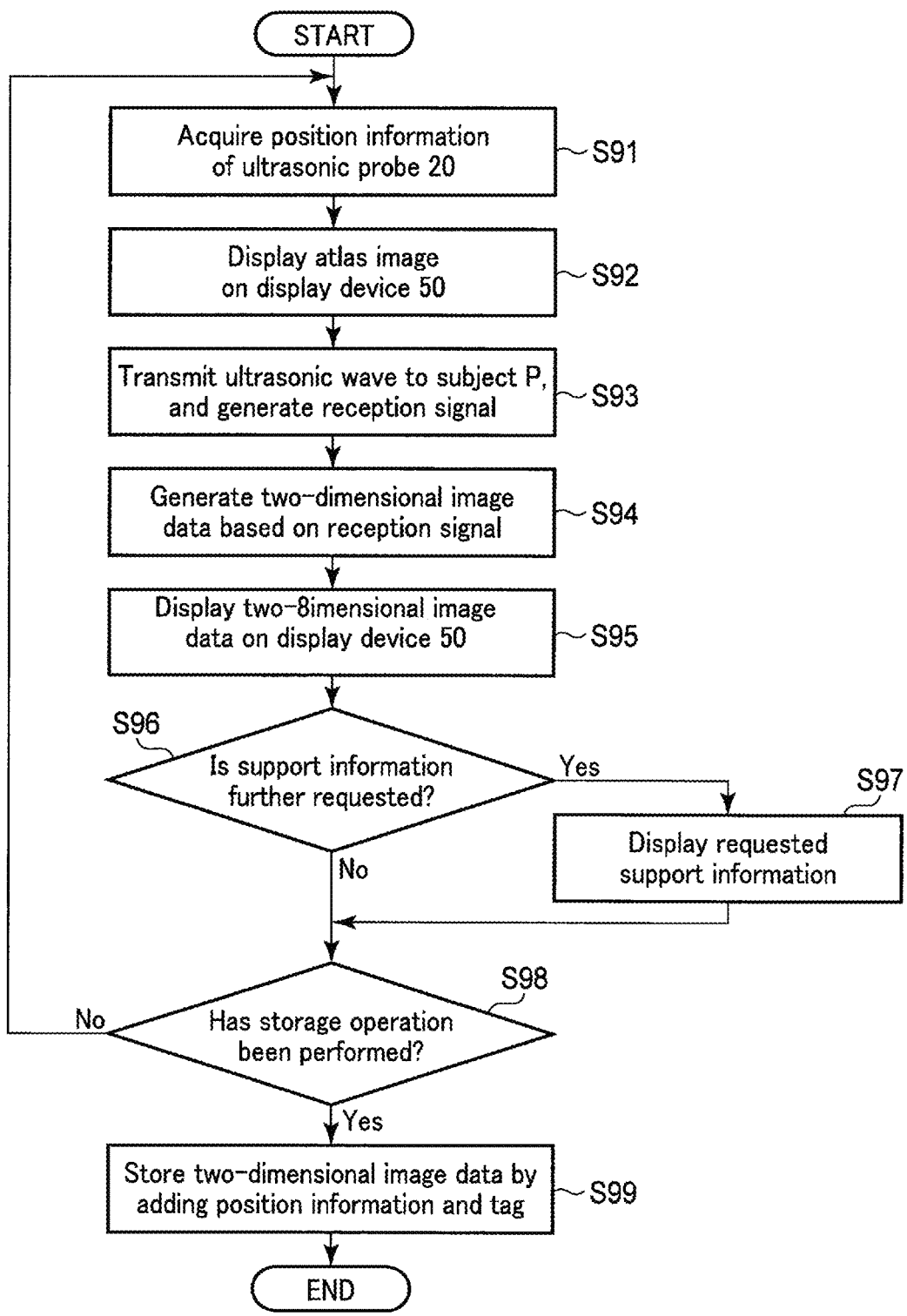
FIG. 9 is a flowchart illustrating the procedure of processing in which the ultrasonic diagnostic apparatus shown in FIG. 1 generates display image data.

FIG. 9 is a flowchart illustrating an example of the procedure of processing in which the ultrasonic diagnostic apparatus 1 according to the first embodiment generates display image data. A description of FIG. 9 assumes that the magnetic field space of the position sensor system 30 is associated with the coordinate space in the three-dimensional atlas image by the processing shown in FIG. 2. A case in which the three-dimensional data generation circuitry 15 generates two-dimensional image data will be exemplified below.

The operator performs ultrasonic examination of the subject P using the ultrasonic probe 20. The position sensor system 30 detects the position of the ultrasonic probe 20. The detected position is output to the main body device 10 as position information in the magnetic field coordinate system (step S91).

After the position of the ultrasonic probe 20 is detected, the control circuitry 112 executes the support information acquisition function 1126. By executing the support information acquisition function 1126, the control circuitry 112 reads out the three-dimensional atlas image data from the internal storage circuitry 18. The image calculation circuitry 16 executes the image generation function 161 to generate display image data from the three-dimensional atlas image.

More specifically, for example, the image calculation circuitry 16 converts the acquired position information into position coordinates in the atlas coordinate system based on the relationship between the magnetic field space and the atlas coordinate space which have been associated by the processing shown in FIG. 2. Based on the converted position coordinates, the image calculation circuitry 16 superimposes the icon (to be referred to as a virtual probe G22 hereinafter) of the ultrasonic probe on the three-dimensional atlas image. Based on, for example, ultrasonic transmission condition information and the like, the image calculation circuitry 16 creates a virtual scan area A1 imitating ultrasonic waves transmitted from the ultrasonic probe 20. The image calculation circuitry 16 superimposes the created virtual scan area A1 at the distal end of the virtual probe G22. The display processing circuitry 17 converts, into a video signal, display image data obtained by superimposing the virtual probe G22 and the virtual scan area A1 on the three-dimensional atlas image, and displays the video signal on the display device 50 (step S92).

The ultrasonic probe 20 manually, three-dimensionally scans the subject P using the plurality of ultrasonic transducers for two-dimensionally scanning the subject P. The ultrasonic waves transmitted from the ultrasonic probe 20 to the subject P are sequentially reflected by a discontinuity surface of acoustic impedance of the living tissue of the subject P, and received by the ultrasonic probe 20 as a reflected wave signal. The ultrasonic reception circuitry 12 performs various processes for the reflected wave signal received by the ultrasonic probe 20, and generates a reception signal (step S93).

The B-mode processing circuitry 13 generates B-mode RAW data on a two-dimensional ultrasonic scanning line based on the reception signal received from the ultrasonic reception circuitry 12. The three-dimensional data generation circuitry 15 generates a plurality of two-dimensional image data by executing RAW-pixel conversion for the two-dimensional B-mode RAW data generated by the B-mode processing circuitry 13 (step S94). The plurality of two-dimensional image data represent a plurality of tomographic images collected while manually moving the ultrasonic probe.

The image calculation circuitry 16 sets one of the plurality of generated two-dimensional image data as new display image data in parallel with the display image data generated in step S92. The display processing circuitry 17 converts the generated display image data into a video signal, and displays it on the display device 50 (step S95).

Figure 10:
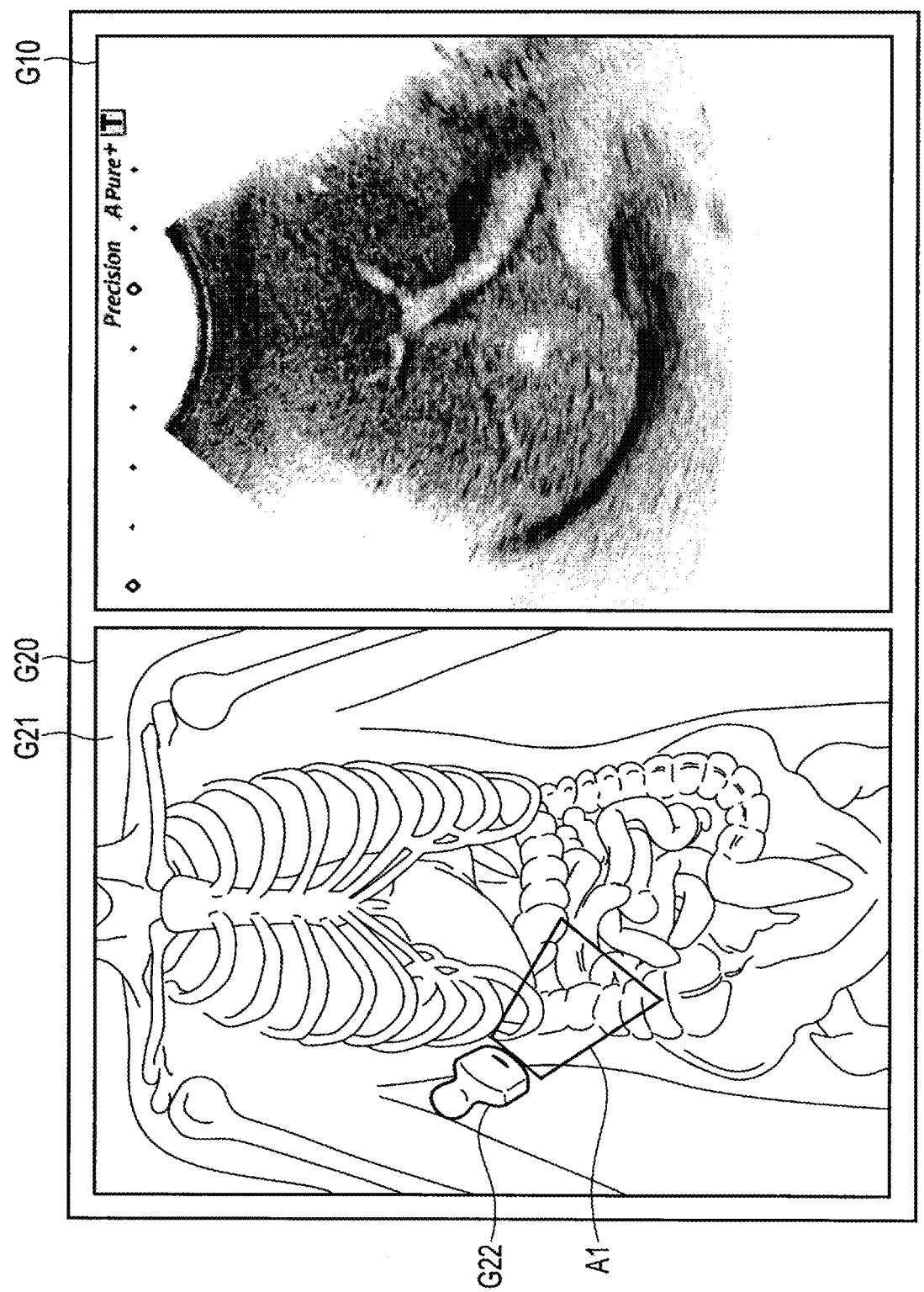
FIG. 10 is a view showing a display image in which a two-dimensional image and a three-dimensional atlas image are displayed side by side.

FIG. 10 is a view showing an example of a display image in which a two-dimensional image and a three-dimensional atlas image are displayed side by side. The display image shown in FIG. 10 includes a first display region G10 where a two-dimensional image is displayed and a second display region G20 where support data is displayed. In the example shown in FIG. 10, an ultrasonic image including a liver is displayed in the first display region G10, and a three-dimensional atlas image G21 including organs and bones in the overall image of the living body is displayed in the second display region G20. In the second display region G20 shown in FIG. 10, the virtual probe G22 is superimposed at a position corresponding to the position of the ultrasonic probe 20 in the magnetic field coordinate system. The virtual scan area A1 representing a virtual scan area is superimposed at the distal end of the virtual probe G22.

Note that FIG. 10 shows a case in which the three-dimensional atlas image of the overall image of the living body is displayed in the second display region G20. The present invention, however, is not limited to this. The atlas image displayed in the second display region G20 may be a three-dimensional atlas image representing the overall image of an organ or a two-dimensional atlas image representing a corresponding section. Alternatively, the atlas image displayed in the second display region G20 may be a three-dimensional atlas image representing blood vessels or muscles. The operator can select an atlas image to be displayed in the second display region G20, as needed. The image calculation circuitry 16 switches the display of the second display region G20 to the selected atlas image.

The operator scans the subject P while moving the ultrasonic probe 20. In synchronism with the movement of the ultrasonic probe 20 by the operator, the display position of the virtual probe G22 and the display position of the virtual scan area A1, which are displayed in the second display region G20, move.

The control circuitry 112 determines whether support data is further requested by the operator in the support information acquisition function 112b (step S96). The display image displayed on the display device 50 is provided with, for example, an input region for accepting a request from the operator. If a request is input to the input region by the operator (YES in step S96), the control circuitry 112 reads out, from the internal storage circuitry 18, the support data requested by the operator using, as search keys, a search word input to the input region and an organ name, a portion name, a vein name, and the like which are recognized based on the position of the ultrasonic probe 20. The control circuitry 112 presents a search result to the operator by displaying, on the display device 50, the support data found based on the search word and the recognized organ name and the like. The control circuitry 112 accepts selection of the presented support data. The image calculation circuitry 16 displays, in the second display region G20, an image based on the selected support data (step S97).

Figure 11:
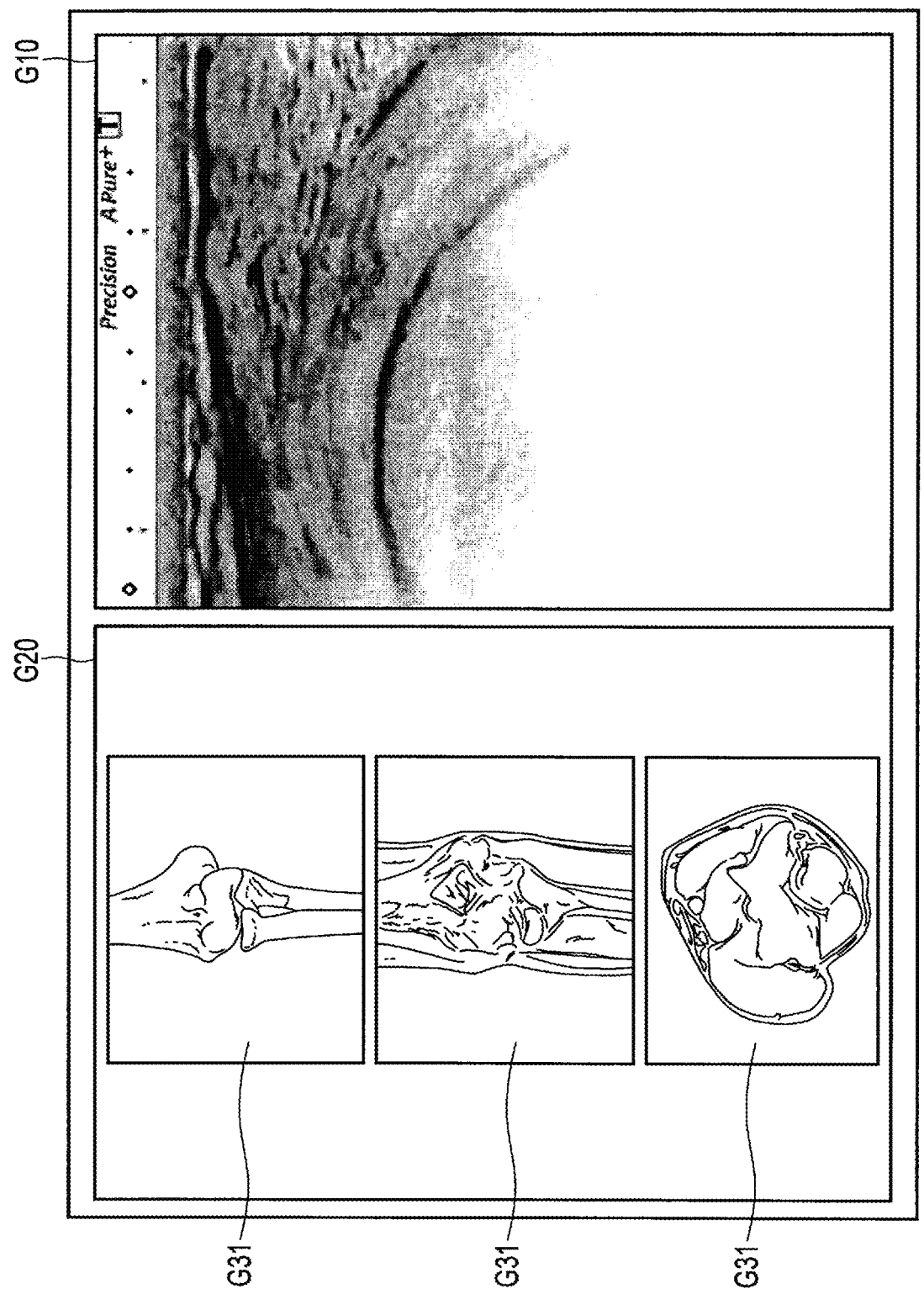
FIG. 11 is a view showing a display image in which support images each representing an organ content are displayed in the second display region.
Figure 12:
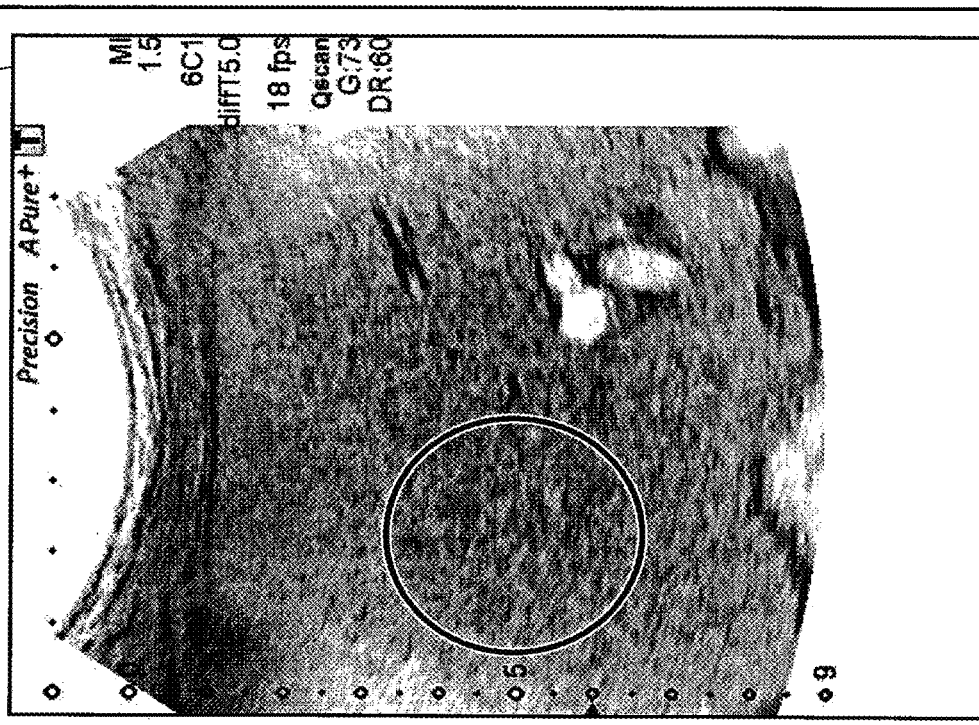
FIG. 12 is a view showing a display image in which support images each representing an organ content are displayed in the second display region.
Figure 12:
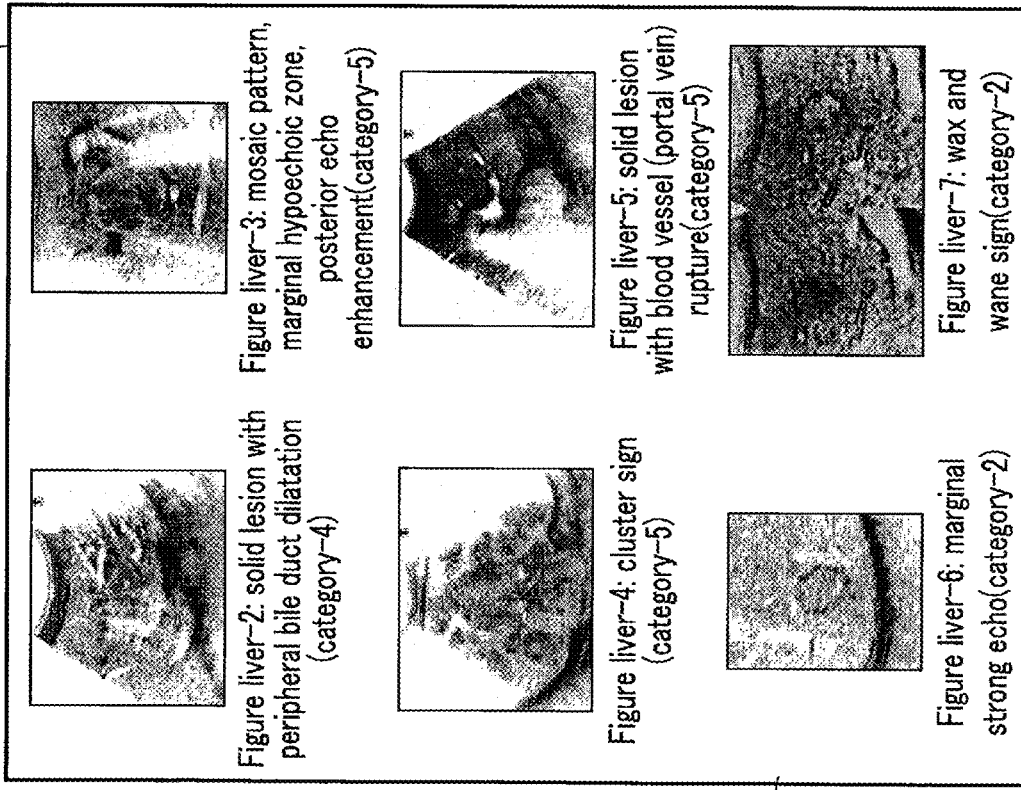

An example of the display image generated by the image calculation circuitry 16 will be described with reference to FIGS. 11, 12, 13, 14, and 15. FIGS. 11 and 12 are views each showing an example of the display image in which support images each representing an organ content are displayed in the second display region G20.

Referring to FIG. 11, an ultrasonic image related to a knee region is displayed in the first display region G10 and support images G31 are displayed in the second display region G20. In the support images G31 shown in FIG. 11, a surface rendering image with respect to an MR image related to the knee region and MPR images with respect to the MR image are displayed.

The operator who wants to display the display image shown in FIG. 11 inputs, for example, a search word "MR image" to the input region. Based on the search word and a scan of the knee region recognized based on the atlas data, the control circuitry 112 searches for necessary information from the internal storage circuitry 18 and the external apparatus 40 connected via the network 100. The control circuitry 112 reads out, for example, the electrical health record information of the subject P, and confirms based on the readout electrical health record information whether there are MR images obtained by imaging the knee of the subject P in the past. If there are MR images obtained by imaging the knee of the subject P in the past, the control circuitry 112 reads out the MR images from, for example, the database for the PACS. The image calculation circuitry 16 displays the readout MR images on the display device 50. The operator selects an image appropriate for comparison with the ultrasonic image from the MR images displayed on the display device 50. The image calculation circuitry 16 displays the selected MR image as the support image G31.

Note that if there is no MR image obtained by imaging the knee of the subject P in the past, the control circuitry 112 may read out, for example, an MR image related to a knee included in the atlas data.

Alternatively, for example, the control circuitry 112 may read out an MR image related to a knee of another patient from the database for the PACS. The image displayed in the support image G31 is not limited to the MR image. An image acquired by another medical image diagnostic apparatus may be displayed in the support image G31. This allows the scan operator to scan the ultrasonic probe 20 while collating an organ or the like included in the ultrasonic image with the image acquired by the other medical image diagnostic apparatus.

Referring to FIG. 12, an ultrasonic image related to a liver is displayed in the first display region G10, and a support image G41 is displayed in the second display region G20. Findings related to the liver are displayed in the support image G41 shown in FIG. 12.

The operator who wants to display the display image shown in FIG. 12 inputs, for example, a search word "findings" to the input region. Based on the search word and a scan of the liver recognized based on the atlas data, the control circuitry 112 searches for necessary information from the internal storage circuitry 18 and the external apparatus 40 connected via the network 100. The control circuitry 112 reads out, for example, examination findings which are included in the atlas data and complies with a liver examination guideline. The image calculation circuitry 16 displays the readout examination findings on the display device 50. The operator selects a finding appropriate for comparison with the ultrasonic image from the examination findings displayed on the display device 50. The image calculation circuitry 16 displays the selected finding as the support image G41. This allows the scan operator to scan the ultrasonic probe 20 while confirming the examination finding of the organ or the like included in the ultrasonic image. In addition, it is possible to objectively acquire a finding image independent of the operator with reference to the finding information. Note that the examination findings read out by the control circuitry 112 may be those in medical image diagnosis other than ultrasonic diagnosis.

Note that in FIG. 11, an image captured by another modality is displayed as an example of an organ content. A case in which an examination finding is displayed as an example of an organ content has been exemplified with reference to FIG. 12. The organ contents displayed in the second display region G20 are not limited to them. The organ contents displayed in the second display region G20 may include information about physiological functions, diagnosis information of a disease, and treatment information of the disease. Furthermore, electrical health record information of an organ currently scanned may be displayed. The information about physiological functions includes information about the result of non-image examination such as blood examination of the patient.

Figure 13:
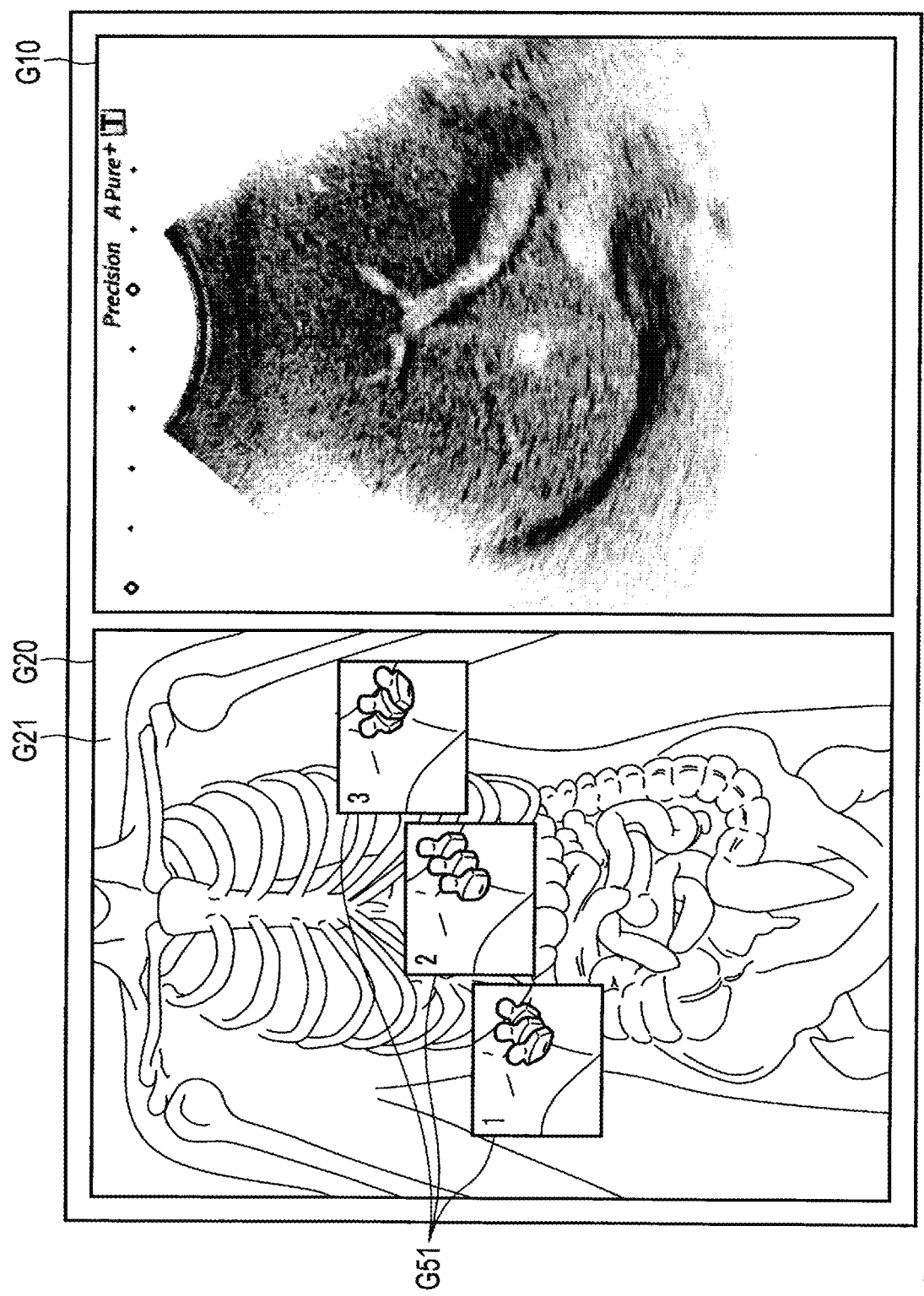
FIG. 13 is a view showing a display image in which images related to a scan method complying with the examination guideline of ultrasonic diagnosis are displayed in the second display region.

FIG. 13 is a view showing an example of the display image in which images related to a scan method complying with the examination guideline of ultrasonic diagnosis are displayed in the second display region G20. Referring to FIG. 13, an ultrasonic image related to a liver is displayed in the first display region G10, and the three-dimensional atlas image G21 and support images G51 superimposed on the three-dimensional atlas image G21 are displayed in the second display region G20. In the support images G51 shown in FIG. 13, images related to a scan method complying with the liver examination guideline are displayed. In the support images G51 shown in FIG. 13, a method of bringing the ultrasonic probe 20 into contact with the living body surface, a moving direction, and the like are displayed as a scan method.

The operator who wants to display the display image shown in FIG. 13 inputs, for example, a search word "scan method" to the input region. Based on the search word and a scan of the liver recognized based on the atlas data, the control circuitry 112 searches for necessary information from the internal storage circuitry 18 and the external apparatus 40 connected via the network 100. The control circuitry 112 reads out, for example, scan methods of the ultrasonic probe 20 complying with the liver examination guideline from the internal storage circuitry 18. The image calculation circuitry 16 displays the readout scan methods on the display device 50. The operator selects, from the scan methods displayed on the display device 50, a scan method which is considered to be reference for the current scan. The image calculation circuitry 16 displays the selected scan method as the support image G51. This generalizes ultrasonic examination know-how, thereby increasing chances of applying an ultrasonic diagnostic apparatus. It is also possible to objectively perform examination and collect images independent of the operator in accordance with a predetermined scan technique.

Note that in the example shown in FIG. 13, a method of bringing the ultrasonic probe 20 into contact with the living body surface, a moving direction, and the like are displayed in the support images G51 as a scan method. The present invention, however, is not limited to this. A region to be scanned of the organ displayed in the ultrasonic image may be displayed in the support image G51. The region to be scanned is set based on, for example, an examination fining complying with the examination guideline.

Figure 14:
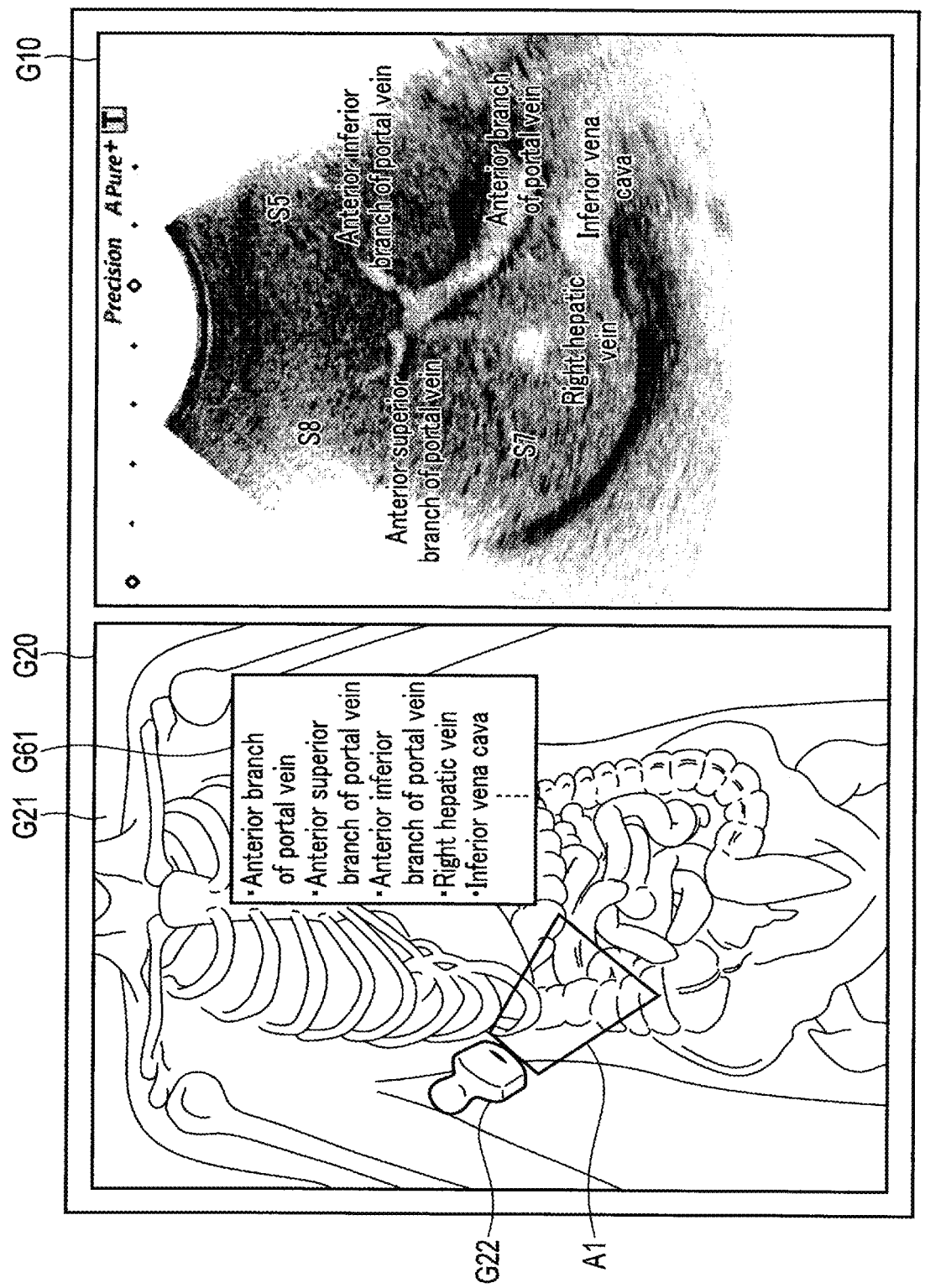
FIG. 14 is a view showing a display image in which annotations are displayed on an ultrasonic image displayed in the first display region.

FIG. 14 is a view showing an example of the display image in which annotations are superimposed and displayed on the ultrasonic image displayed in the first display region G10. For example, if the operator requests to display annotations in the display image shown in FIG. 10, the image calculation circuitry 16 adds annotations shown in FIG. 14 to a structure included in the ultrasonic image displayed in the first display region G10. The annotations shown in FIG. 14 include, for example, liver areas "S5", "S7", and "S8". The annotations shown in FIG. 14 also include, for example, "anterior branch of portal vein", "anterior superior branch of portal vein", "anterior inferior branch of portal vein", "Right hepatic vein", and "inferior vena cava" each of which represents a vascular portion. Processing of adding annotations to the ultrasonic image is performed as follows.

For example, if the operator requests to display annotations, the control circuitry 112 reads out, from the atlas data, names related to the organs, the blood vessels, and the like included in the ultrasonic image. For example, the image calculation circuitry 16 displays the readout names as a menu, as shown in a support image G61 of FIG. 14. The operator assigns the displayed names to the organs, the blood vessels, and the like included in the ultrasonic image.

Alternatively, the control circuitry 112 may automatically assign the annotations based on the standard screen. For example, the image calculation circuitry 16 displays, on the three-dimensional atlas image, the position of the ultrasonic probe 20 for imaging the standard screen. The operator scans the ultrasonic probe 20 to set the virtual probe G22 at a desired one of, for example, 15 imaging positions displayed on the three-dimensional atlas image, and acquires an ultrasonic image. Note that the standard screen includes an ultrasonic image acquired in a median position, an ultrasonic image acquired in a vertical position, and an ultrasonic image acquired in a median transverse position. The image calculation circuitry 16 assigns the name of the structure included in the standard image of the atlas data to the same structure included in the actually acquired standard image. This allows the scan operator to scan the ultrasonic probe 20 while confirming the names of the organs and the like included in the ultrasonic image. In addition, the labor for inputting annotations is significantly reduced.

The control circuitry 112 stores the examination history displayed on the three-dimensional atlas image in the internal storage circuitry 18. The examination history includes the locus of the virtual probe G22. If the operator inputs a modification instruction via the input interface 110, the control circuitry 112 modifies the examination history stored in the internal storage circuitry 18 in accordance with the modification instruction. Furthermore, if the operator inputs a determination instruction via the input interface 110, the control circuitry 112 determines the examination history stored in the internal storage circuitry 18.

Figure 15:
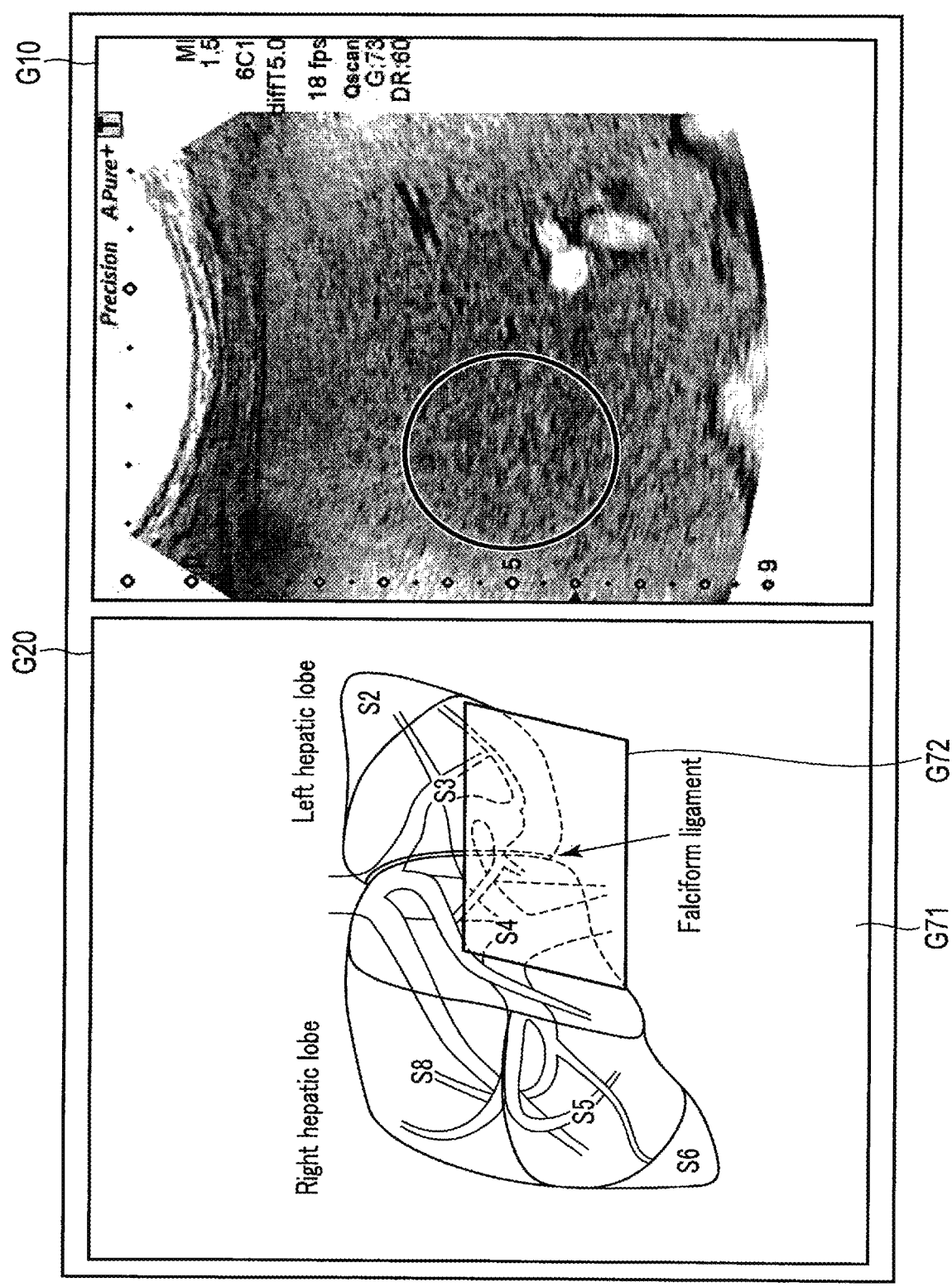
FIG. 15 is a view showing a display image in which an image based on an examination history is displayed in the second display region.

If the operator requests to display support data based on the examination history, the control circuitry 112 reads out the examination history from the internal storage circuitry 18. The image calculation circuitry 16 displays, on the display device 50, an image based on the readout examination history. FIG. 15 is a view showing an example of the display image in which the image based on the examination history is displayed in the second display region G20. Referring to FIG. 15, an ultrasonic image related to a liver is displayed in the first display region G10, and a two-dimensional atlas image G71 related to the liver and a non-scan area G72 superimposed on the two-dimensional atlas image G71 are displayed in the second display region G20. The non-scan area G72 indicates an area which has not been scanned in examination. Note that to create the more correct non-scan area G72, it is preferable to define a plurality of characteristic portions for one organ, and associate the magnetic field space with the atlas space using the plurality of characteristic portions for the organ. This improves the objectivity of ultrasonic diagnosis. It is possible to prevent oversight in examination.

Note that the image based on the examination history is not limited to the non-scan area G72. The image calculation circuitry 16 may display a scan area in the second display region G20 together with the atlas image. The image based on the examination history may be displayed in real time or displayed after examination.

Note that the support data displayed on the display device 50 may be switched to support data representing other information based on a selection instruction input by the operator via the input interface 110. For example, the image calculation circuitry 16 generates display image data to display support data designated by the operator. If the operator carefully observes the display image displayed on the display device 50 in step S95 or S97, and determines that the display image includes a desired structure, he/she performs a freeze operation via the input interface 110. Two-dimensional image data corresponding to a plurality of frames immediately before the freeze operation are saved in the image memory 19. If the operator confirms a two-dimensional image saved in the image memory 19, and determines that the saved two-dimensional image is a two-dimensional image to be stored in the internal storage circuitry 18, he/she performs a storage operation for the two-dimensional image via the input interface 110.

The control circuitry 112 determines whether a storage operation has been performed (step S98). If a storage operation has been performed (YES in step S98), the control circuitry 112 stores the two-dimensional image data having undergone storage operation in the internal storage circuitry 18 by adding position information in the magnetic field coordinate system and a tag representing the recognized organ to the data (step S99). Note that the two-dimensional image data may be added with position coordinates in the biological coordinate system after coordinate conversion and then stored, or may be added with position coordinates in the atlas coordinate system and then stored. A tag added to the two-dimensional image data is not limited to the tag representing the organ, and may be a tag representing an organ portion. The two-dimensional image data may be added with the determined examination history and then stored.

If no storage operation has been performed (NO in step S98), the control circuitry 112 cancels the freeze operation, and returns the process to step S91.

As described above, in the first embodiment, the control circuitry 112 converts the coordinates of each characteristic portion detected by the position sensor system 30 from the magnetic field coordinate system into the biological coordinate system. The control circuitry 112 associates the position of the organ or the like of the subject with the position of the organ or the like included in the three-dimensional atlas image by associating the characteristic portions represented in the biological coordinate system with those represented in the atlas coordinate system. This enables the control circuitry 112 to recognize the scan position of the ultrasonic probe 20 in the coordinate space in the atlas image.

Furthermore, in the first embodiment, the image calculation circuitry 16 displays, on the display device 50, support information based on the internal structure of the subject P which is grasped from the coordinate space in the atlas image. Since there are many organs in the body, the scan operator cannot decide, in some cases, a specific position on the living body surface with which the ultrasonic probe is brought into contact and a specific direction in the body in which the ultrasonic probe is moved in order to appropriately acquire an image of an organ to be diagnosed. In addition, depending on a displayed image, it may be difficult for the scan operator to identify an organ in the image. The ultrasonic diagnostic apparatus 1 according to the first embodiment can present, to the scan operator, support information corresponding to a portion scanned by the ultrasonic probe 20 in ultrasonic examination.

Therefore, the ultrasonic diagnostic apparatus 1 according to the first embodiment can support a scan using the ultrasonic probe.

In the first embodiment, for example, as indicated in step S99 of FIG. 9, the image data added with the position information in the magnetic field coordinate system and the tag representing the recognized organ is stored in the internal storage circuitry 18. This allows a medical facility such as a hospital to collect ultrasonic images together with scanned organ positions. The medical facility can also manage the ultrasonic images by classifying them by tags. For example, if a large number of ultrasonic images classified by tags are managed by a database or the like, it is possible to extract only necessary ultrasonic images based on a predetermined characteristic. For example, it is possible to extract ultrasonic images related to "pancreas", and confirm typical ultrasonic images related to the pancreas. Therefore, it is possible to objectively perform examination and collect images independent of the operator. Furthermore, the labor for diagnosis is reduced after examination.

In the first embodiment, the image data is added with an examination history, and stored in the internal storage circuitry 18. This allows the medical facility to collect ultrasonic images together with a scanning locus. This type of image data may be used for big data analysis using a scanning locus.

(Another Example of First Embodiment)

In the first embodiment, the control circuitry 112 converts the coordinates of each characteristic portion detected by the position sensor system 30 from the magnetic field coordinate system into the biological coordinate system. The control circuitry 112 associates the magnetic field space of the position sensor system 30 with the coordinate space in the three-dimensional atlas image by associating the characteristic portions represented in the biological coordinate system with those represented in the atlas coordinate system. In another example, the magnetic field space of the position sensor system 30 may be associated with the coordinate space in the three-dimensional atlas image via three-dimensional medical image data such as three-dimensional MR image data or three-dimensional CT image data.

Figure 16:
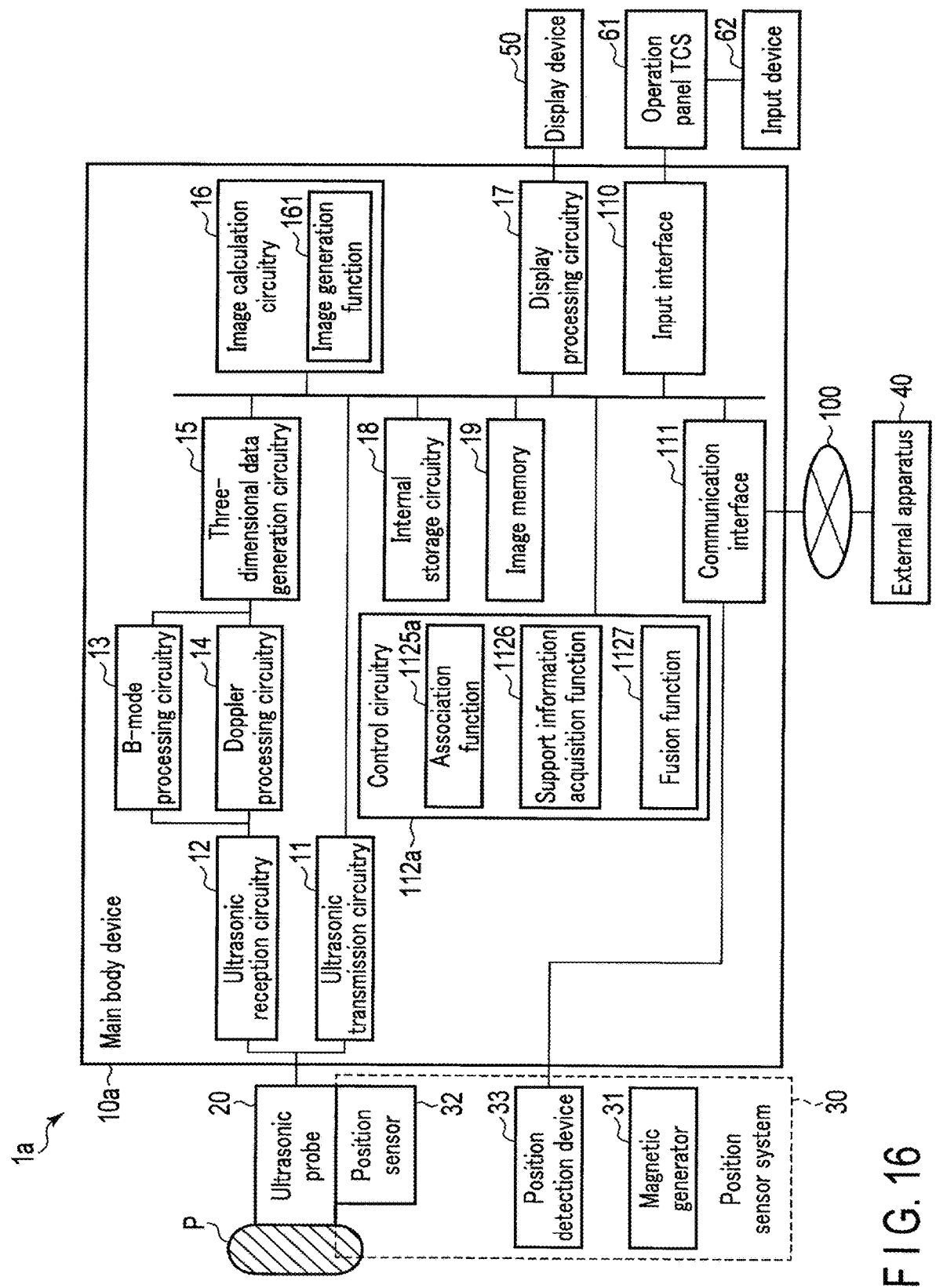
FIG. 16 is a block diagram showing another example of the arrangement of the ultrasonic diagnostic apparatus shown in FIG. 1.

FIG. 16 is a block diagram showing an example of the arrangement of an ultrasonic diagnostic apparatus 1a according to the other example. As shown in FIG. 16, the ultrasonic diagnostic apparatus 1a includes a main body device 10a, an ultrasonic probe 20, and a position sensor system 30. The main body device 10a is connected to the external apparatus 40 via the network 100. The main body device 10a is connected to the display device 50. The main body device 10a shown in FIG. 16 is an apparatus which generates an ultrasonic image based on a reflected wave signal received by the ultrasonic probe 20. As shown in FIG. 16, the main body device 10a includes ultrasonic transmission circuitry 11, ultrasonic reception circuitry 12, B-mode processing circuitry 13, Doppler processing circuitry 14, three-dimensional data generation circuitry 15, image calculation circuitry 16, display processing circuitry 17, internal storage circuitry 18, an image memory 19, an input interface 110, a communication interface 111, and control circuitry 112a.

The control circuitry 112a is a processor which serves as a center function of the ultrasonic diagnostic apparatus 1a. The control circuitry 112a executes a control program stored in the internal storage circuitry 18, thereby implementing a function corresponding to the program. More specifically, the control circuitry 112a implements processing of associating the position of an organ or the like of a subject with the position of an organ or the like included in a three-dimensional atlas image by executing the control program according to this embodiment. That is, by executing the control program, the control circuitry 112a has an association function 1125a and a fusion function 1127.

The association function 1125a is a function of associating the position of an organ or the like included in a three-dimensional MR image or a three-dimensional CT image with the position of an organ or the like included in the three-dimensional atlas image. More specifically, for example, if association is requested via the input interface 110, the control circuitry 112a executes the association function 1125a. By executing the association function 1125a, the control circuitry 112a associates characteristic portions included in the three-dimensional MR image data or the three-dimensional CT image data with those included in the three-dimensional atlas image data using, for example, a landmark-based alignment algorithm by inter-image alignment.

The fusion function 1127 is a function of associating the three-dimensional MR image data or the three-dimensional CT image data with the ultrasonic image. More specifically, for example, upon completion of association of the characteristic portions included in the three-dimensional MR image data or the three-dimensional CT image data with those included in the three-dimensional atlas image data, the control circuitry 112a executes the fusion function 1127. By executing the fusion function 1127, the control circuitry 112a associates the three-dimensional MR image data with the position of the ultrasonic image and the position of the ultrasonic probe 20. Alternatively, the control circuitry 112a associates the three-dimensional CT image data with the position of the ultrasonic image and the position of the ultrasonic probe 20.

FIG. 17 is a flowchart illustrating an example of the procedure of processing in which the ultrasonic diagnostic apparatus 1a according to the other example associates the position of an organ or the like included in various image data generated by the three-dimensional data generation circuitry 15 with the position of an organ or the like included in the three-dimensional atlas image data.

Prior to ultrasonic examination of the subject P, diagnosis information is input, transmission/reception conditions are set, and conditions for collecting various ultrasonic data are set in response to an operator instruction via the input interface 110. These pieces of information are stored in the internal storage circuitry 18.

The control circuitry 112a accepts a request to associate the position of the organ or the like included in the various image data generated by the three-dimensional data generation circuitry 15 with the position of the organ or the like included in the three-dimensional atlas image data. The operator inputs the request to perform association from, for example, the input interface 110.

After the operator requests, via the input interface 110, to perform association, the control circuitry 112a executes the association function 1125a. By executing the association function 1125a, the control circuitry 112a reads out the three-dimensional MR image data or the three-dimensional CT image data from the internal storage circuitry 18. The control circuitry 112a reads out the three-dimensional atlas image data from the internal storage circuitry 18. The control circuitry 112a associates characteristic portions included in the three-dimensional MR image data or the three-dimensional CT image data with those included in the three-dimensional atlas image data using the landmark-based alignment algorithm (step S171).

After the characteristic portions included in the three-dimensional MR image data or the three-dimensional CT image data are associated with those included in the three-dimensional atlas image data, the control circuitry 112a executes the fusion function 1127. By executing the fusion function 1127, the control circuitry 112a associates the three-dimensional MR image data with the position of the ultrasonic image and the position of the ultrasonic probe 20 based on the position information of the ultrasonic probe 20 acquired by the position sensor system 30. Alternatively, the control circuitry 112a associates the three-dimensional CT image data with the position of the ultrasonic image and the position of the ultrasonic probe 20 based on the position information of the ultrasonic probe 20 acquired by the position sensor system 30 (step S172).

Figure 18:
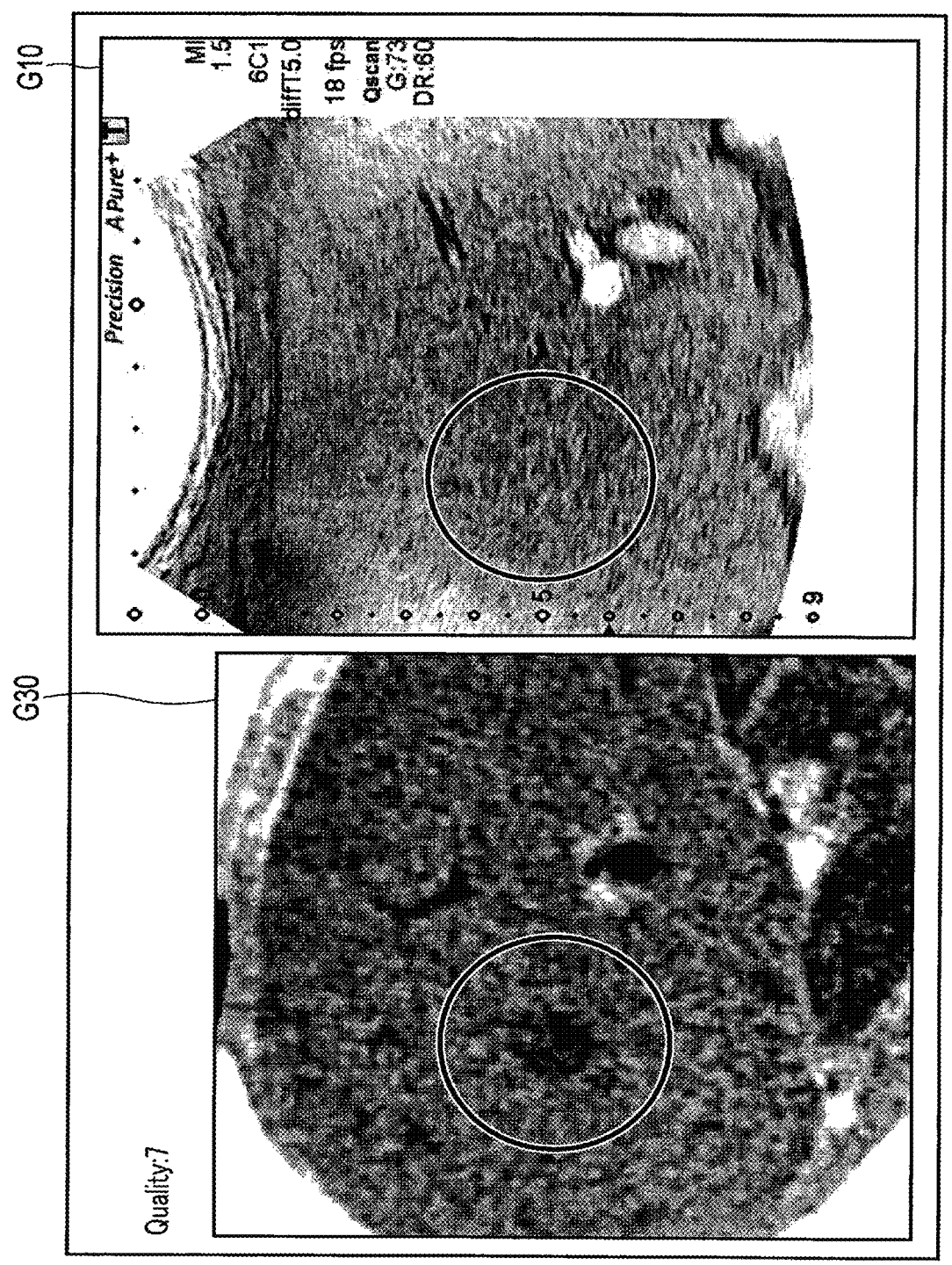
FIG. 18 is a view showing a display image in which the sectional position of a three-dimensional CT image is associated with the scan position of the ultrasonic probe and an ultrasonic tomographic image by a fusion function.

FIG. 18 is a view showing an example of a display image in which the sectional position of a three-dimensional CT image is associated with the scan position of the ultrasonic probe 20 and an ultrasonic tomographic image by the fusion function 1127. Referring to FIG. 18, an ultrasonic image related to a liver is displayed in the first display region G10, and an MPR image representing a section corresponding to the ultrasonic image is displayed in a third display region G30. This associates the magnetic field space of the position sensor system 30 with the coordinate space in the three-dimensional atlas image via the three-dimensional medical image data.

As described above, in this example, the control circuitry 112a associates the position of the organ or the like included in the three-dimensional MR image or the three-dimensional CT image with the position of the organ or the like included in the three-dimensional atlas image. The control circuitry 112*a* then associates the three-dimensional MR image data or the three-dimensional CT image data with the ultrasonic image by the fusion function. This associates the position of the organ or the like of the subject with the position of the organ or the like included in the three-dimensional atlas image. That is, the control circuitry 112*a* can recognize the scan position of the ultrasonic probe 20 in the coordinate space in the atlas image.

In this example, the image calculation circuitry 16 displays, on the display device 50, support information based on the internal structure of the subject P which is grasped from the coordinate space in the atlas image. This enables the ultrasonic diagnostic apparatus 1*a* to present, to the scan operator, support information corresponding to a portion scanned by the ultrasonic probe 20 in ultrasonic examination.

Note that the first embodiment has exemplified, for example, a case in which the control circuitry 112 acquires support data based on an input from the operator, as described in step S97 of FIG. 9. The present invention, however, is not limited to this. The control circuitry 112 or 112*a* may specify an organ included in an ultrasonic image based on atlas coordinates, and automatically read out support data corresponding to the specified organ or the like from the internal storage circuitry 18.

Figure 19:
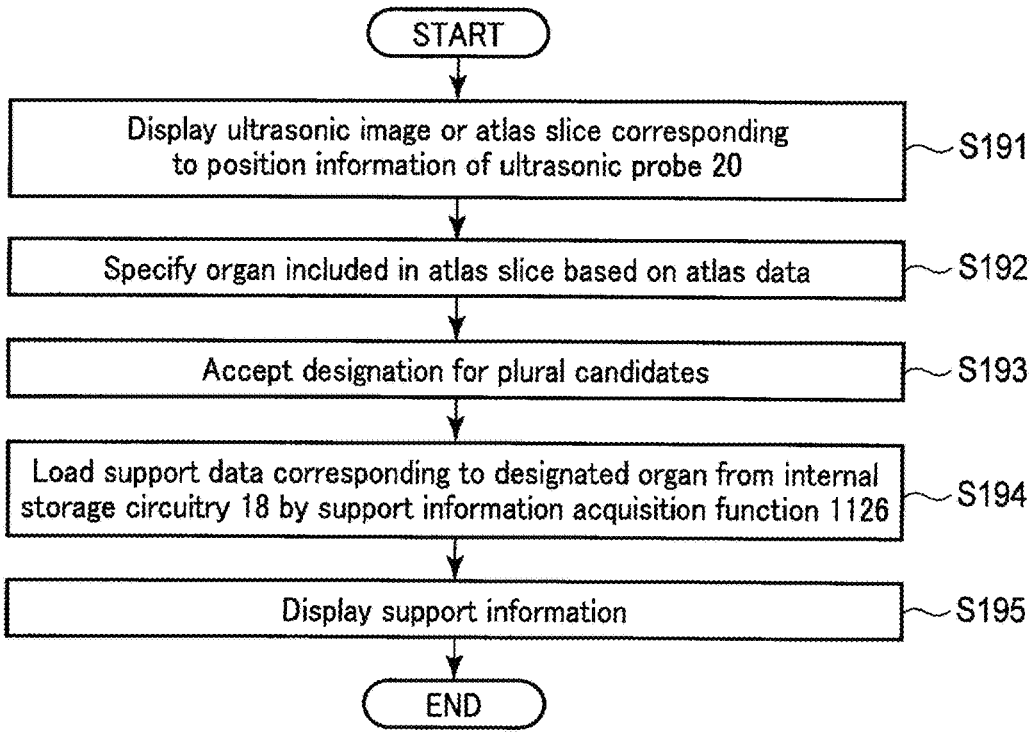
FIG. 19 is a flowchart when control circuitry shown in FIG. 1 or 16 automatically reads out support data.

FIG. 19 is a flowchart when the control circuitry 112 or 112*a* automatically reads out support data. An ultrasonic image or a three-dimensional atlas image corresponding to the position of the ultrasonic probe 20 is displayed in, for example, the second display region G20 of the display device 50 (step S191). Note that the three-dimensional atlas image may represent a section.

After the three-dimensional atlas image is displayed, the control circuitry 112 or 112*a* executes the support information acquisition function 1126. By executing the support information acquisition function 1126, the control circuitry 112 or 112*a* acquires coordinate information of the displayed three-dimensional atlas image in the atlas coordinate system. The control circuitry 112 or 112*a* specifies an organ and/or biological structure included in the three-dimensional atlas image based on the acquired coordinate information (step S192).

The control circuitry 112 or 112*a* displays the specified organ and/or biological structure on the display device 50, and accepts, from the operator, designation for candidates of an organ or biological structure for which support data is requested (step S193). For example, one of a plurality of organs and/or biological structures specified on the atlas image is designated via the input device 62. At this time, the operator sets, on the specified organ/or biological structure, a cursor displayed on the display device 50. Alternatively, a list of the specified organs and/or biological structures may be displayed on the display device 50, and selection from the list by the operator may be accepted. Note that if the control circuitry 112 or 112*a* specifies one organ or biological structure, designation need not be accepted from the operator. That is, the processing in step S193 may be skipped.

After the organ and/or biological structure included in the three-dimensional atlas image is designated, the control circuitry 112 or 112*a* reads out, from the internal storage circuitry 18, support data related to the designated organ and/or biological structure (step S194). The control circuitry 112 or 112*a* displays the readout support data on the display device 50 (step S195). Note that a case in which by executing the support information acquisition function 1126, the control circuitry 112 or 112*a* acquires coordinate information of the three-dimensional atlas image in the atlas coordinate system, and specifies an organ and/or biological structure included in the three-dimensional atlas image based on the acquired coordinate information has been exemplified. The present invention, however, is not limited to this. By executing the control program, the control circuitry 112 or 112*a* may implement a structure specifying function of acquiring the coordinate information of the three-dimensional atlas image in the atlas coordinate system, and specifying an organ and/or biological structure included in the three-dimensional atlas image based on the acquired coordinate information.

Furthermore, the ultrasonic diagnostic apparatus 1 or 1*a* according to the above embodiment may automatically change the transmission/reception conditions in accordance with an organ to be recognized. For example, a vascular flow is slow in a kidney and is fast in a heart. For example, if the organ to be recognized is a kidney, the control circuitry 112 or 112*a* sets a narrow velocity range at the time of color Doppler processing. If the organ to be recognized is a heart, the control circuitry 112 or 112*a* sets a wide velocity range at the time of color Doppler processing.

Figure 20:
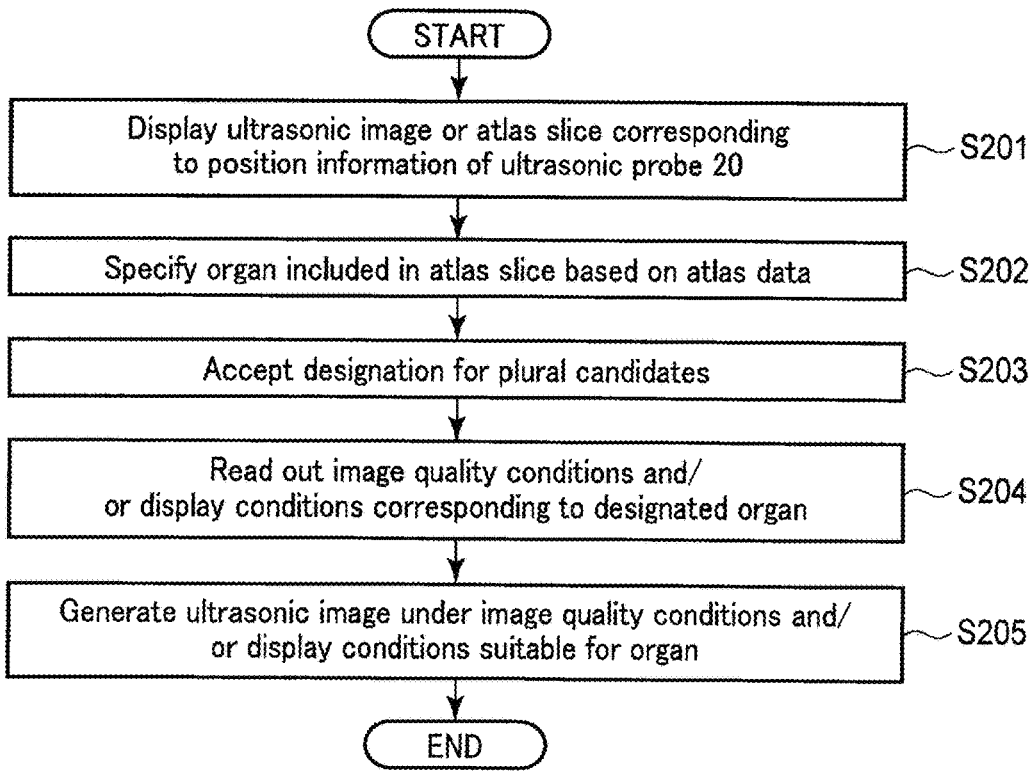
FIG. 20 is a flowchart when the control circuitry shown in FIG. 1 or 16 automatically changes transmission/reception conditions in accordance with an organ to be recognized.

FIG. 20 is a flowchart when the control circuitry 112 or 112*a* automatically changes the transmission/reception conditions in accordance with the organ to be recognized. An ultrasonic image or a three-dimensional atlas image corresponding to the position of the ultrasonic probe 20 is displayed in, for example, the second display region G20 of the display device 50 (step S201).

After the three-dimensional atlas image is displayed, the control circuitry 112 or 112*a* executes the support information acquisition function 1126. By executing the support information acquisition function 1126, the control circuitry 112 or 112*a* acquires the coordinate information of the displayed three-dimensional atlas image in the atlas coordinate system. The control circuitry 112 or 112*a* specifies an organ and/or biological structure included in the three-dimensional atlas image based on the acquired coordinate information (step S202).

The control circuitry 112 or 112*a* displays the specified organ and/or biological structure on the display device 50, and accepts, from the operator, designation for candidates of an organ or biological structure for which support data is requested (step S203). For example, one of a plurality of organs and/or biological structures specified on the atlas image is designated via the input device 62. Note that if the control circuitry 112 or 112*a* specifies one organ or biological structure, designation need not be accepted from the operator. That is, the processing in step S203 may be skipped.

After the organ and/or biological structure included in the three-dimensional atlas image is designated, the control circuitry 112 or 112*a* reads out, from the internal storage circuitry 18, image quality conditions and/or display conditions related to the designated organ and/or biological structure (step S204). The control circuitry 112 or 112*a* sets the readout image quality conditions and/or display conditions (step S205). The ultrasonic diagnostic apparatus 1 or 1*a* transmits/receives ultrasonic waves under the set image quality conditions and/or display conditions, thereby generating an ultrasonic image.

The above embodiment has exemplified a case in which the image calculation circuitry 16 displays support data in real time in parallel with an ultrasonic image in synchronism with the scan of the ultrasonic probe 20. The present invention, however, is not limited to this. The image calculation circuitry 16 may generate display image data based on stored image data after examination. In this case, for example, the control circuitry 112 or 112a reads out image data after examination, and recognizes, based on position information added to the image data, the position of the ultrasonic probe 20 at the time of acquiring the readout image data. The control circuitry 112 or 112a acquires position coordinates in the atlas coordinate system corresponding to the recognized position information, and recognizes an organ or the like included in the image data. The control circuitry 112 or 112a reads out support data corresponding to the recognized organ or the like from the internal storage circuitry 18. The image calculation circuitry 16 generates display image data from the image data and the readout support data. This can improve the objectivity of ultrasonic diagnosis while improving efficiency of consultation.

If the operator designates a predetermined position on the atlas image, the image calculation circuitry 16 according to the above embodiment may display, on the display device 50, an ultrasonic image acquired in a region at almost the same position as the designated position.

Figure 21:
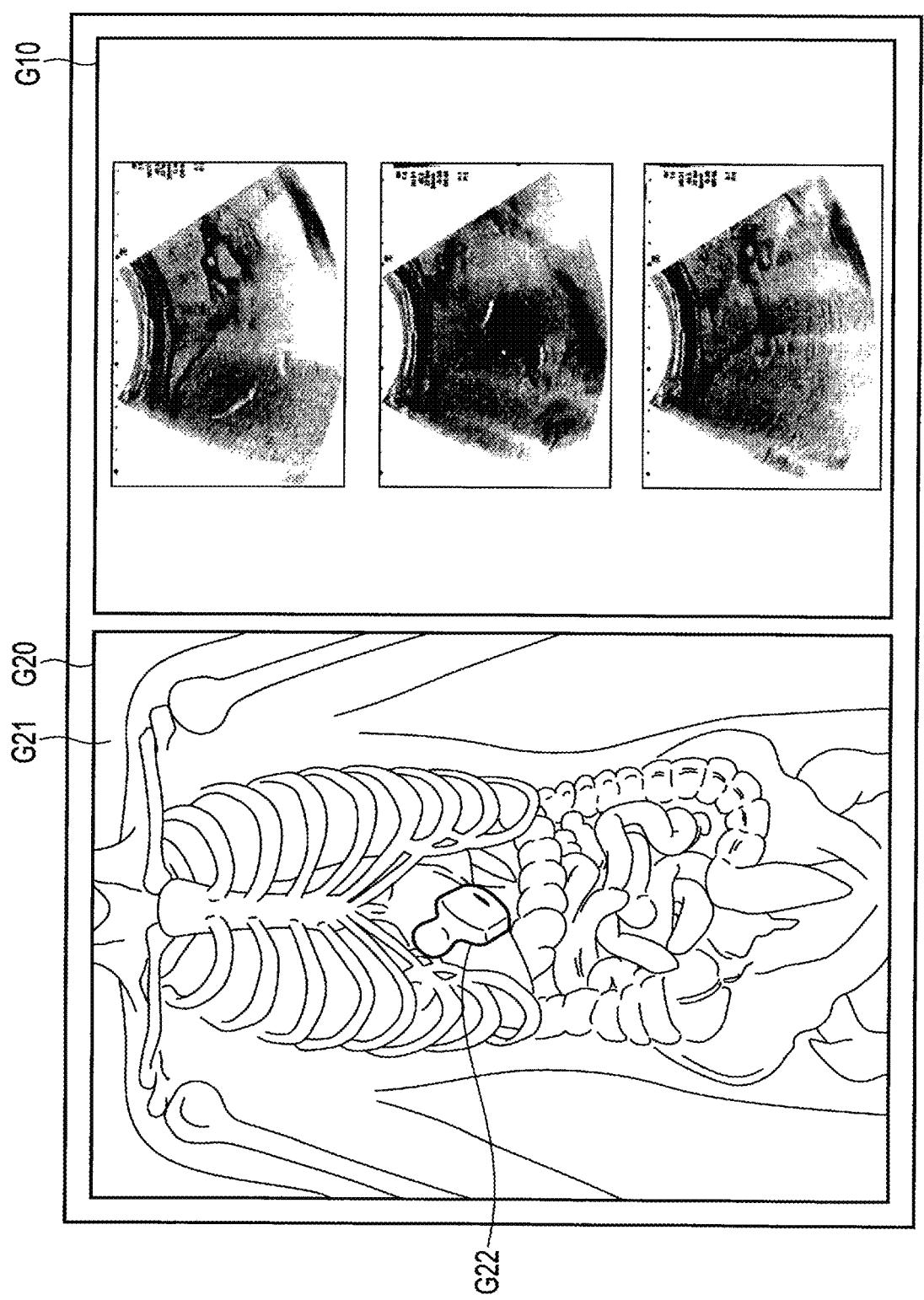
FIG. 21 is a view showing a display image when an atlas image and a plurality of ultrasonic images corresponding to a position designated in the atlas image are displayed.

FIG. 21 is a view showing an example when the atlas image G21 and a plurality of ultrasonic images corresponding to a position designated in the atlas image G21 are displayed. As shown in FIG. 21, the operator moves, onto a desired organ, the virtual probe G22 on the atlas image. If the virtual probe is moved, the control circuitry 112 or 112a executes the support information acquisition function 1126.

By executing the support information acquisition function 1126, the control circuitry 112 or 112a specifies a range in the magnetic field coordinate system corresponding to the position range of the organ in the atlas coordinate system. The control circuitry 112 or 112a reads out, from the internal storage circuitry 18, ultrasonic images included in the specified range in the magnetic field coordinate system, and displays them on the display device 50. At this time, the ultrasonic images associated with the atlas image are stored in the internal storage circuitry 18. Note that the displayed ultrasonic images may be two-, three-, or four-dimensional ultrasonic images. Alternatively, the displayed ultrasonic images may be MPR images or VR images.

Second Embodiment

The first embodiment has explained the ultrasonic diagnostic apparatus capable of supporting a scan using the ultrasonic probe by associating the magnetic field space of the position sensor system with the coordinate space in the three-dimensional atlas image. The second embodiment will describe an ultrasonic diagnostic apparatus capable of improving the objectivity of ultrasonic diagnosis by generating map display image data for displaying image data from a bird's eye view in a three-dimensional space of a biological coordinate system.

FIG. 22 is a block diagram showing an example of the arrangement of an ultrasonic diagnostic apparatus 1b according to the second embodiment. As shown in FIG. 22, the ultrasonic diagnostic apparatus 1b includes a main body device 10b, an ultrasonic probe 20, and a position sensor system 30. The main body device 10b is connected to an external apparatus 40 via a network 100. The main body device 10b is also connected to a display device 50.

The main body device 10b shown in FIG. 22 is an apparatus which generates an ultrasonic image based on a reflected wave signal received by the ultrasonic probe 20. As shown in FIG. 22, the main body device 10b includes ultrasonic transmission circuitry 11, ultrasonic reception circuitry 12, B-mode processing circuitry 13, Doppler processing circuitry 14, an operation panel 61, an input device 62, three-dimensional data generation circuitry 15, image calculation circuitry 16b, display processing circuitry 17, internal storage circuitry 18, an image memory 19, an input interface 110, a communication interface 111, and control circuitry 112b.

The image calculation circuitry 16b is a processor which generates map display image data for displaying various image data from a bird's eye view in the three-dimensional space of the biological coordinate system based on various image data generated by the three-dimensional data generation circuitry 15. The image calculation circuitry 16b executes an image processing program stored in the internal storage circuitry 18, thereby implementing a function corresponding to the program.

More specifically, the image calculation circuitry 16b generates map display image data for displaying two-dimensional image data from a bird's eye view in the three-dimensional space of the biological coordinate system based on two-dimensional image data generated by the three-dimensional data generation circuitry 15. The image calculation circuitry 16b also generates map display image data for displaying rendering image data from a bird's eye view in the three-dimensional space of the biological coordinate system based on rendering image data (MPR image and VR image) generated by the three-dimensional data generation circuitry 15.

The image calculation circuitry 16b generates map display image data for displaying M-mode image data from a bird's eye view in the three-dimensional space of the biological coordinate system based on M-mode image data added with position information by the three-dimensional data generation circuitry 15. The image calculation circuitry 16b generates map display image data for displaying spectrum Doppler image data from a bird's eye view in the three-dimensional space of the biological coordinate system based on spectrum Doppler image data added with position information by the three-dimensional data generation circuitry 15. The image calculation circuitry 16b generates map display image data for displaying, from a bird's eye view, image quality conditions and scan mode information at the time of a scan, a measurement image and measurement result, and application information and an image, which have been added with position information by the three-dimensional data generation circuitry 15.

Note that the map display image data generated by the image calculation circuitry 16b include the image data itself or predetermined information based on the image data. The map display image data generated by the image calculation circuitry 16b is stored in the internal storage circuitry 18.

The control circuitry 112b is a processor which serves as a center function of the ultrasonic diagnostic apparatus 1b. The control circuitry 112b executes a control program stored in the internal storage circuitry 18, thereby implementing a function corresponding to the program. For example, the control circuitry 112b has a function of storing the position information of a biological reference portion in the internal storage circuitry 18, that is, a registration function of registering the position information of a biological reference portion.

The image calculation circuitry 16b shown in FIG. 22 executes the image processing program according to this embodiment, thereby implementing processing of generating map display image data for displaying the various image data generated by the three-dimensional data generation circuitry 15 from a bird's eye view in the three-dimensional space of the biological coordinate system. More specifically, by executing the image processing program, the image calculation circuitry 16b has a reference portion control function 162, a coordinate conversion function 163, and an image generation function 161b.

The reference portion control function 162 is a function of calculating the position of a biological reference portion designated via an ultrasonic tomographic image. More specifically, upon receiving, from the operator, designation of a biological reference portion in the ultrasonic tomographic image displayed on the display device 50, the image calculation circuitry 16b executes the reference portion control function 162. By executing the reference portion control function 162, the image calculation circuitry 16b calculates the position of the biological reference portion in the magnetic field coordinate system of the position sensor system 30 based on the position of the ultrasonic probe 20 at the time of acquiring the ultrasonic tomographic image and the position designated in the ultrasonic tomographic image.

The coordinate conversion function 163 is a function of converting the coordinates of the position information added to the image data from the magnetic field coordinate system into a biological coordinate system defined based on the position of the biological reference portion. More specifically, for example, after predetermined image data is selected, the image calculation circuitry 16b executes the coordinate conversion function 163. By executing the coordinate conversion function 163, the image calculation circuitry 16b causes the three-dimensional data generation circuitry 15 to convert, for example, the coordinates of the position information added to the two-dimensional image data, rendering image data, M-mode image data, or spectrum Doppler image data from the magnetic field coordinate system into the biological coordinate system. The image calculation circuitry 16b defines the biological coordinate system based on the position (x, y, z, θx, θy, θz) of the biological reference portion. For example, the biological coordinate system is defined so that the position coordinate point (x, y, z) is set as an origin and, based on the rotation angles (θx, θy, θz), the x-axis is set in the azimuth direction as a scan direction, the y-axis is set in the depth direction, and the z-axis is set in the elevation direction as a swing direction.

The image generation function 161b is a function of generating map display image data in which the various image data generated by the three-dimensional data generation circuitry 15 are arranged at position coordinates after coordinate conversion, that is, corresponding positions in the three-dimensional space of the biological coordinate system. More specifically, for example, after the position information of the various image data generated by the three-dimensional data generation circuitry 15 undergoes coordinate conversion, the image calculation circuitry 16b executes the image generation function 161b. By executing the image generation function 161b, the image calculation circuitry 16b generates map display image data in which the two-dimensional image data, rendering image data, M-mode image data, or spectrum Doppler image data is arranged at the position coordinates after coordinate conversion. Thus, in the map display image data, the various image data are displayed from a bird's eye view in the three-dimensional space of the biological coordinate system.

Note that the reference portion control function 162, the coordinate conversion function 163, and the image generation function 161b have been explained as modules forming the image processing program according to this embodiment. The present invention, however, is not limited to this. For example, the image calculation circuitry 16b may include dedicated hardware circuitry for implementing the reference portion control function 162, that for implementing the coordinate conversion function 163, and that for implementing the image generation function 161b. The image calculation circuitry 16b may be implemented by an ASIC, FPGA, CPLD, or SPLD which incorporates the dedicated hardware circuitry.

Figure 23:
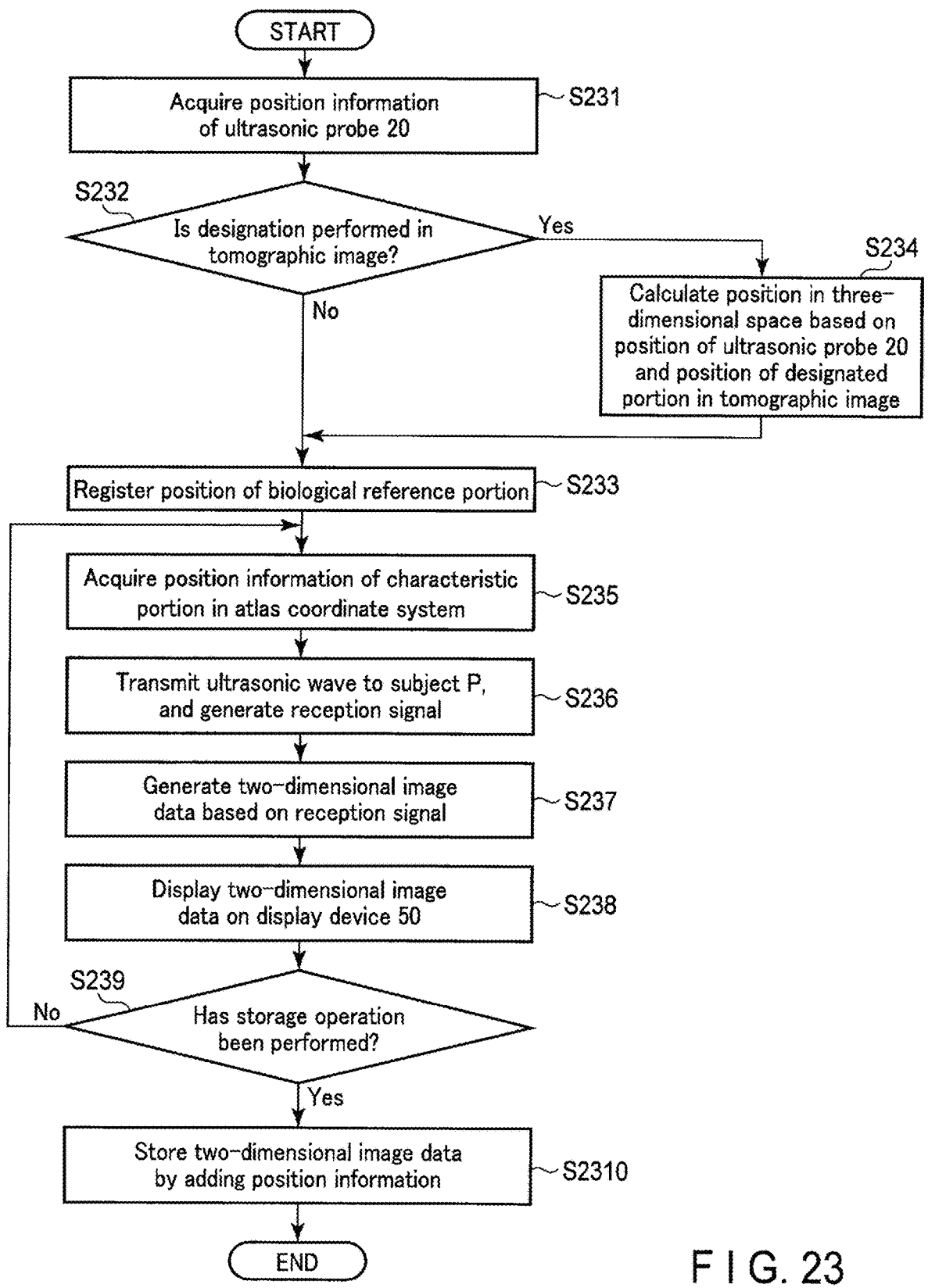
FIG. 23 is a flowchart illustrating an example of the procedure of processing in which the ultrasonic diagnostic apparatus shown in FIG. 22 acquires ultrasonic image data.

FIG. 23 is a flowchart illustrating an example of the procedure of processing in which the ultrasonic diagnostic apparatus 1b according to the second embodiment acquires two-dimensional image data. A case in which a xiphoid process is set as a biological reference portion will be exemplified below. Note that setting a xiphoid process as a biological reference portion corresponds to setting a biological reference portion on a body surface.

Furthermore, a case in which the three-dimensional data generation circuitry 15 generates two-dimensional image data will be exemplified below.

Prior to ultrasonic examination of a subject P, diagnosis information is input, transmission/reception conditions are set, and conditions for collecting various ultrasonic data are set in response to an operator instruction via the input interface 110. These pieces of information are stored in the internal storage circuitry 18.

In addition, prior to ultrasonic examination of the subject P, the operator registers the position information of a biological reference portion R. More specifically, for example, the operator brings the ultrasonic probe 20 into contact with the body surface of the subject P in the vertical direction, as shown in FIG. 3, so as to scan an axial surface including the xiphoid process set as the biological reference portion R. After bringing the ultrasonic probe 20 into contact with the subject P, the operator presses a button provided in the ultrasonic probe 20 or the operation panel 61. This inputs a designation instruction to the control circuitry 112b.

Upon receiving the designation instruction, the control circuitry 112b acquires a position (x, y, z, θx, θy, θz) of the ultrasonic probe 20 calculated by a position detection device 33 when the designation instruction is input (step S231).

After the ultrasonic probe 20 is brought into contact with the subject P, the ultrasonic probe 20 transmits ultrasonic waves to the subject P, and an ultrasonic tomographic image of the subject P at the position with which the ultrasonic probe 20 is in contact is displayed on the display device 50. After the pressing of the button, the control circuitry 112b determines whether an arbitrary portion in the ultrasonic tomographic image displayed on the display device 50 is designated (step S232). For example, a touch command screen serving as the input interface 110 is provided on the surface of the display device 50. If the operator touches a predetermined portion in the ultrasonic tomographic image displayed on the display device 50, the touch command screen detects the touch on the portion, and designation of the portion by the operator is recognized. Note that the operator may designate the predetermined portion in the ultrasonic tomographic image displayed on the display device 50 by operating a cursor on the display device 50 using a trackball or the like.

If the xiphoid process is set as the biological reference portion R, an arbitrary portion in the ultrasonic tomographic image displayed on the display device 50 is not designated after the pressing of the button (NO in step S232). The control circuitry 112b registers, as the position information of the biological reference portion R, the position (x, y, z, θx, θy, θz) of the ultrasonic probe 20 acquired in step S231 (step S233).

On the other hand, the biological reference portion does not always exist on the body surface. The biological reference portion may exist in a body such as a mitral valve or portal vein bifurcation. In this case, after the pressing of the button, an arbitrary portion in the ultrasonic tomographic image displayed on the display device 50 is designated, as shown in, for example, FIG. 4. If an arbitrary portion in the ultrasonic tomographic image displayed on the display device 50 is designated after the pressing of the button (YES in step S232), the control circuitry 112h acquires the position (x, y, z, θx, θy, θz) of the ultrasonic probe 20 calculated by the position detection device 33 when the designation instruction is input, and a position (x', y'), in the ultrasonic tomographic image, of the portion designated in the ultrasonic tomographic image.

After the position (x, y, z, θx, θy, θz) of the ultrasonic probe 20 and the position (x', y') in the ultrasonic tomographic image are acquired, the image calculation circuitry 16b executes the reference portion control function 162. By executing the reference portion control function 162, the image calculation circuitry 16b calculates the position of the portion designated in the ultrasonic tomographic image in the magnetic field coordinate system of the position sensor system 30 based on the position (x, y, z, θx, θy, θz) of the ultrasonic probe 20 and the position (x', y') in the ultrasonic tomographic image (step S234). The control circuitry 112b registers the calculated position as the position information of the biological reference portion R in the body (step S233).

Note that when setting the biological reference portion, the operator may refer to past image data about the same patient, which have been acquired in past consultation. The past image data include ultrasonic image data, CT image data, MR image data, PET image data, and X-ray image data. The control circuitry 112b may store, in the internal storage circuitry 18, the referred past image data in association with the acquired image data.

In steps S232 to S234, a case in which the position of the biological reference portion existing in the body is acquired based on designation of an arbitrary portion in the ultrasonic tomographic image displayed on the display device 50 has been exemplified. The embodiment, however, is not limited to this. The ultrasonic diagnostic apparatus 1b acquires, from the internal storage circuitry 18 or the like, as a reference image, a three-dimensional ultrasonic image, three-dimensional CT image, three-dimensional MR image, or three-dimensional X-ray image which has been acquired from the same subject in past consultation and includes a region corresponding to the same position as that of the ultrasonic tomographic image acquired in real time. Then, the control circuitry 112b may have an image reference function of displaying the reference image on the display device 50 at the time of ultrasonic examination and allowing the operator to refer to the reference image. Processing when a past three-dimensional CT image is displayed on the display device 50 as a reference image will be described in detail below.

Prior to ultrasonic examination, the magnetic field coordinate system of the position sensor system 30 is associated with the coordinate system of the three-dimensional CT image by a desired method. This associates the position of the ultrasonic probe 20 with the position in the three-dimensional CT image.

After the pressing of the button provided in the ultrasonic probe 20 or the operation panel 61, the control circuitry 112b determines whether an arbitrary portion in the three-dimensional CT image displayed on the display device 50 is designated. If an arbitrary portion in the three-dimensional CT image displayed on the display device 50 is designated after the pressing of the button, the control circuitry 112b acquires the position of the ultrasonic probe 20 calculated by the position detection device 33 at the time of designation and the position, in the three-dimensional CT image, of the portion designated in the three-dimensional CT image. After the position of the ultrasonic probe 20 and the position in the three-dimensional CT image are acquired, the image calculation circuitry 16b calculates the position of the portion designated in the three-dimensional CT image in the magnetic field coordinate system of the position sensor system 30 based on these positions. The control circuitry 112b registers the calculated position as the position information of the biological reference portion R in the living body.

In step S232, a case in which the operator designates an arbitrary portion in the ultrasonic tomographic image displayed on the display device 50 has been exemplified. The present invention, however, is not limited to this. As the arbitrary portion in the reference image or the ultrasonic tomographic image displayed on the display device 50, a desired portion may be automatically recognized by an image analysis function and then designated.

After the position information of the biological reference portion R is registered, the operator performs ultrasonic examination of the subject P using the ultrasonic probe 20. The position sensor system 30 detects the position of the ultrasonic probe 20. The detected position is output to the main body device 10b as position information in the magnetic field coordinate system (step S235).

For example, the ultrasonic probe 20 manually, three-dimensionally scans the subject P using a plurality of ultrasonic transducers for two-dimensionally scanning the subject P. The ultrasonic probe 20 emits ultrasonic waves, and receives a reflected wave signal obtained when the ultrasonic waves are reflected. The ultrasonic reception circuitry 12 performs various processes for the reflected wave signal received by the ultrasonic probe 20, and generates a reception signal (step S236).

The B-mode processing circuitry 13 generates B-mode RAW data on a two-dimensional ultrasonic scanning line based on the reception signal received from the ultrasonic reception circuitry 12. The three-dimensional data generation circuitry 15 generates a plurality of two-dimensional image data added with the position information by executing RAW-pixel conversion for the two-dimensional B-mode RAW data generated by the B-mode processing circuitry 13 (step S237). The plurality of two-dimensional image data represent a plurality of tomographic images collected while manually moving the ultrasonic probe. The display processing circuitry 17 converts one of the plurality of generated two-dimensional image data into a video signal, and displays it on the display device 50 (step S238).

If the operator carefully observes the two-dimensional image displayed on the display device 50 while moving the ultrasonic probe 20, and determines that the displayed two-dimensional image includes a desired structure or the like, he/she performs a freeze operation via the input interface 110. Two-dimensional image data corresponding to a plurality of frames immediately before the freeze operation are saved in the image memory 19. If the operator confirms a two-dimensional image saved in the image memory 19, and determines that the saved two-dimensional image is a two-dimensional image to be stored in the internal storage circuitry 18, he/she performs a storage operation for the two-dimensional image via the input interface 110. At this time, when a predetermined switch operation is set as a start point, if a predetermined time elapses or before the next switch operation is performed, the storage operation for the two-dimensional image added with the position information may be performed.

The control circuitry 112b determines whether a storage operation has been performed (step S239). If a storage operation has been performed (YES in step S239), the control circuitry 112b adds position information to the two-dimensional image data having undergone the storage operation, and stores it in the internal storage circuitry 18 (step S2310). Note that the position information added to the two-dimensional image data may be position information in the magnetic field coordinate system or position coordinates in the biological coordinate system after coordinate conversion.

If the ultrasonic probe 20 attached with a position sensor 32 is a mechanical four-dimensional probe (a three-dimensional probe with a mechanical swinging mechanism) or a two-dimensional probe, the control circuitry 112b stores the two-dimensional image data having undergone the storage operation, and also stores, in the internal storage circuitry 18, a plurality of two-dimensional image data F1 to Fn generated by an electronic scan in an slice direction or the swing of the ultrasonic probe 20 (step S2310). F1 to Fn represent the acquisition ordinal numbers of the two-dimensional image data. The two-dimensional image data F1 to Fn are added with position information calculated based on the position of the ultrasonic probe 20 and three-dimensional operation information, and then stored. Note that the position information added to the two-dimensional image data F1 to Fn may be position information in the magnetic field coordinate system or position coordinates in the biological coordinate system after coordinate conversion.

If no storage operation has been performed (NO in step S239), the control circuitry 112b cancels the freeze operation, and returns the process to step S235. Note that the two-dimensional image data may always be added with position information and stored in real time by eliminating the processing in step S239.

Figure 24:
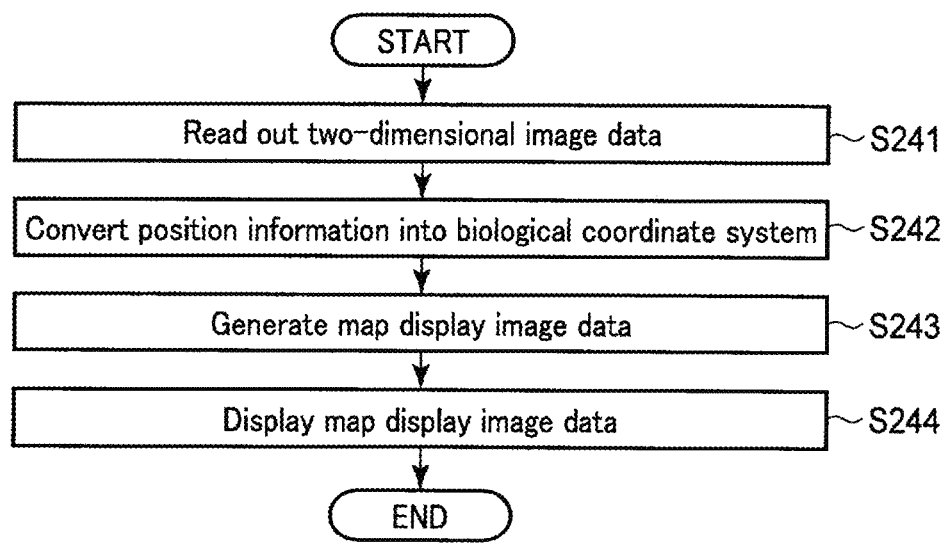
FIG. 24 is a flowchart illustrating the procedure of processing in which the ultrasonic diagnostic apparatus shown in FIG. 22 displays map display image data on a display device.

FIG. 24 is a flowchart illustrating an example of the procedure of processing in which the ultrasonic diagnostic apparatus 1b according to the second embodiment displays map display image data on the display device 50. A description of FIG. 24 assumes that the two-dimensional image data F1 to Fn are stored in the internal storage circuitry 18 in the processing shown in FIG. 23.

When reviewing past ultrasonic examination or creating a report of performed ultrasonic examination, the operator inputs, via the input interface 110, a display instruction to display, on the display device 50, two-dimensional ultrasonic images acquired in past examination. If the display instruction is input, the control circuitry 112h displays the plurality of two-dimensional image data on the display device 50 so as to efficiently select desired two-dimensional image data from the plurality of two-dimensional image data acquired in past examination. For example, the plurality of two-dimensional image data acquired in past examination are displayed on the display screen using thumbnail images representing the two-dimensional image data. The plurality of two-dimensional image data acquired in past examination may be grouped or sorted using diagnosis information, operation information, image condition information, ultrasonic data, acquisition positions, and the like, and then displayed.

Note that display according to the display instruction from the operator may be performed, as follows. If the display instruction is input, the image calculation circuitry 16b executes the image generation function 161b to read out the registered position of the biological reference portion. By executing the image generation function 161b, the image calculation circuitry 16b generates, based on the readout position of the biological reference portion, image data representing only the coordinate axes of the biological coordinate system. The image data representing only the coordinate axes of the biological coordinate system is displayed on the display device 50 via the processing in the display processing circuitry 17. The operator is allowed to designate, by an input from the input interface 110, a predetermined portion along the coordinate axes of the biological coordinate system displayed on the display device 50. If a predetermined portion along the coordinate axes of the biological coordinate system is designated, it is recognized that the two-dimensional image data acquired in or near the designated portion has been selected.

If the operator selects the two-dimensional image data F1 to Fn, the control circuitry 112b reads out the two-dimensional image data F1 to Fn from the internal storage circuitry 18 (step S241). If the two-dimensional image data F1 to Fn are generated, the image calculation circuitry 16b executes the coordinate conversion function 163. The two-dimensional image data F1 to Fn are added with position information. By executing the coordinate conversion function 163, the image calculation circuitry 16b converts the coordinate system of the position information added to the two-dimensional image data F1 to Fn from the magnetic field coordinate system into the biological coordinate system defined based on the position of the biological reference portion R (step S242).

Subsequently, the image calculation circuitry 16b executes the image generation function 161b. By executing the image generation function 161b, the image calculation circuitry 16b generates map display image data by arraying the two-dimensional image data F1 to Fn at corresponding positions in the three-dimensional space of the biological coordinate system (step S243). The generated map display image data is displayed on the display device 50 through various processes in the display processing circuitry 17 (step S244).

Figure 25:
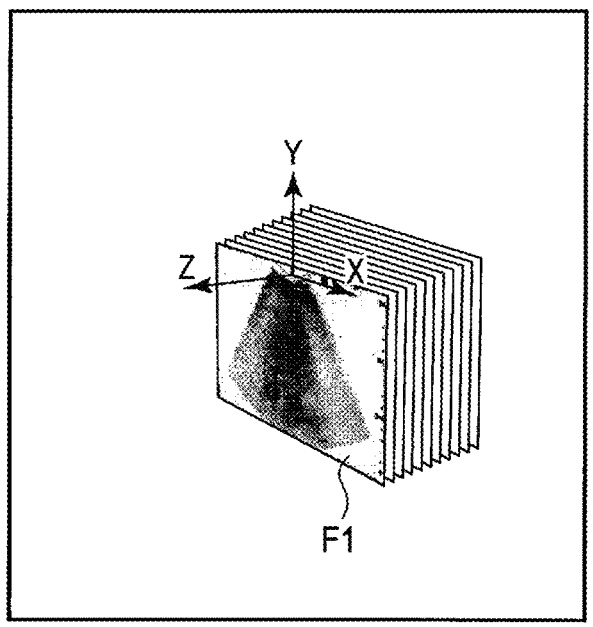
FIG. 25 is a view showing map display image data displayed on the display device shown in FIG. 22.
Figure 26:
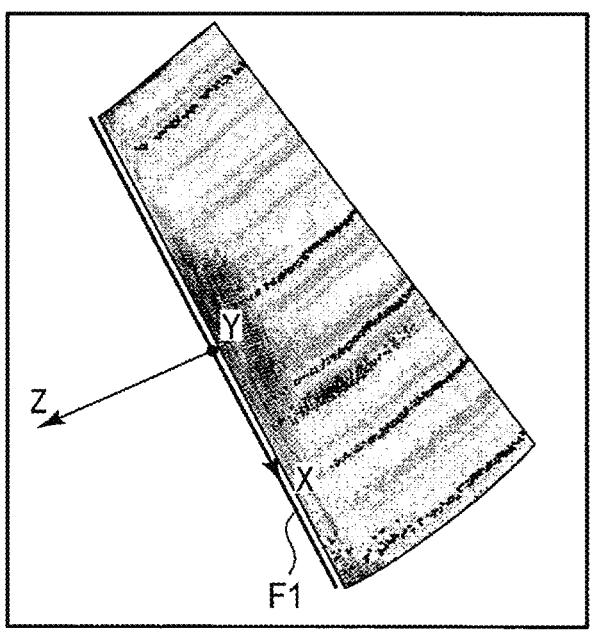
FIG. 26 is a view when the map display image shown in FIG. 25 is displayed in the y-axis direction.

FIG. 25 is a view showing an example of the map display image data displayed on the display device 50 shown in FIG. 22. The map display image shown in FIG. 25 is obtained by setting the xiphoid process as the biological reference portion R, and displaying, on the display device 50, map display image data acquired when the ultrasonic probe 20 is brought into contact with the biological reference portion R. The two-dimensional image data F1 to Fn acquired by bringing the ultrasonic probe 20 into contact with the xiphoid process include an image of an organ such as a liver. Coordinate axes shown in FIG. 25 match, for example, the coordinate axes of the biological coordinate system shown in FIG. 6. Referring to FIG. 25, a two-dimensional image F1 based on the two-dimensional image data F1 is arranged so that the transmission position of an ultrasonic wave in the two-dimensional image F1 matches the origin of the biological coordinate system. Two-dimensional images F2 to Fn based on the two-dimensional image data F2 to Fn are respectively arranged at positions away from the two-dimensional image F1 by distances corresponding to swing angles in the z-axis direction.

The operator can change the display direction of the map display image by an input via the input interface 110. FIG.

26 is a view showing a display example when the map display image shown in FIG. 25 is displayed in the y-axis direction.

Figure 27:
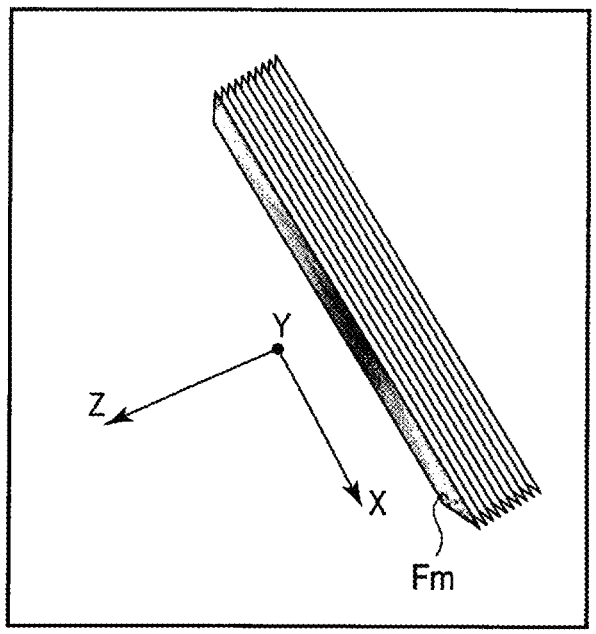
FIG. 27 is a view showing a map display image when a two-dimensional image, arranged at a foremost position, of the map display image shown in FIG. 25 is changed.

By an input via the input interface 110, the operator can select the two-dimensional image displayed at a foremost position in the map display image. FIG. 27 is a view showing an example of the map display image when a two-dimensional image Fm is displayed at the foremost position by operating a slider switch. Note that the operator may intuitionally select, using the mouse or touch command screen, the two-dimensional image displayed at the foremost position from the two-dimensional image group included in the map display image.

Figure 28:
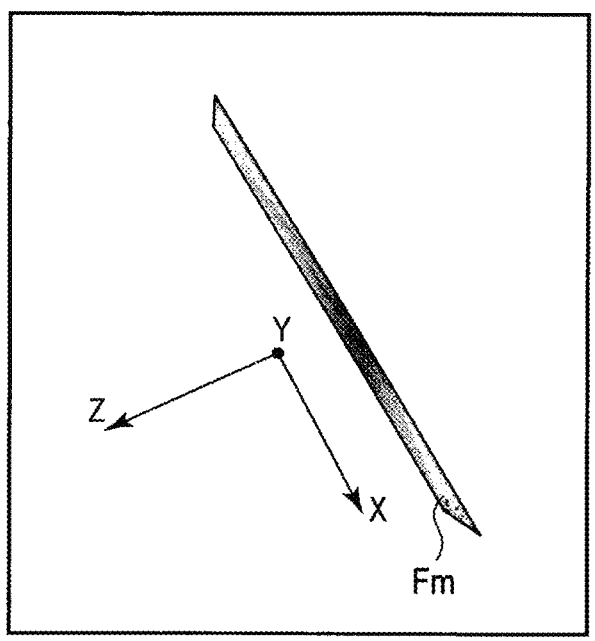
FIG. 28 is a view showing a map display image when only a predetermined two-dimensional image is displayed.

The operator can select the displayed two-dimensional image in the map display image by an input via the input interface 110. FIG. 28 is a view showing an example of the map display image when only the two-dimensional image Fm is displayed by operating the slider switch. Note that the operator may intuitionally select, using the mouse or touch command screen, the displayed two-dimensional image from the two-dimensional image group included in the map display image.

Note that the image data generated by the image generation function 161b of the image calculation circuitry 16b is not limited to the map display image data. By executing the image generation function, the image calculation circuitry 16b may generate image data including the map display image data and the two-dimensional image data selected from the two-dimensional image data group indicated by the map display image data. FIGS. 29, 30, 31, and 32 are views each showing a display example of the image data including the map display image data and the two-dimensional image data. Each of the images shown in FIGS. 29, 30, 31, and 32 includes a first display region G10 where the two-dimensional image is displayed and a second display region G20 where the map display image is displayed.

The first display region G10 includes a display bar G11 for selecting a two-dimensional image to be displayed in the first display region G10 from the two-dimensional image group included in the map display image data. In the display bar G11, the operator can horizontally move a designator G12 by an input from the input interface 110. In accordance with the movement of the designator G12, the displayed two-dimensional image is switched. At this time, the order of switching the two-dimensional images may be an order related to position information or an order of collection times. In this embodiment, a case in which the two-dimensional images are sorted in the order related to the position information will be exemplified. Ultrasonic data such as annotation information D1, ultrasonic transmission condition information D2 including an MI value, and acquisition time information D3 are read out from the internal storage circuitry 18 and displayed in the first display region G10.

FIGS. 29 and 30 show a case in which the two-dimensional image F1 selected in the map display image displayed in the second display region G20 is displayed in the first display region G10. At this time, the designator G12 of the display bar G11 is located at the left end. For example, the operator can select a desired two-dimensional image from the two-dimensional image group included in the map display image by operating the slider switch. Note that the operator may intuitionally select a desired two-dimensional image from the two-dimensional image group included in the map display image by touching the map display image using the mouse or touch command screen. Alternatively, the operator may select a desired two-dimensional image from the two-dimensional image group included in the map display image by operating the designator G12 of the display bar G11 using the mouse or touch command screen.

Figure 31:
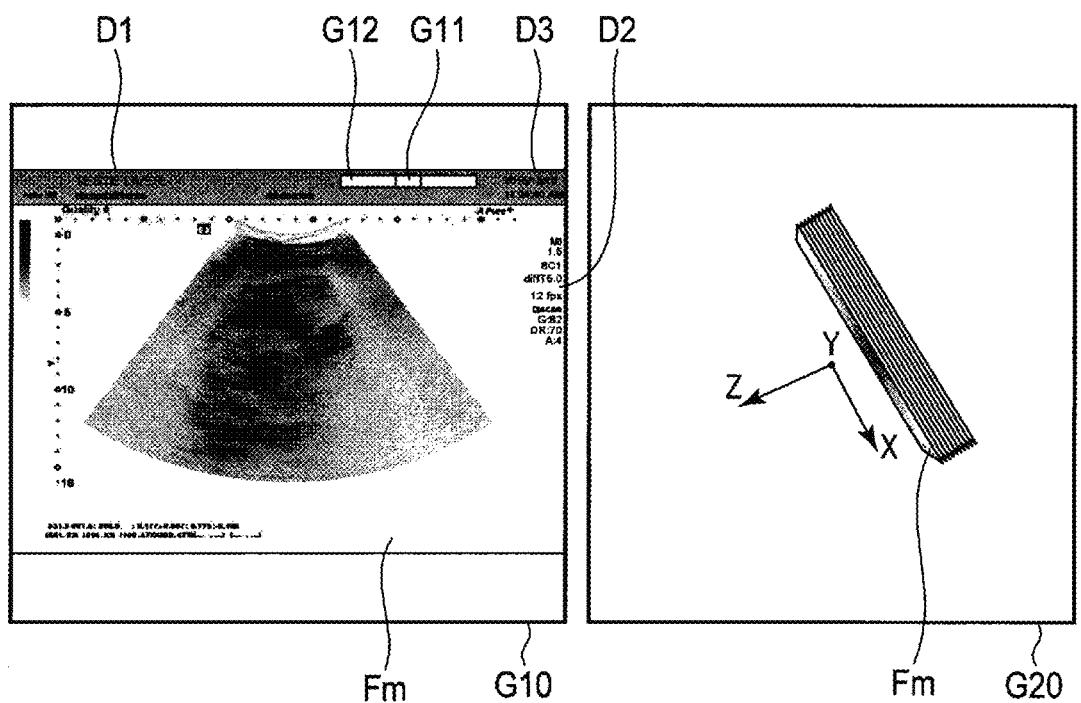
FIG. 31 is a view showing a screen on which the map display image and one of the two-dimensional images arranged in the map display image are displayed.
Figure 32:
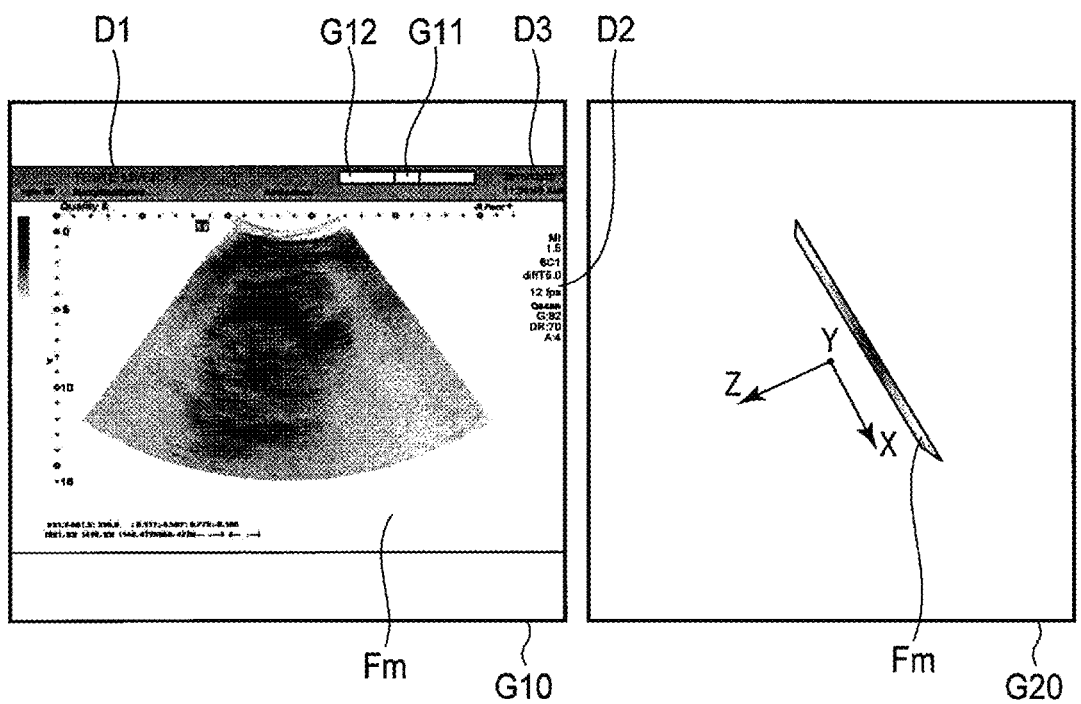
FIG. 32 is a view showing a screen on which the map display image and the two-dimensional image arranged in the map display image are displayed.
Figure 33:
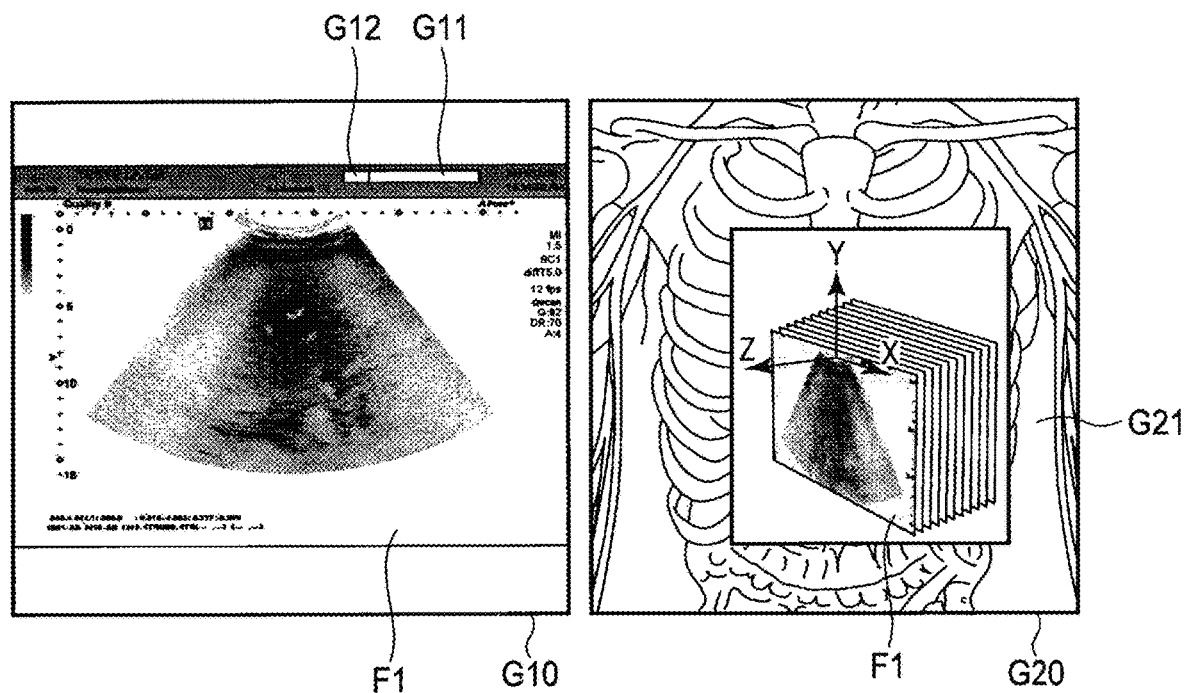
FIG. 33 is a view showing a screen on which the map display image superimposed on an atlas image and one of the two-dimensional images arranged in the map display image are displayed.
Figure 34:
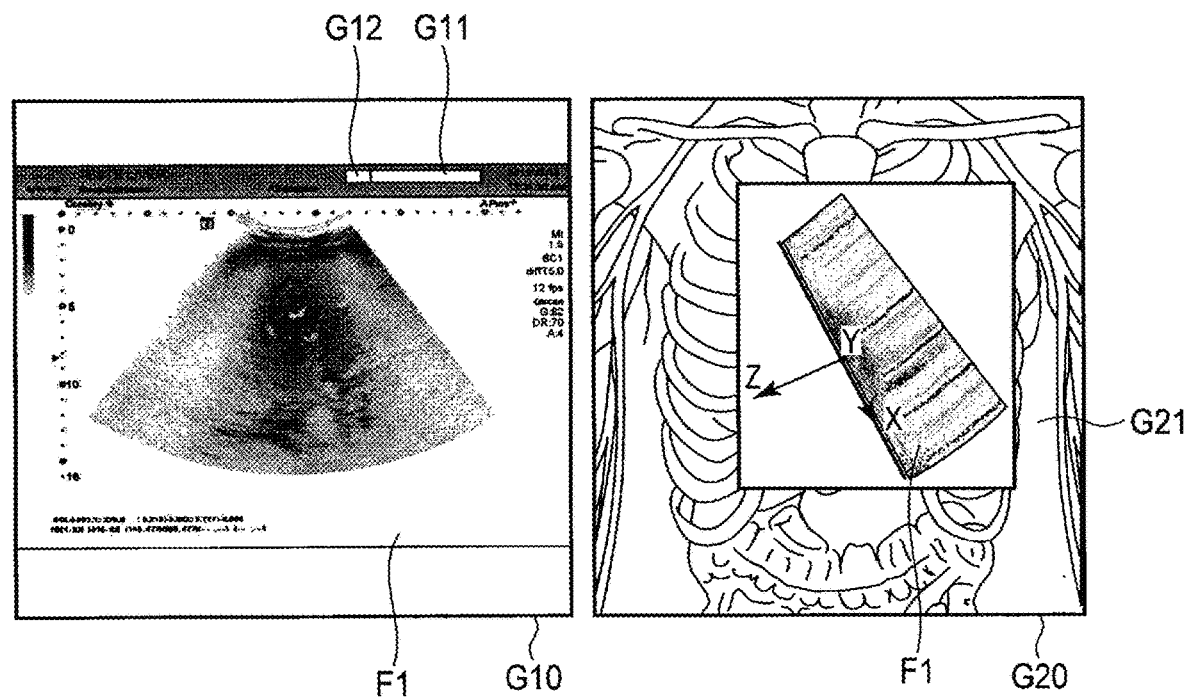
FIG. 34 is a view showing another example of the screen shown in FIG. 33.

FIGS. 31 and 32 show a case in which the two-dimensional image Fm selected in the map display image displayed in the second display region G20 is displayed in the first display region G10. At this time, for example, the designator G12 of the display bar G11 is located near the center.

Image data generated by the image generation function 161b of the image calculation circuitry 16b is not limited to the above image data. By executing the image generation function 161b, the image calculation circuitry 16b may generate image data by superimposing the map display image data on an image (to be referred to as an atlas image hereinafter in this embodiment) schematically representing a structure such as an organ in the living body. FIGS. 33, 34, 35, and 36 are views each showing a display example of the image data obtained by superimposing the map display image data on an atlas image. Each of the images shown in FIGS. 33, 34, 35, and 36 includes the first display region G10 where the two-dimensional image is displayed, and the second display region G20 where the map display image is superimposed and displayed on an atlas image G21.

At this time, if a position corresponding to the acquisition position of the two-dimensional image data is set as the display position of the map display image on the atlas image G21, it is possible to more effectively understand the acquisition position of the two-dimensional image data. Referring to FIGS. 33, 34, 35, and 36, for example, the map display image is superimposed on the atlas image G21 so that the position of the xiphoid process at which the two-dimensional image data has been acquired, that is, the origin of the biological coordinate system is located at the xiphoid process on the atlas image G21. Therefore, referring to FIGS. 33, 34, 35, and 36, it is possible to readily understand that the two-dimensional image data F1 and Fm have been acquired on the xiphoid process.

As a method of associating the position where the two-dimensional image data has been acquired with the display position on the atlas image G21, for example, there are various methods such as a method of adding, to generated two-dimensional image data, a tag representing a structure such as an organ for which the data is acquired, and a method of assigning in advance, to the atlas image G21, coordinate information with respect to the biological coordinate system. Furthermore, FIGS. 33, 34, 35, and 36 show a case in which the map display image data is superimposed on the two-dimensional atlas image G21. However, the atlas image is not limited to the two-dimensional image, and may be a three-dimensional image.

Figure 37:
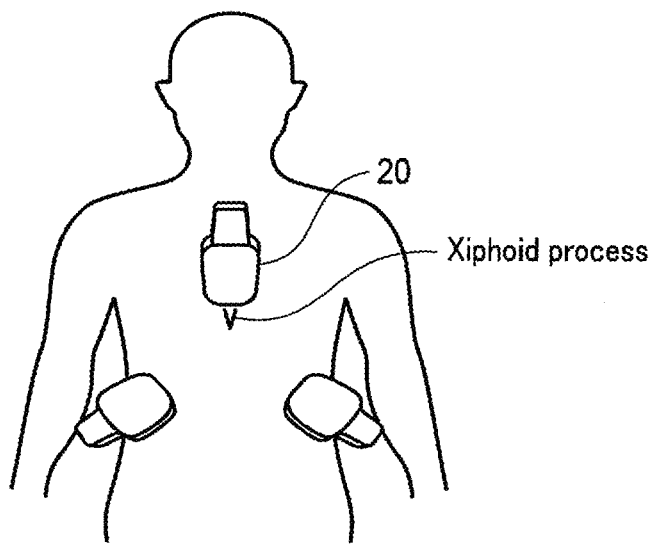
FIG. 37 is a view when a plurality of position coordinate points of a subject are acquired.

Note that when displaying the atlas image, it is possible to more effectively understand the acquisition position of the two-dimensional image data by adjusting the size, shape, position, and the like of a structure such as an organ depicted in the atlas image in accordance with the body build or the like of the subject P. Information about the body build or the like of the subject P, that is, body build information can be acquired by, for example, registering three-dimensional position information of the subject P at multiple points. For example, as shown in FIG. 37, when registering the position of the biological reference portion, the positions of the right and left body sides are registered as body build information. By executing the image generation function 161b, the image calculation circuitry 16b corrects, based on the registered body build information, the size, shape, position, and the like of the structure such as the organ depicted in the atlas image. The correction processing of the atlas image based on the body build information is effective when superimposing, on the atlas image, the ultrasonic image acquired for a structure such as a breast having a relatively large individual difference between subjects. Such correction processing is also effective when superimposing ultrasonic images acquired for a leg and arm on the atlas image.

In step S241 of FIG. 24, a case in which a desired one of the plurality of two-dimensional image data displayed on the display device 50 has been exemplified. The present invention, however, is not limited to this. Desired two-dimensional image data may be allowed to be selected when the operator designates a predetermined portion in the atlas image displayed on the display device 50 by an input from the input interface 110. For example, if the operator designates a predetermined portion in the atlas image via the input interface 110, map display image data in which two-dimensional image data acquired in or near the designated portion is arranged is displayed on the atlas image.

Note that as a method of associating the designated portion on the atlas image with the portion where the two-dimensional image data is acquired, for example, there are various methods such as a method of adding, to generated two-dimensional image data, a tag representing a structure such as an organ for which the data is acquired, and a method of assigning in advance, to the atlas image, coordinate information with respect to the biological coordinate system. A cursor for designating the predetermined portion in the atlas image may have a shape imitating the shape of the ultrasonic probe 20. If the predetermined portion in the atlas image is designated by the cursor having the ultrasonic probe shape, the image calculation circuitry 16b displays, on the atlas image, map display image data in which two-dimensional image data actually acquired by the ultrasonic probe 20 of the same orientation is arranged. This enables the operator to more intuitively understand the acquisition position of the two-dimensional image data.

The image data generated by the image generation function 161b of the image calculation circuitry 16b is not limited to the above image data. By executing the image generation function 161b, the image calculation circuitry 16b generates image data by superimposing the map display image data on CT image data or MR image data about the same patient, which has been acquired in past diagnosis. Note that the CT image data and MR image data may be two- or three-dimensional image data. At this time, if a position corresponding to the acquisition position of the two-dimensional image data is set as the display position of the two-dimensional image on the CT image or MR image, it is possible to more effectively understand the acquisition position of the two-dimensional image data. As a method of associating the acquisition position of the two-dimensional image data with the display position on the CT image or MR image, for example, there are various methods such as a method of adding, to generated two-dimensional image data, a tag representing a structure such as an organ for which the data is acquired, and a method of assigning in advance, onto the CT image or the MR image, coordinate information with respect to the biological coordinate system.

Desired two-dimensional image data may be allowed to be selected when the operator designates a predetermined portion in the CT image or MR image displayed on the display device 50 by an input from the input interface 110. For example, if the operator designates the predetermined portion in the CT image or MR image via the input interface 110, map display image data in which two-dimensional image data acquired in or near the designated portion is arranged is displayed on the CT image or MR image.

Note that as a method of associating the designated portion on the CT image or MR image with the portion where the two-dimensional image data is acquired, for example, there are various methods such as a method of adding, to generated two-dimensional image data, a tag representing a structure such as an organ for which the data is acquired, and a method of assigning in advance, to the CT image or MR image, coordinate information with respect to the biological coordinate system. A cursor for designating the predetermined portion in the CT image or MR image may have a shape imitating the shape of the ultrasonic probe 20. If the predetermined portion in the CT image or MR image is designated by the cursor having the ultrasonic probe shape, the image calculation circuitry 16b displays, on the CT image or MR image, map display image data in which two-dimensional image data actually acquired by the ultrasonic probe 20 of the same orientation is arranged. This enables the operator to more intuitionally understand the acquisition position of the two-dimensional image data.

The processing in a case in which map display image data is displayed when reviewing past ultrasonic examination or creating a report of performed ultrasonic examination has been explained with reference to FIG. 24. The present invention, however, is not limited to this. The image generation function 161b of the image calculation circuitry 16b may be executed while two-dimensional image data is acquired in ultrasonic examination. That is, the image shown in one of FIGS. 25, 26, 27, 28, 29, 30, 31, 32, 33, 34, 35, and 36 is displayed on the display device 50 together with a two-dimensional image based on two-dimensional image data acquired in real time.

At this time, in the map display image data displayed together with the two-dimensional image displayed in real time, a two-dimensional image data group acquired in the same examination as that of the displayed two-dimensional image may be arranged while being updated. This allows the operator to correctly grasp a portion to be confirmed in another direction.

Alternatively, in the map display image data displayed together with the two-dimensional image displayed in real time, a two-dimensional image data group acquired in examination performed in the past for the same subject may be arranged. Note that if a two-dimensional image data group acquired in past examination for the same subject is arranged, it is necessary to match the position of the biological reference portion registered in past examination with that registered in current examination. This enables the operator to advance examination while recognizing the progress of a region of interest.

As described above, in the second embodiment, the image calculation circuitry 16b converts position information, added to stored image data, in a predetermined three-dimensional coordinate system into position coordinates in the biological coordinate system based on the position information of the biological reference portion. Based on the converted position coordinates, the image calculation circuitry 16b generates map display image data for displaying image data from a bird's eye view in the three-dimensional space of the biological coordinate system.

Note that there is provided a technique of adding an annotation to a displayed image to estimate an acquisition position where an ultrasonic image is acquired. However, a general organ name, a rough position in an organ, or a general vein name is described as an annotation. Thus, it is impossible to specify the acquisition position of the ultrasonic image only by the annotation. The latest ultrasonic diagnostic apparatus has a fusion mode of displaying an ultrasonic tomographic image and an MPR image acquired from a three-dimensional CT image or three-dimensional MR image and corresponding to the ultrasonic tomographic image. In the fusion mode, it is possible to notify, in addition to the scan operator, a doctor and a technician of the position of the ultrasonic tomographic image in the body by comparing the ultrasonic tomographic image with the CT image or MR image. However, diagnosis using an ultrasonic diagnostic apparatus is often performed in an early stage, and a CT image or MR image already exists for the same case. Thus, a case in which the fusion mode can be used is limited. Since the ultrasonic diagnostic apparatus 1b according to the second embodiment generates map display image data, even a person other than the scan operator can readily understand, by seeing the map display image data, a specific position on the living body surface with which the ultrasonic probe is brought into contact and a specific direction in the body in which the ultrasonic probe is moved when acquiring the image data. That is, even if the scan area is subjectively set by the scan operator, it is possible to readily understand the acquisition position of the ultrasonic image.

Therefore, the ultrasonic diagnostic apparatus 1b according to the second embodiment can improve the objectivity of ultrasonic diagnosis.

Other Embodiments

Figure 38:
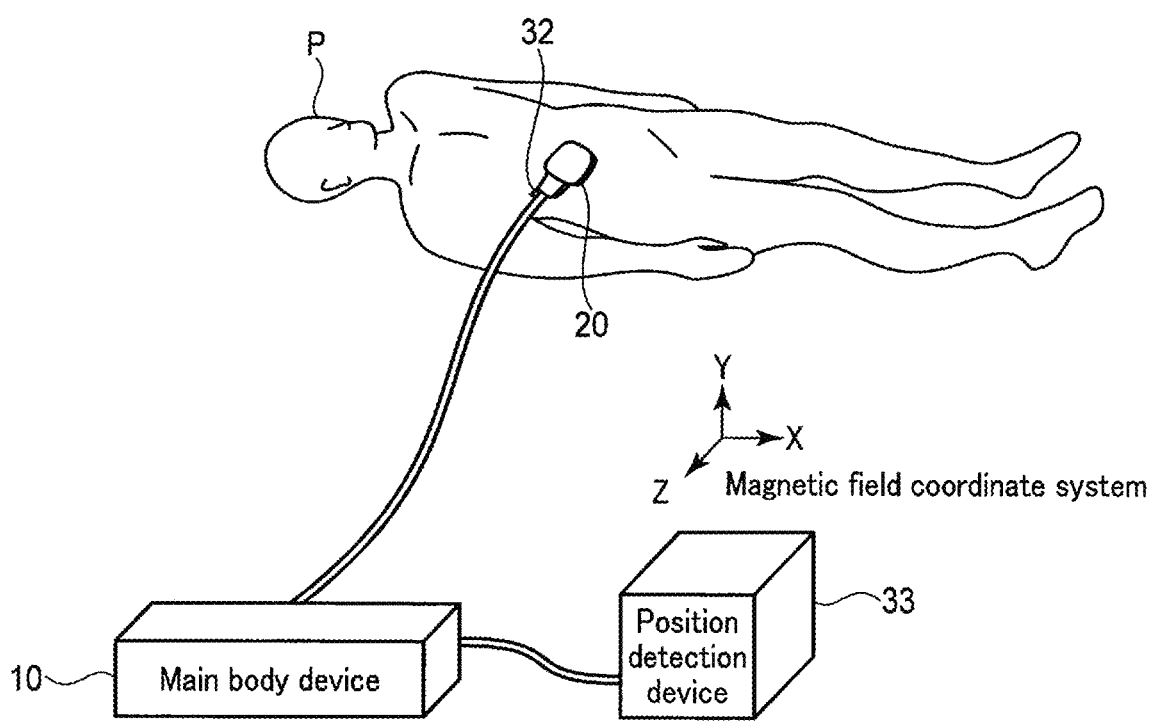
FIG. 38 is a view showing the configuration of a position sensor system shown in FIG. 1, 16, or 22.
Figure 39:
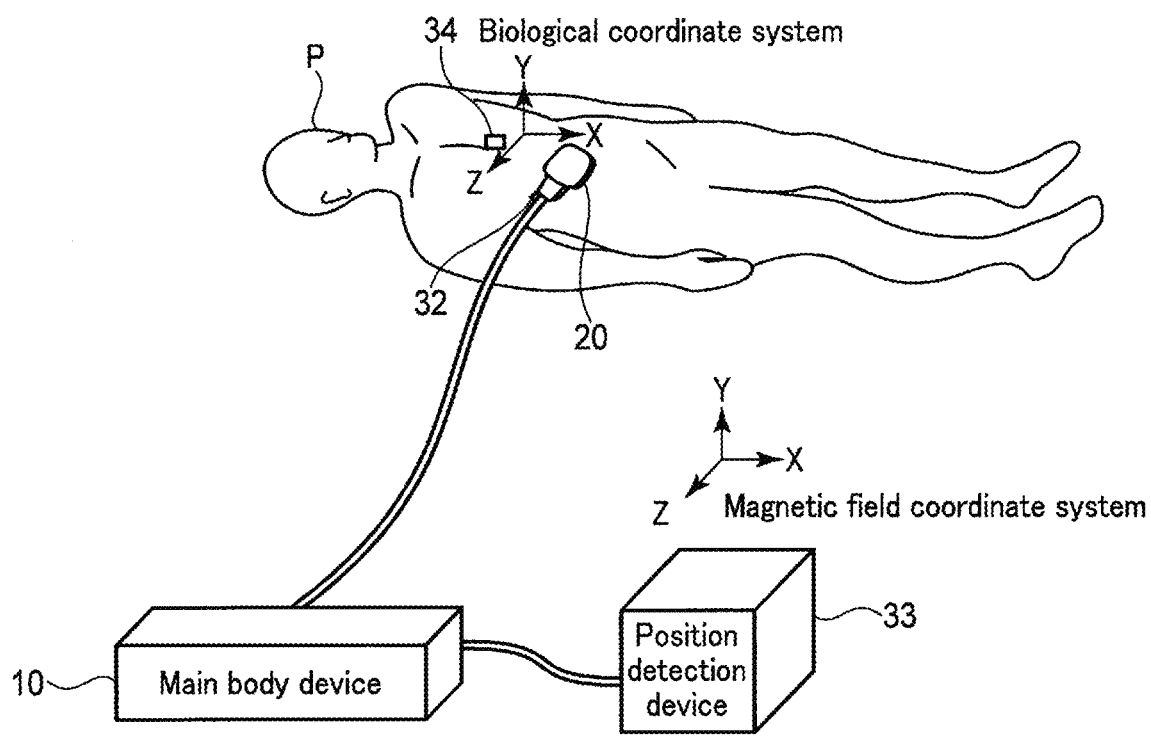
FIG. 39 is a view showing another configuration of the position sensor system shown in FIG. 1, 16, or 22.

Note that in the above embodiment, a case in which the position sensor system 30 includes the position sensor 32, as shown in FIG. 38, has been explained. However, the number of position sensors provided in the position sensor system 30 is not limited to one. The position sensor system 30 may include a second position sensor 34. As shown in FIG. 39, the second position sensor 34 is adhered to the xiphoid process as the biological reference portion on the body surface of the subject P. The position detection device 33 transmits the position information of the second position sensor 34 to the main body device 10, 10a, or 10b. The control circuitry 112, 112a, or 112b recognizes the position of the second position sensor 34 as the position of the biological reference portion. Note that if the biological reference portion exists in the body, the position of the biological reference portion is calculated based on the position of the second position sensor 34 and the position of a designated portion in an ultrasonic tomographic image. With this processing, even if the subject P moves during examination and it is necessary to change the posture of the subject P during examination, it is possible to continuously recognize the biological reference portion. In follow-up observation, a common biological coordinate system is generated by installing the second position sensor 34 in the biological reference portion at the same place, and it is thus possible to readily observe the organ at the same place and perform comparison.

Figure 40:
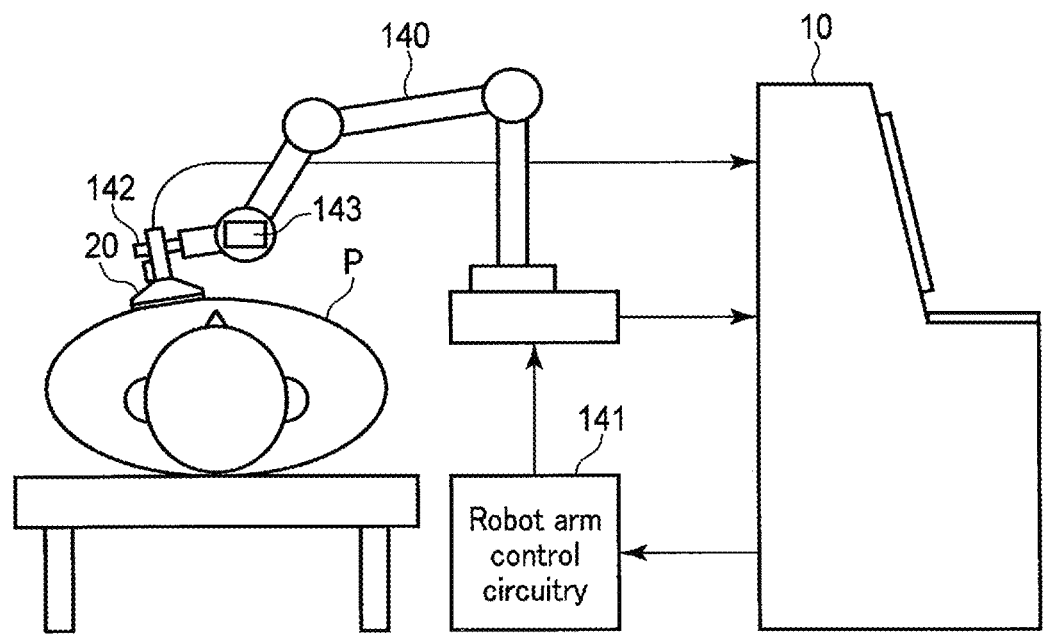
FIG. 40 is a view showing still another configuration of the position sensor system shown in FIG. 1, 16, or 22.

The above embodiment has exemplified a case in which the position sensor system 30 using the position sensor is used to acquire the position of the biological reference portion. However, the position sensor system 30 is not limited to that using the position sensor. For example, as shown in FIG. 40, a position sensor system using a robot arm 140 may be adopted.

Robot arm control circuitry 141 of the robot arm 140 drives the robot arm 140. The position of the ultrasonic probe 20 supported by a probe holder 142 of the robot arm 140 is acquired based on an output from a robot arm sensor 143 attached to the robot arm 140. A position sensor, velocity sensor, acceleration sensor, pressure sensor, or the like is used for the robot arm sensor 143. If the ultrasonic probe 20 is brought into contact with the biological reference portion, the operator of the robot arm 140 inputs a designation instruction from an input means provided in the robot arm control circuitry 141 and formed from a button and the like. The control circuitry 112, 112a, or 112b registers, as the position of the biological reference portion, the position of the robot arm 140 grasped when the designation instruction is input.

Note that the number of robot arms provided in the position sensor system is not limited to one. The position sensor system may include the second robot arm. For example, the second robot arm is controlled to follow the biological reference portion on the body surface of the subject P. The robot arm control circuitry 141 controls the movement of the second robot arm while grasping the position of the second robot arm. The control circuitry 112, 112a, or 112b recognizes, as the position of the biological reference portion, a position followed by the second robot arm. Note that the biological reference portion exists in the body, the position of the biological reference portion is calculated based on the position followed by the second robot arm and the position of a designated portion in an ultrasonic tomographic image. Thus, even if the subject P moves during examination and it is necessary to change the posture of the subject P during examination, it is possible to continuously recognize the biological reference portion.

The above embodiment has exemplified a case in which the position sensor system 30 using the position sensor is used to acquire the position of the biological reference portion. However, the position sensor system 30 is not limited to that using the position sensor. For example, as shown in FIG. 41, a position sensor system using an imaging apparatus 150 such as a camera may be adopted.

The imaging apparatus 150 is installed at, for example, a position where the whole body of the subject P can be imaged. An image analysis apparatus recognizes the position of the ultrasonic probe 20 in the three-dimensional coordinate system by analyzing an image captured by the imaging apparatus 150. When the ultrasonic probe 20 is brought into contact with the biological reference portion, the operator of the ultrasonic diagnostic apparatus 1, 1a, or 1b inputs a designation instruction from the input means of the ultrasonic probe 20. The control circuitry 112, 112a, or 112b registers, as the position of the biological reference portion, the position of the ultrasonic probe 20 recognized when the designation instruction is input.

The first embodiment has exemplified a case in which the atlas data processing function 1121, the position information registration function 1122, the position information control function 1123, the coordinate conversion function 1124, the association function 1125 or 1125a, the support information acquisition function 1126, and the fusion function 1127 are provided in the ultrasonic diagnostic apparatus 1 or 1a, as shown in FIG. 1 or 16. However, the apparatus provided with these functions is not limited to the ultrasonic diagnostic apparatus 1 or 1a. These functions may be provided in a medical image processing apparatus such as a workstation.

In the first embodiment, the atlas image is not limited to a scheme. As the atlas image, a standardized CT image and MR image can be used.

The second embodiment has exemplified a case in which the reference portion control function 162, the coordinate conversion function 163, and the image generation function 161b are provided in the ultrasonic diagnostic apparatus 1b, as shown in FIG. 22. The apparatus provided with these functions is not limited to the ultrasonic diagnostic apparatus 1b. These functions may be provided in a medical image processing apparatus such as a workstation.

The term "processor" used in the above description means, for example, circuitry such as a CPU (Central Processing Unit), a GPU (Graphics Processing Unit), an ASIC, or a programmable logic device (for example, an SPLD, CPLD, or FPGA). The processor implements a function by reading out a program saved in the storage circuitry and executing it. Note that each processor of the embodiment is not necessarily formed as a processor. A plurality of independent circuitry may be combined to form one processor and implement the function. Furthermore, the plurality of components in FIGS. 1, 16, and 22 may be integrated into one processor, thereby implementing the function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnosis apparatus comprising:
a position detector configured to detect a position in a three-dimensional space of one of an ultrasonic image and an ultrasonic probe;
control circuitry configured to:
use a vivisection view defined in a three-dimensional space, and
associate a structure related to a subject included in the ultrasonic image with a structure included in the vivisection view using a position and orientation in a first three-dimensional coordinate system of the structure related to the subject included in the ultrasonic image and a position and orientation in a second three-dimensional coordinate system of the structure included in the vivisection view; and
image calculation circuitry configured to generate a display image including the ultrasonic image and at least a support image indicating textual information associated with the structure.

2. The apparatus of claim 1, wherein
the control circuitry recognizes an organ and/or the structure included in the ultrasonic image based on information of the vivisection view corresponding to the detected position in the three-dimensional space, and acquires support information about the recognized organ and/or the structure, and
the image calculation circuitry is configured to generate the display image including the ultrasonic image and the support information by arranging the ultrasonic image and the support information side by side or superimposing the support information on the ultrasonic image.

3. The apparatus of claim 1, further comprising:
a storage, wherein
the control circuitry specifies an organ and/or the structure included in the ultrasonic image based on information of the vivisection view corresponding to the detected position in the three-dimensional space,
the control circuitry acquires support information about the specified organ and/or the structure, and
the storage is configured to save the ultrasonic image and the support information in association with each other.

4. The apparatus of claim 2, further comprising:
a storage configured to save the support information,
wherein the control circuitry acquires an image using the support information saved in the storage.

5. The apparatus of claim 1, wherein,
the control circuitry converts, based on a position and orientation of a characteristic portion represented in the first three-dimensional coordinate system, which are detected by the position detector by scanning the ultrasonic probe, the position and orientation of the characteristic portion into a biological coordinate system, and
the control circuitry associates the structure related to the subject included in the ultrasonic image with the structure included in the vivisection view using the position and orientation in the biological coordinate system of the characteristic portion and a position and orientation in the second three-dimensional coordinate system of a characteristic portion included in the vivisection view.

6. The apparatus of claim 1, wherein the control circuitry performs association by enlarging, reducing, or deforming the second three-dimensional coordinate system based on the first three-dimensional coordinate system.

7. The apparatus of claim 5, wherein the control circuitry performs association by enlarging, reducing, or deforming the second three-dimensional coordinate system based on the biological coordinate system.

8. The apparatus of claim 1, further comprising:
an interface configured to accept designation from an operator,
wherein the control circuitry associates the structure related to the subject included in the ultrasonic image with the structure included in the vivisection view using a position and orientation in the first three-dimensional coordinate system of a structure designated via the interface and a position and orientation in the second three-dimensional coordinate system of the structure included in the vivisection view.

9. The apparatus of claim 1, wherein,
the control circuitry aligns a stored three-dimensional medical image with the first three-dimensional coordinate system, and
the control circuitry associates a characteristic portion included in the three-dimensional medical image with a characteristic portion included in the vivisection view by inter-image alignment.

10. The apparatus of claim 2, wherein if the organ and/or the structure is recognized based on the information of the vivisection view corresponding to the detected position in the three-dimensional space, the control circuitry acquires an organ content as the support information.

11. The apparatus of claim 10, wherein the organ content is an examination finding example in ultrasonic examination of the organ.

12. The apparatus of claim 10, wherein the organ content is diagnosis information and/or treatment information of the organ.

13. The apparatus of claim 10, wherein the organ content is a result of non-image examination including blood examination of the subject.

14. The apparatus of claim 2, wherein
the control circuitry acquires a name of the recognized organ and/or the structure as the support information, and
the image calculation circuitry generates the display image by assigning the name to the recognized organ and/or the structure.

15. The apparatus of claim 1, wherein the image calculation circuitry generates the ultrasonic image and at least the support image indicating the textual information associated with the structure selected by a user, and displays the ultrasonic image and at least the support image together.

16. A scan support method for an ultrasonic diagnostic apparatus, the method comprising:
detecting a position in a first three-dimensional coordinate system of one of an ultrasonic image and an ultrasonic probe;
associating a structure related to a subject included in the ultrasonic image with a structure included in a vivisection view using a position and orientation in the first three-dimensional coordinate system of the structure related to the subject included in the ultrasonic image and a position and orientation in a second three-dimensional coordinate system of the structure included in the vivisection view; and
generating a display image including the ultrasonic image and at least a support image indicating textual information associated with the structure.

17. The method of claim 16, further comprising:
recognizing an organ and/or the structure included in the ultrasonic image based on information of the vivisection view corresponding to the detected position in the first three-dimensional coordinate system;
acquiring support information about the recognized organ and/or the structure; and
generating the display image including the ultrasonic image and the support information by arranging the ultrasonic image and the support information side by side or superimposing the support information on the ultrasonic image.

18. The method of claim 16, further comprising:
recognizing an organ and/or the structure included in the ultrasonic image based on information of the vivisection view corresponding to the detected position in the first three-dimensional coordinate system;
acquiring support information about the recognized organ and/or the structure; and
saving the ultrasonic image and the support information in association with each other in a storage.

19. The method of claim 16, further comprising:
searching the image using saved support information.

20. The method of claim 16, further comprising:
converting, based on the position and orientation of a characteristic portion represented in the first three-dimensional coordinate system, which is detected by scanning the ultrasonic probe, the position and orientation of the characteristic portion into a biological coordinate system,
wherein the structure related to the subject included in the ultrasonic image is associated with the structure included in the vivisection view using the position and orientation of the characteristic portion and a position and orientation in the second three-dimensional coordinate system of a characteristic portion included in the vivisection view.

21. The method of claim 16, wherein the association is performed by enlarging, reducing, or deforming the second three-dimensional coordinate system based on the first three-dimensional coordinate system.

22. The method of claim 16, further comprising:
aligning a stored three-dimensional medical image with the first three-dimensional coordinate system,
wherein a characteristic portion included in the three-dimensional medical image is associated with a characteristic portion included in the vivisection view by inter-image alignment.

23. The method of claim 16, further comprising:
generating the ultrasonic image and at least the support image indicating the textual information associated with the structure selected by a user; and
displaying the ultrasonic image and at least the support image together.

* * * * *